(12) United States Patent
Xue et al.

(10) Patent No.: US 11,834,444 B2
(45) Date of Patent: Dec. 5, 2023

(54) PROCESSES FOR PREPARATION OF SOLUBLE GUANYLATE CYCLASE STIMULATORS

(71) Applicant: Cyclerion Therapeutics, Inc., Cambridge, MA (US)

(72) Inventors: Song Xue, Newton, MA (US); Vishnu Vardhan Reddy Karnati, Sudbury, MA (US); Robert C. Livingston, Arlington, MA (US); Timothy Claude Barden, Salem, MA (US); Wayne C. Schairer, Westboro, MA (US)

(73) Assignee: Cyclerion Therapeutics, Inc., Cambridge, MA (US)

( * ) Notice: Subject to any disclaimer, the term of this patent is extended or adjusted under 35 U.S.C. 154(b) by 375 days.

(21) Appl. No.: 16/315,221

(22) PCT Filed: Jul. 6, 2017

(86) PCT No.: PCT/US2017/040817
§ 371 (c)(1),
(2) Date: Jan. 4, 2019

(87) PCT Pub. No.: WO2018/009602
PCT Pub. Date: Jan. 11, 2018

(65) Prior Publication Data
US 2021/0284632 A1 Sep. 16, 2021

Related U.S. Application Data

(60) Provisional application No. 62/359,430, filed on Jul. 7, 2016.

(51) Int. Cl.
| | | |
|---|---|---|
| C07D 413/14 | (2006.01) | |
| C07D 413/04 | (2006.01) | |
| C07D 261/08 | (2006.01) | |
| C07D 261/18 | (2006.01) | |
| A61F 9/00 | (2006.01) | |
| A61P 43/00 | (2006.01) | |
| A61K 31/506 | (2006.01) | |
| C07C 237/06 | (2006.01) | |
| C07C 209/00 | (2006.01) | |
| C07C 231/12 | (2006.01) | |
| C07C 231/14 | (2006.01) | |
| C07C 235/06 | (2006.01) | |

(52) U.S. Cl.
CPC .......... *C07D 413/14* (2013.01); *C07C 237/06* (2013.01); *C07D 261/08* (2013.01); *C07D 261/18* (2013.01); *C07D 413/04* (2013.01)

(58) Field of Classification Search
CPC .. C07D 413/04; C07D 413/14; C07C 237/06; C07C 209/00; C07C 231/12; C07C 231/14; C07C 263/34; C07C 235/06; A61P 9/00; A61P 43/00; A61K 31/506
See application file for complete search history.

(56) References Cited

FOREIGN PATENT DOCUMENTS

| | | | |
|---|---|---|---|
| CN | 103403001 A | 11/2013 | |
| JP | 2019-524710 A | 9/2019 | |
| JP | 2019-525913 A | 9/2019 | |
| WO | 2013/101830 A1 | 7/2013 | |
| WO | WO-2013101830 A1 * | 7/2013 | ......... A61K 31/4439 |
| WO | 2014/144100 A2 | 9/2014 | |
| WO | 2016/044447 A1 | 3/2016 | |
| WO | 2017/095697 A1 | 6/2017 | |
| WO | 2018/009597 A1 | 1/2018 | |

OTHER PUBLICATIONS

International Search Report and Written Opinion for Application No. PCT/US2017/040817, dated Feb. 15, 2018, 16 pages.
Baasner et al., A New Route to the Synthesis of 5-Fluorouracil. Journal of Fluorine Chemistry. 1989;45:417-430.
Shaw et al., Selection, Purification, Characterisation, and Cloning of a Novel Heat-Stable Stereo-Specific Amidase from Klebsiella oxytoca, and Its Application in the Synthesis of Enantiomerically Pure (R)- and (S)-3,3,3-Trifluoro-2-hydroxy-2-methylpropionic Acids and (S)-3,3,3-Trifluoro-2-hydroxy-2-methylpropionamide. Organic Process Research & Development. 2002;6:497-504.

* cited by examiner

*Primary Examiner* — Sun Jae Yoo
(74) *Attorney, Agent, or Firm* — McCarter & English, LLP; Xin Zhang; Zhongyu "Alex" Wang

(57) ABSTRACT

The present disclosure relates to novel processes for the preparation of compounds useful as stimulators of soluble guanylate cyclase (sGC). These processes are amenable to large scale preparation and produce stable 3-(2-pyrimidinyl) pyrazoles of Formula (I), including Compound (I), Compound (IA) and Compound (IB), in high purity and yields. The present invention has the additional advantage of facile reaction conditions, amenable to scale up for large scale manufacturing. The disclosure also provides novel intermediates useful in the preparation of said compounds.

18 Claims, No Drawings

PROCESSES FOR PREPARATION OF SOLUBLE GUANYLATE CYCLASE STIMULATORS

CROSS-REFERENCE TO RELATED APPLICATIONS

This application is a 35 U.S.C. § 371 national stage filing of International Application No. PCT/US2017/040817, filed on Jul. 6, 2017, which claims the benefit of the filing date, under 35 U.S.C. § 119(e), of U.S. Provisional Application No. 62/359,430, filed on Jul. 7, 2016. The entire content of each of the foregoing applications is hereby incorporated by reference.

TECHNICAL FIELD

The present disclosure relates to novel processes for the preparation of compounds useful as stimulators of soluble guanylate cyclase (sGC). These processes are amenable to large scale preparation and produce stable 3-(2-pyrimidinyl) pyrazoles of Formula I in high purity and yields. The present invention has the additional advantage of involving facile reaction conditions that are amenable to scale up for large scale manufacturing. The disclosure also provides novel intermediates useful in the preparation of said compounds.

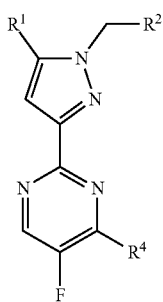

Formula I

In one aspect, compounds of Formula I and their pharmaceutically acceptable salts are sGC stimulators useful for treating diseases or disorders that benefit from sGC stimulation or from an increase in the concentration of nitric oxide (NO) and/or cyclic guanosine monophosphate (cGMP). In another aspect, compounds of Formula I are useful intermediates in the preparation of other sGC stimulators, including other compounds of Formula I.

BACKGROUND sGC is the primary receptor for NO in vivo. sGC can be activated via both NO-dependent and NO-independent mechanisms. In response to this activation, sGC converts guanosine-5'-triphosphate (GTP) into the secondary messenger cGMP. The increased level of cGMP, in turn, modulates the activity of downstream effectors including protein kinases, phosphodiesterases (PDEs) and ion channels.

In the body, NO is synthesized from arginine and oxygen by various nitric oxide synthase (NOS) enzymes and by sequential reduction of inorganic nitrate. Three distinct isoforms of NOS have been identified: inducible NOS (iNOS or NOS II) found in activated macrophage cells; constitutive neuronal NOS (nNOS or NOS I), involved in neurotransmission and long-term potentiation; and constitutive endothelial NOS (eNOS or NOS III) which regulates smooth muscle relaxation and blood pressure. Experimental and clinical evidence indicates that reduced NO concentrations, reduced NO bioavailability and/or reduced responsiveness to endogenously produced NO contributes to the development of disease.

NO-independent, heme-dependent sGC stimulators have displayed several important differentiating characteristics when compared with NO-independent, heme-independent sGC activators. These include crucial dependency on the presence of the reduced prosthetic heme moiety for their activity, strong synergistic enzyme activation when combined with NO and stimulation of the synthesis of cGMP by direct stimulation of sGC, independent of NO. The benzylindazole compound YC-1 was the first sGC stimulator to be identified. Additional sGC stimulators with improved potency and specificity for sGC have since been developed.

Compounds that stimulate sGC in an NO-independent manner offer considerable advantages over other current alternative therapies that target the aberrant NO pathway. There is a need to develop novel stimulators of sGC. There is also a need to develop efficient processes that are amenable to large scale manufacturing for the synthesis of these new sGC stimulators and, in particular, for compounds of Formula I. There is a need for efficient processes, amenable to large scale manufacturing, which provide stable sGC stimulators in high purity and yields.

SUMMARY OF THE INVENTION

Novel processes for preparing compounds of Formula I are described herein.

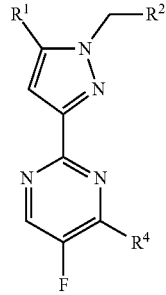

Formula I

Some compounds of Formula I and their pharmaceutically acceptable salts are sGC stimulators that are useful for treating diseases or disorders that benefit from sGC stimulation or from an increase in the concentration of NO and/or cGMP. Other compounds of Formula I are useful as intermediates in the synthesis of other sGC stimulators, including other compounds of Formula I.

For a compound of Formula I, the following definitions apply:
$R^1$ is unsubstituted phenyl, or a 5 to 6-membered heteroaryl ring containing up to three ring heteroatoms independently selected from N, O or S;
$R^2$ is phenyl or 6-membered heteroaryl, both optionally substituted with up to three instances of $R^5$; wherein said 6-membered heteroaryl ring contains up to 2 nitrogen ring atoms;
$R^4$ is halogen or —$NR^6R^7$;
each $R^5$ is independently selected from $C_{1-6}$ alkyl, $C_{1-6}$ alkoxy or halogen;

R[6] is hydrogen or $C_{1-6}$ alkyl substituted with 0-3 instances of R[8];

R[7] is hydrogen or $C_{1-6}$ alkyl substituted with 0-3 instances of R[8]; and each R[8] is independently selected from —OH, $C_{1-3}$ haloalkyl, halogen or —C(O)NH$_2$.

Novel intermediates useful in the preparation of compounds of Formula I are also disclosed herein.

DETAILED DESCRIPTION OF THE INVENTION

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls.

Definitions and General Terminology

For purposes of this disclosure, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and "March's Advanced Organic Chemistry", 5th Ed., Smith, M. B. and March, J., eds. John Wiley & Sons, New York: 2001, which are herein incorporated by reference in their entirety.

Selection of substituents and combinations envisioned by this disclosure are only those that result in the formation of stable or chemically feasible compounds. Such choices and combinations will be apparent to those of ordinary skill in the art and may be determined without undue experimentation. The term "stable", as used herein, refers to compounds that are not substantially altered when subjected to conditions to allow for their production, detection, and, in some embodiments, their recovery, purification, and use for one or more of the purposes disclosed herein. In some embodiments, a stable compound is one that is not substantially altered when kept at a temperature of 25° C. or less, in the absence of moisture or other chemically reactive conditions, for at least a week. A chemically feasible compound is a compound that can be prepared by a person skilled in the art based on the disclosures herein supplemented, if necessary, with relevant knowledge of the art.

A compound, such as the compounds of Formula I or other compounds herein disclosed, may be present in its free form (e.g. an amorphous form, or a crystalline form or a polymorph). Under certain conditions, compounds may also form co-forms. As used herein, the term co-form is synonymous with the term multi-component crystalline form. When one of the components in the co-form has clearly transferred or lost a proton, the resulting co-form is referred to as a "salt". The formation of a salt is determined by how large the difference is in the pKas between the partners that form the mixture.

In all instances described herein, the term "compound" also includes a pharmaceutically acceptable salt of the compound, whether or not the phrase "pharmaceutically acceptable salt" is actually used. The phrase "pharmaceutically acceptable salt," as used herein, refers to pharmaceutically acceptable organic or inorganic salts of a compound described herein. The pharmaceutically acceptable salts of a compound described herein are used in medicine. Salts that are not pharmaceutically acceptable may, however, be useful in the preparation of a compound described herein or of other pharmaceutically acceptable salts. A pharmaceutically acceptable salt involves the inclusion of another atom or molecule acting as the counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. In some instances, the counter ions may be the same. In other instances, they may be different for each charged atom. Hence, a pharmaceutically acceptable salt can have one or more charged atoms and/or one or more counter ions.

Pharmaceutically acceptable salts of the compounds described herein include those derived from the reaction of the compounds described herein with inorganic or organic bases. In some embodiments, the salts can be prepared in situ during the final isolation and purification of the compounds. In other embodiments, the salts can be prepared from the free form of the compound described herein in a separate synthetic step.

The preparation of the pharmaceutically acceptable salts described above and other typical pharmaceutically acceptable salts is more fully described by Berg et al., "Pharmaceutical Salts," J. Pharm. Sci., 1977:66:1-19, incorporated here by reference in its entirety.

Unless only one of the isomers is drawn or named specifically, structures depicted herein are also meant to include all stereoisomeric (e.g., enantiomeric, diastereomeric, atropoisomeric and cis-trans isomeric) forms of the structure; for example, the R and S configurations for each asymmetric center, Ra and Sa configurations for each asymmetric axis, (Z) and (E) double bond configurations, and cis and trans conformational isomers. Therefore, single stereochemical isomers as well as racemates, and mixtures of enantiomers, diastereomers, and cis-trans isomers (double bond or conformational) of the present compounds are within the scope of the present disclosure.

Unless otherwise stated, all tautomeric forms of the compounds of the present disclosure are also within the scope of the invention. As an example, a substituent drawn as below:

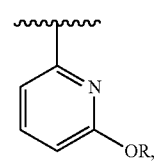

wherein R may be hydrogen, would include both compounds shown below:

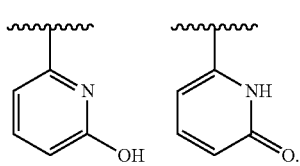

The present disclosure also embraces isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I, respectively. Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

As used herein, the terms "appropriate" and "suitable" can be used interchangeably.

As used herein, if more than one instance of a substituent is allowed at one time, then each instance of that substituent is chosen independently in each instance. For example, if a phenyl can be substituted with two instances of $R^{100}$, and $R^{100}$ is selected from halogen and methyl, then that means that each instance of $R^{100}$ is separately selected from halogen or methyl; for instance, one $R^{100}$ may be fluoro and one may be methyl, or both may be chloro, etc.

A group may be substituted with "up to" Z instances of a substituent, wherein "n" is an integer. For instance, if "Z" is 3, then the group can be substituted with 0, 1, 2, or 3 substituents. Unless otherwise specified, each of those "Z" instances are always independently selected.

The term "alkyl" (as in "alkyl chain" or "alkyl group"), as used herein, refers to a saturated linear or branched-chain monovalent hydrocarbon radical. A $C_x$ alkyl is an alkyl chain containing x carbon atoms, wherein x is an integer different from 0. A "$C_{x-y}$ alkyl", wherein x and y are two different integers, both different from 0, is an alkyl chain containing between x and y number of carbon atoms, inclusive. For example, a $C_{1-6}$ alkyl is an alkyl as defined above containing any number between 1 and 6 carbon atoms. Examples of alkyl groups include, but are not limited to, methyl ($C_1$ alkyl), ethyl ($C_2$ alkyl), n-propyl ($C_3$ alkyl), isopropyl $C_3$ alkyl), n-butyl, isobutyl, s-butyl, t-butyl, pentyl, hexyl, heptyl, octyl and the like.

As used herein, the term "aryl" (as in "aryl ring" or "aryl group") refers to a carbocyclic ring system that is aromatic and has a single point of attachment to the rest of the molecule. An example of an aryl ring is phenyl.

The term "heteroaryl" (as in "heteroaromatic" or "heteroaryl group" or "heteroaryl ring") refers to a ring system that is aromatic and contains one or more heteroatoms, which has a single point of attachment to the rest of the molecule. In some embodiments, a heteroaryl ring is a 5 to 6-membered heteroaryl ring. In other embodiments, it is a 5-membered heteroaryl ring. In still other embodiments, it is a 6-membered heteroaryl ring. Examples of heteroaryl rings include, but are not limited to the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl.

The term "ring atom" refers to an atom such as C, N, O or S that is part of the ring of a phenyl or a heteroaryl ring. A "substitutable ring atom" is a ring carbon or nitrogen atom bonded to at least one hydrogen atom. The hydrogen can be optionally replaced with a suitable substituent group. "Substitutable ring atom" does not include ring carbon or nitrogen atoms when the structure depicts that they are already attached to one or more moiety other than hydrogen and no hydrogens are available for substitution. When a certain ring, group or chain is optionally substituted, it will be understood that it may be substituted in any or some or all of its substitutable ring atoms.

"Heteroatom" refers to one or more of oxygen, sulfur, or nitrogen, including any oxidized form of nitrogen or sulfur, the quaternized form of any basic nitrogen, or a substitutable nitrogen of a heterocyclic or heteroaryl ring, for example N (as in 3,4-dihydro-2H-pyrrolyl), NH (as in pyrrolidinyl) or NR$^+$ (as in N-substituted pyrrolidinyl).

As used herein, the terms "halogen" or "halo" means F, Cl, Br, or I.

The term "haloalkyl" means alkyl substituted with one or more halogen atoms. For example a $C_{1-3}$ haloalkyl could be —CFHCH$_2$CHF$_2$. The term "fluoroalkyl" means alkyl substituted with one or more fluorine atoms. This term includes perfluorinated alkyl groups, such as —CF$_3$ and —CF$_2$CF$_3$.

As used herein, the term "alkoxy" refers to an alkyl group, as previously defined, attached to the molecule, or to another chain or ring, through an oxygen atom. "Alkoxy" can be described as —O—C$_{x-y}$ alkyl or C$_{x-y}$ alkoxy.

The term "hydroxyl" or "hydroxy" refers to —OH.

The term "solvent" as used herein refers to an individual solvent or to a mixture of solvents that result in the desired properties of the solvent mixture. For instance, an aprotic organic solvent or an aprotic solvent, as defined below, could be toluene, or it could be a mixture of toluene and another aprotic solvent such as DMF. Thus, as used herein the term aprotic organic solvent or aprotic solvent could also encompass a toluene/DMF mixture as long as the resulting properties of the mixture are those of an aprotic solvent. As another example, a protic solvent, as defined below, could encompass water or a mixture of water and methanol.

As used herein, a "protic solvent" is a solvent that has a hydrogen atom bound to a polar group, such as oxygen (as in a hydroxyl group) or nitrogen (as in an amine group). In general terms, any solvent that contains labile H+ is called a protic solvent. The molecules of such solvents readily donate protons (H+) to reagents. Conversely, "aprotic solvents" cannot easily donate hydrogen. Protic solvents are usually polar solvents as they have high dielectric constants and high polarity. Aprotic solvents are usually classified as either polar aprotic or non-polar (or apolar) aprotic depending on the values of their dielectric constants. The terms "aprotic solvent" and "aprotic organic solvent" are used interchangeably.

Some common characteristics of protic solvents are the ability to display hydrogen bonding, having acidic hydrogens (although they may be very weakly acidic, such as ethanol) and that they are able to dissolve salts. Non-limiting examples include water, most alcohols (e.g., methanol, ethanol, propanol, butanol, isopropanol, isobutanol, etc.), formic acid, hydrogen fluoride, nitromethane, acetic acid and ammonia.

Some common characteristics of aprotic solvents are that they can accept hydrogen bonds, do not have acidic hydrogen and are, only sometimes, able to dissolve salts. These criteria are relative and very qualitative. A range of acidities are recognized for aprotic solvents. Their ability to dissolve salts depends strongly on the nature of the salt.

Polar aprotic solvents usually can dissolve salts. They lack an acidic hydrogen. Consequently, they are not hydrogen bond donors. These solvents generally have intermediate dielectric constants and polarity. Although it discourages the use of the term "polar aprotic", IUPAC describes such solvents as having both high dielectric constants and high dipole moments, an example being acetonitrile. Other solvents meeting IUPAC's criteria include N,N-dimethylformamide (DMF), N,N-dimethylacetamide (DMA), N-methylpyrrolidone (NMP), hexamethylphosporamide (HMPA), tetrahydrofuran, ethyl acetate, acetone, acetonitrile (MeCN), and dimethylsulfoxide (DMSO).

Apolar or non-polar aprotic solvents usually have small dielectric constants. Some examples of apolar or non-polar aprotic (organic) solvents are hexane, pentane, decane and other alkanes, benzene, toluene, 1, 4-dioxane, chloroform, ethers such as diethyl ether, dichloromethane, dichloroethane, etc.

The term "equivalent", as used herein, when discussing an amount of a reagent used, refers to "molar equivalent". For instance, one equivalent of reagent A for each equivalent of reagent B, means one mole of reagent A for each mole of reagent B is used in the reaction. A mole is defined as the number that results when the total weight of a substance used is divided by the molecular weight of said substance, both weights being in the same units (for example, grams).

The compounds of the invention are defined herein by their chemical structures and/or chemical names. Where a compound is referred to by both a chemical structure and a chemical name, and the chemical structure and chemical name conflict, the chemical structure is determinative of the compound's identity.

Substituents are generally defined when introduced and retain that definition throughout the specification and in all independent claims.

EMBODIMENTS

Novel processes for preparing compounds of Formula I are described herein.

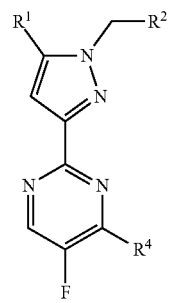

Formula I

Some compounds of Formula I and their pharmaceutically acceptable salts are sGC stimulators that are useful for treating diseases or disorders that benefit from sGC stimulation or from an increase in the concentration of NO and/or cGMP. Other compounds of Formula I are useful as intermediates in the synthesis of other sGC stimulators, including other compounds of Formula I. For a compound of Formula I, the following definitions apply:

$R^1$ is unsubstituted phenyl or 5 to 6-membered heteroaryl ring containing up to three ring heteroatoms independently selected from N, O or S;

$R^2$ is phenyl or a 6-membered heteroaryl, both optionally substituted with up to three instances of $R^5$; wherein said 6-membered heteroaryl ring contains up to 2 nitrogen ring atoms;

$R^4$ is halogen or $-NR^6R^7$;

each $R^5$ is independently selected from $C_{1-6}$ alkyl, $C_{1-6}$ alkoxy or halogen;

$R^6$ is hydrogen or $C_{1-6}$ alkyl substituted with 0-3 instances of $R^8$;

$R^7$ is hydrogen or $C_{1-6}$ alkyl substituted with 0-3 instances of $R^8$; and each $R^8$ is independently selected from $-OH$, $C_{1-3}$ haloalkyl, halogen or $-C(O)NH_2$.

In one aspect, described herein is a process for making a compound of Formula II, depicted below, said process comprising the steps of:

i) amidating starting material (1) by reacting it with an appropriate amount of oxalyl chloride or an equivalent reagent, in a suitable aprotic organic solvent, at a suitable temperature, in the presence of an appropriate amount of a suitable catalyst; followed by an appropriate amount of N, O-dimethylhydroxylamine hydrochloride, in the presence of an appropriate excess of a suitable base, at a suitable temperature, in a suitable mixture of water and an aprotic solvent under anhydrous or aqueous condition to afford amide (2);

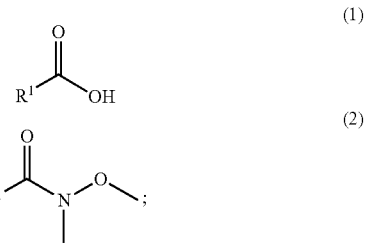

wherein $R^1$ is unsubstituted phenyl or 5 to 6-membered heteroaryl ring containing up to three ring heteroatoms independently selected from N, O or S;

ii) alkylating intermediate amide (2) with an appropriate amount of ethyl propiolate, in a suitable aprotic organic solvent, at a suitable temperature, in the presence of an appropriate amount of a suitable base, to afford β-enaminoketoester (3);

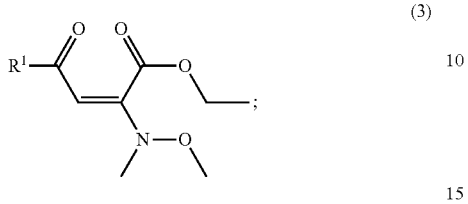

iii) condensing β-enaminoketoester (3) with an appropriate amount of a hydrazine of formula $R^2$—$CH_2$—NH—$NH_2$ or its HCl salt, optionally in the presence of an appropriate amount of a suitable base (in order to neutralize the acid from the hydrazine hydrochloride, when the hydrochloride form of the hydrazine is used), in a suitable protic solvent, at a suitable temperature, affording pyrazole ester intermediate (4); wherein $R^2$ is phenyl or a 6-membered heteroaryl, both optionally substituted with up to three instances of $R^5$; wherein the 6-membered heteroaryl ring contains up to 2 nitrogen ring atoms;

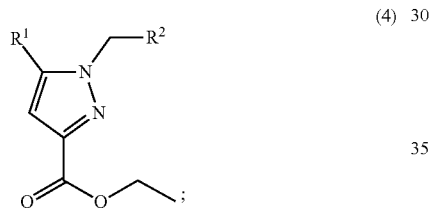

iv) aminating pyrazole ester intermediate (4) with an appropriate amount of ammonium chloride, in the presence of an appropriate amount of trimethylaluminum, in a suitable aprotic organic solvent, at a suitable temperature, affording amidine (5A) or, after treatment with a suitable aqueous mineral acid, amidine salt (5B);

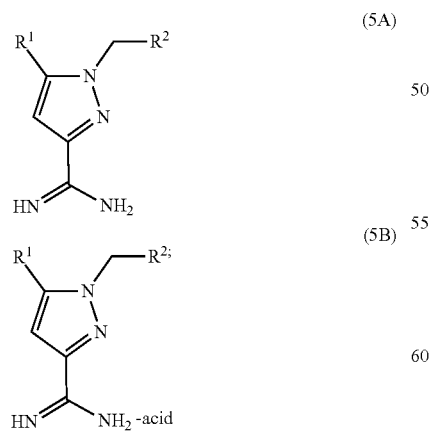

v) condensing amidine (5A) or amidine salt (5B) and an appropriate amount of fluoromalonate, optionally in the presence of an appropriate amount of a suitable base, in a suitable protic solvent, at a suitable temperature to afford, after treatment with an appropriate amount of a suitable mineral acid, diol (6);

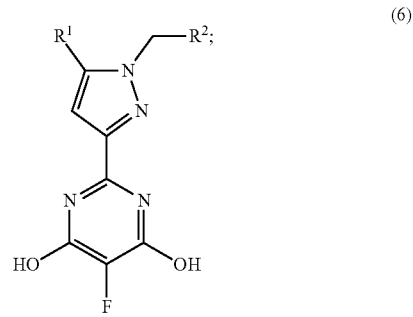

vi) chlorinating diol (6) with an appropriate amount of phosphoryl chloride, at a suitable temperature, in a suitable aprotic organic solvent, optionally in the presence of an appropriate amount of a suitable base, to afford dichloropyrimidine (7);

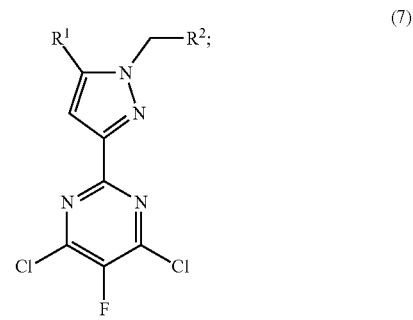

vii) mono-methoxylating dichloropyrimidine (7) with an appropriate amount of sodium methoxide, at a suitable temperature, in an appropriate protic solvent, to afford methoxypyrimidine (8);

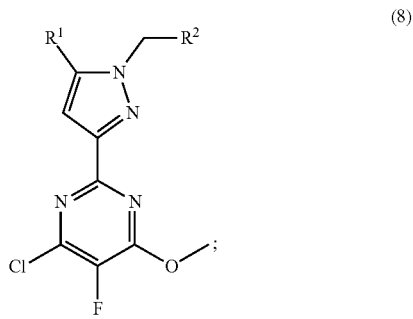

viii) de-chlorinating methoxypyrimidine (8) with hydrogen gas or a transfer hydrogenation reagent and, optionally, an appropriate amount of a suitable metal catalyst, in the presence of an appropriate amount of a suitable base, at a suitable temperature, in an appropriate organic solvent, to provide fluoromethoxypyrimidine (9);

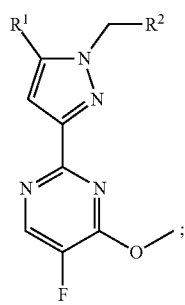

(9)

ix) de-methylating fluoromethoxypyrimidine (9) by reacting it with an appropriate amount of an aqueous acid in an appropriate protic solvent, at a suitable temperature, to afford alcohol (10);

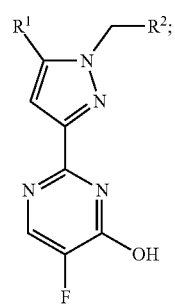

(10)

and x) chlorinating alcohol (10) with an appropriate amount of phosphoryl chloride and optionally an appropriate amount of a suitable base, at a suitable temperature, in a suitable aprotic organic solvent, to afford a chloropyrimidine of Formula II;

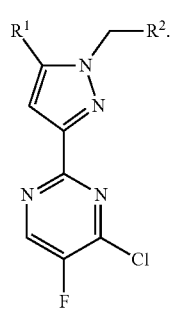

Formula II

In another aspect, described herein is an alternative process for the synthesis of a compound of Formula II comprising the steps of:

1) mono-hydroxylating a dichloropyrimidine (7) with an appropriate amount of sodium hydroxide, at a suitable temperature, in a suitable mixture of an aprotic and a protic solvent, in the presence of an appropriate amount of a suitable phase transfer catalyst, to afford hydroxypyrimidine (8B);

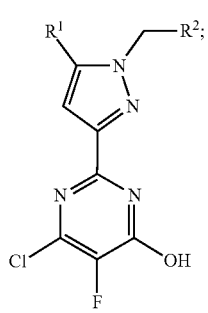

(8B)

2) de-chlorinating hydroxypyrimidine (8B) with hydrogen gas or a transfer hydrogenation reagent and, optionally, an appropriate amount of a suitable metal catalyst, in the presence of an appropriate amount of a suitable base, at a suitable temperature, in a suitable organic solvent, to provide fluorohydroxypyrimidine (10);

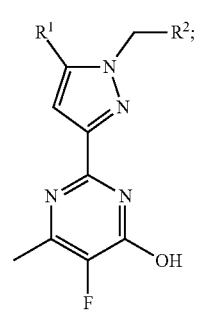

(10)

and 3) chlorinating alcohol (10) with an appropriate amount of phosphoryl chloride and optionally an appropriate amount of a suitable base, at a suitable temperature, in a suitable aprotic organic solvent, to afford a chloropyrimidine of Formula II;

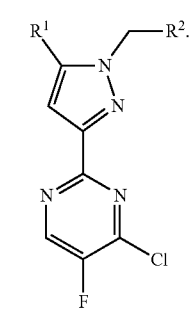

Formula II

Compounds of Formula 8B are useful as intermediates in the preparation of compounds of Formula II.

In another aspect, described herein is an alternative one-step process for the synthesis of a compound of Formula II comprising the direct selective de-chlorination of dichloropyrimidine (7) with hydrogen gas or a transfer hydrogenation reagent and, optionally, and an appropriate amount of a suitable metal catalyst, in the presence of an appropriate amount of a suitable base, at a suitable temperature, in an appropriate suitable organic solvent, to provide mono-chloropyrimidine of Formula II.

In some embodiments of the above processes for making a compound of Formula II, for compounds of Formula II and for intermediates (1) to (10) and (8B), $R^1$ is an unsubstituted 5-membered heteroaryl ring containing up to 3 heteroatoms independently selected from N, O or S. In further embodiments, $R^1$ is isoxazolyl. In other embodiments, $R^1$ is 3-isoxazolyl.

In other embodiments of the above processes for making a compound of Formula II, for compounds of Formula II and intermediates (1) to (10) and (8B), $R^1$ is unsubstituted phenyl or 6-membered heteroaryl ring containing up to 3 ring nitrogen atoms. In some embodiments, $R^1$ is a pyridine or pyrimidine. In other embodiments, $R^1$ is phenyl.

In some embodiments of the above processes for making a compound of Formula II, for compounds of Formula II, intermediates (4) to (10) and (8B), and the hydrazine of formula $R^2$—$CH_2$—NH—$NH_2$, or its corresponding hydrochloride, $R^2$ is a 6-membered heteroaryl optionally substituted with up to three instances of $R^5$. In other embodiments, $R^2$ is phenyl optionally substituted with up to three instances of $R^5$. In other embodiments, $R^2$ is phenyl substituted with one instance of $R^5$. In further embodiments, $R^2$ is phenyl substituted with one instance of $R^5$ and $R^5$ is halogen. In other embodiments, $R^2$ is phenyl substituted with one instance of $R^5$ and $R^5$ is fluoro. In other embodiments, $R^2$ is 2-fluorophenyl. In yet other embodiments, $R^2$ is phenyl substituted with two instances of $R^5$. In yet other embodiments, $R^2$ is phenyl substituted with two instances of $R^5$ and each instance of $R^5$ is independently selected from halogen. In still other embodiments, $R^2$ is phenyl substituted with two instances of $R^5$ and each instance of $R^5$ is fluoro.

In another aspect, described herein is a one-step process for making a compound of Formula III:

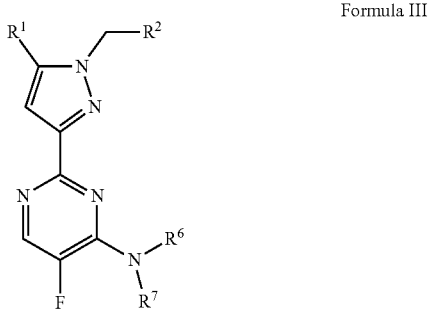

Formula III

The one-step process for making a compound of Formula III comprises coupling an appropriate amount of an amine (13) with a chloropyrimidine of Formula II, in a suitable aprotic organic solvent, optionally in the presence of an appropriate amount of a suitable base, at a suitable temperature, to yield a compound of Formula III.

(13)

In another aspect, described herein is an alternative process for making a compound of Formula III comprising the steps of:

A) coupling an appropriate amount of an amine (13) with a dichloropyrimidine (7), in a suitable aprotic organic solvent, optionally in the presence of an appropriate amount of a suitable base, at a suitable temperature, to yield an intermediate of Formula VII.

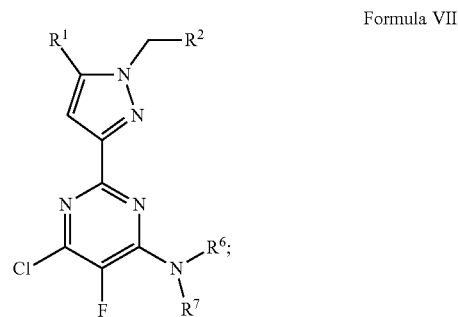

Formula VII and

B) de-chlorinating intermediate of Formula VII with hydrogen gas or a transfer hydrogenation reagent and, optionally, an appropriate amount of a suitable metal catalyst, in the presence of an appropriate amount of a suitable base, at a suitable temperature, in a suitable organic solvent, to provide a compound of Formula III.

In some embodiments of the above processes for making a compound of Formula III, for compounds of Formula III and for the intermediates of Formula II and Formula VII, $R^1$ is an unsubstituted 5-membered heteroaryl ring containing up to three ring heteroatoms independently selected from N, O or S. In further embodiments, $R^1$ is isoxazolyl. In other embodiments, $R^1$ is 3-isoxazolyl.

In other embodiments of the above processes for making a compound of Formula III, for compounds of Formula III and for the intermediate of Formula II and Formula VII, $R^1$ is an unsubstituted phenyl or 6-membered heteroaryl containing up to three ring nitrogen atoms. In other embodiments, $R^1$ is pyrimidine or pyridine. In still other embodiments, $R^1$ is pyridine. In yet other embodiments, $R^1$ is phenyl.

In some embodiments of the above processes for making a compound of Formula III, for compounds of Formula III and the intermediate of Formula II and Formula VII, $R^2$ is a 6-membered heteroaryl optionally substituted with up to three instances of $R^5$. In other embodiments, $R^2$ is phenyl optionally substituted with up to three instances of $R^5$. In other embodiments, $R^2$ is phenyl substituted with one instance of $R^5$. In further embodiments, $R^2$ is phenyl substituted with one instance of $R^5$ and $R^5$ is halogen. In other embodiments, $R^2$ is phenyl substituted with one instance of $R^5$ and $R^5$ is fluoro. In other embodiments, $R^2$ is 2-fluorophenyl. In yet other embodiments, $R^2$ is phenyl substituted with two instances of $R^5$. In yet other embodiments, $R^2$ is phenyl substituted with two instances of $R^5$ and each instance of $R^5$ is independently selected from halogen. In still other embodiments, $R^2$ is phenyl substituted with two instances of $R^5$ and each instance of $R^5$ is fluoro.

In some embodiments of the above processes of making compounds of Formula III, $R^6$ is hydrogen, methyl or ethyl in intermediate (13), in the compound of Formula III and in the intermediate of Formula VII. In some embodiments of the process of making compounds of Formula III, $R^6$ is hydrogen in intermediate (13), in the compound of Formula III and in the intermediate of Formula VII.

In some embodiments of the above processes of making compounds of Formula III, $R^7$ is $C_{1-6}$ alkyl in said intermediate 13 and said compound of Formula III and intermediate of Formula VII; wherein said $C_{1-6}$ alkyl is substituted with up to 3 instances of $R^8$. In other embodiments, $R^7$ is $C_{1-2}$ alkyl; wherein said $C_{1-2}$ alkyl is substituted with up to 3 instances of $R^8$. In other embodiments, $R^7$ is ethyl, substituted with 3 instances of $R^8$.

In some embodiments of the above processes of making compounds of Formula III, for said compounds of Formula III and said intermediate 13, or intermediate of Formula VII, one instance of $R^8$ is —OH. In other embodiments, one instance of $R^8$ is —OH and one instance is $C_{1-3}$haloalkyl. In other embodiments, one instance of $R^8$ is —OH and one instance is a trifluoromethyl.

In some embodiments of the above processes of making compounds of Formula III, $R^7$ is ethyl in said intermediate 13 and said compound of Formula III and intermediate of Formula VII; wherein said ethyl is substituted with 3 instances of $R^8$; wherein one of the three instances of $R^8$ is —OH. In other embodiments, $R^7$ is ethyl substituted with 3 instances of $R^8$; wherein one of said instances of $R^8$ is —OH and another instance of $R^8$ is $C_{1-3}$haloalkyl. In some embodiments, one instance of $R^8$ is —OH and another instance of $R^8$ is trifluoromethyl. In other embodiments, $R^7$ is ethyl, substituted with three instances of $R^8$; wherein one instance of $R^8$ is —OH, one instance of $R^8$ is trifluoromethyl and the third instance of $R^8$ is —C(O)NH$_2$.

In another aspect, described herein is a process for making a compound of Formula IV, the process comprising the steps of:

i) amidating starting material (1') by reacting it with an appropriate amount of oxalyl chloride or an equivalent reagent, in a suitable aprotic organic solvent, at a suitable temperature, in the presence of an appropriate amount of a suitable catalyst; followed by an appropriate amount of N,O-dimethylhydroxylamine hydrochloride, in the presence of an appropriate excess of a suitable base, at a suitable temperature, in a suitable mixture of water and an aprotic organic solvent to afford amide (2');

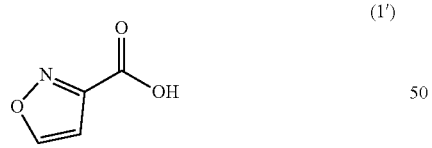
(1')

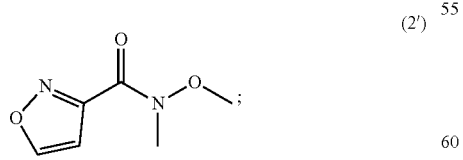
(2')

ii) alkylating intermediate amide (2') with an appropriate amount of ethyl propiolate, in a suitable aprotic organic solvent, at a suitable temperature, in the presence of an appropriate amount of a suitable base, to afford β-enaminoketoester (3');

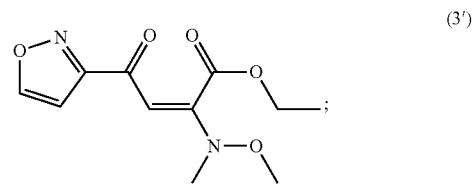 [SMILES: CCOC(=O)/C(=C\C(=O)c1ccon1)N(C)OC]
(3')

iii) condensing β-enaminoketoester (3') with an appropriate amount of a hydrazine of formula NH$_2$NH—CH$_2$-(2-fluorophenyl) or its HCl salt, optionally in the presence of an appropriate amount of a suitable base (in order to neutralize the acid from the hydrazine hydrochloride, when the hydrochloride form of the hydrazine is used), in a suitable protic solvent, at a suitable temperature, affording a pyrazole ester intermediate (4');

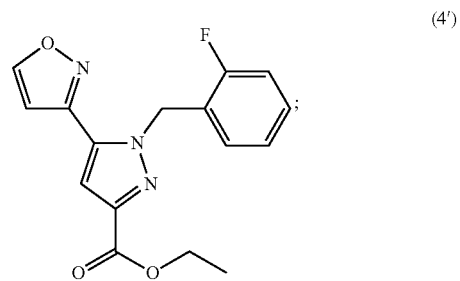 [SMILES: CCOC(=O)c1cc(-c2ccon2)n(Cc2ccccc2F)n1]
(4')

iv) aminating pyrazole ester intermediate (4') with an appropriate amount of ammonium chloride, in the presence of an appropriate amount of trimethylaluminum, in a suitable aprotic organic solvent, at a suitable temperature, affording amidine (5'A) or, after treatment with a suitable aqueous mineral acid, amidine salt (5'B);

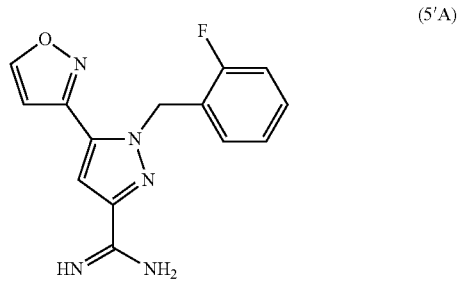
(5'A)

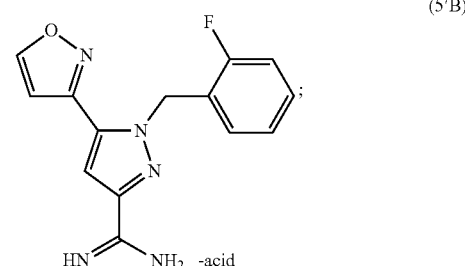
(5'B)

v) condensing amidine (5'A) or amidine salt (5'B) and an appropriate amount of fluoromalonate, optionally in the presence of an appropriate amount of a suitable base, in a suitable protic solvent, at a suitable temperature to afford, after treatment with an appropriate amount of a suitable mineral acid, diol (6');

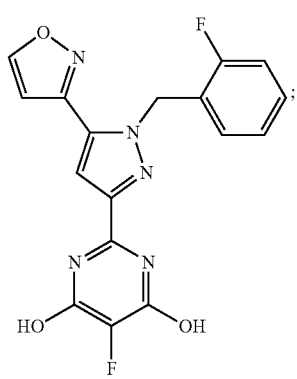

(6')

vi) chlorinating diol (6') with an appropriate amount of phosphoryl chloride, at a suitable temperature, in a suitable aprotic organic solvent, optionally in the presence of an appropriate amount of a suitable base, to afford dichloropyrimidine (7');

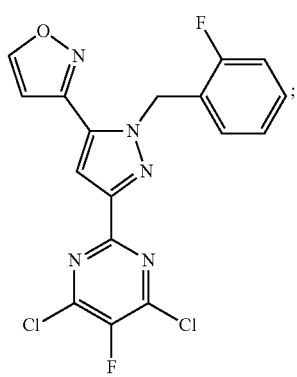

(7')

vii) mono-methoxylating dichloropyrimidine (7') with an appropriate amount of sodium methoxide, at a suitable temperature, in an appropriate protic solvent, to afford methoxypyrimidine (8');

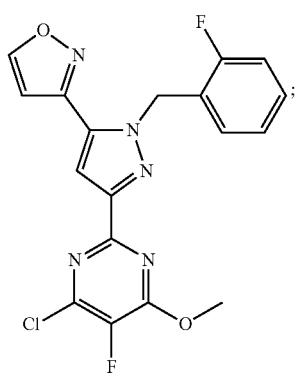

(8')

viii) dechlorinating methoxypyrimidine (8') with hydrogen gas or a transfer hydrogenation reagent and, optionally, an appropriate amount of a suitable metal catalyst, in the presence of an appropriate amount of a suitable base, at a suitable temperature, in an appropriate of organic solvent, to provide fluoromethoxypyrimidine (9');

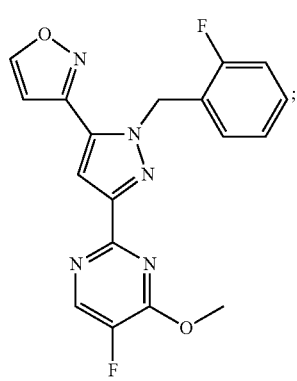

(9')

ix) de-methylating fluoromethoxypyrimidine (9') by reacting it with an appropriate amount of an aqueous acid, in an appropriate protic solvent, at a suitable temperature, to afford alcohol (10');

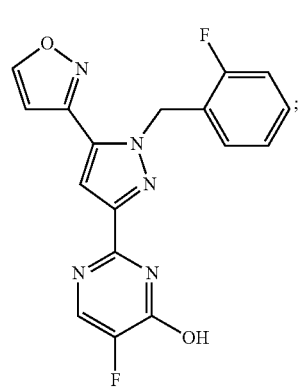

(10')

and x) chlorinating alcohol (10') with an appropriate amount of phosphoryl chloride and, optionally, an appropriate amount of a suitable base, at a suitable temperature, in a suitable aprotic organic solvent to afford a chloropyrimidine of Formula IV.

Formula IV

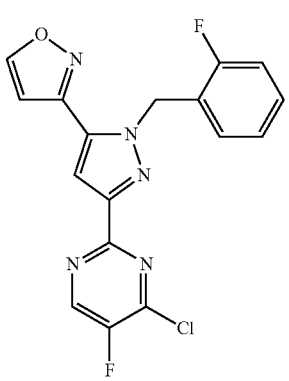

In another aspect, described herein is an alternative process for the synthesis of a compound of Formula IV comprising the steps of:

1) mono-hydroxylating a dichloropyrimidine (7') with an appropriate amount of sodium hydroxide, at a suitable temperature, in a suitable mixture of an aprotic and a protic solvent, in the presence of an appropriate amount of a suitable phase transfer catalyst, to afford hydroxypyrimidine (8'B);

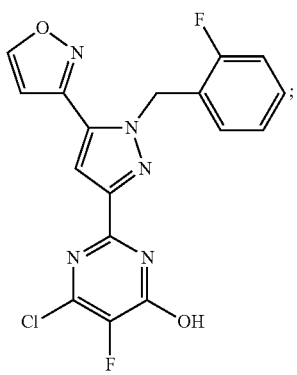

(8'B)

2) de-chlorinating hydroxypyrimidine (8'B) with hydrogen gas or a transfer hydrogenation reagent and, optionally, and an appropriate amount of a suitable metal catalyst, in the presence of an appropriate amount of a suitable base, at a suitable temperature, in a suitable organic solvent, to provide fluorohydroxypyrimidine (10');

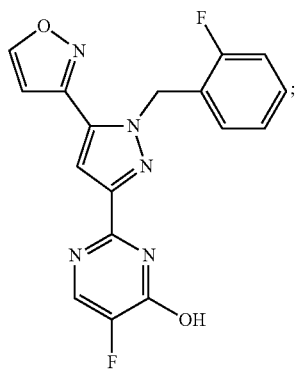

(10')

and 3) chlorinating alcohol (10') with an appropriate amount of phosphoryl chloride and optionally an appropriate amount of a suitable base, at a suitable temperature, in a suitable aprotic organic solvent, to afford a chloropyrimidine of Formula IV;

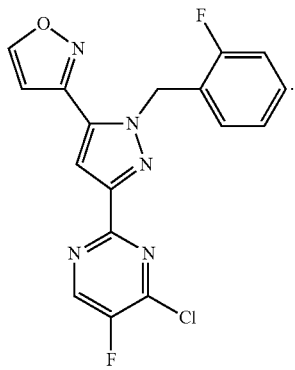

Formula IV

In another aspect, described herein is an alternative one-step process for the synthesis of a compound of Formula IV comprising the direct selective de-chlorinating of dichloropyrimidine (7') with hydrogen gas or a transfer hydrogenation reagent and, optionally, and an appropriate amount of a suitable metal catalyst, in the presence of an appropriate amount of a suitable base, at a suitable temperature, in a suitable organic solvent, to provide the mono-chloropyrimidine of Formula IV.

For step i) towards the synthesis of compounds of Formula II or Formula IV:

A suitable equivalent reagent to oxalyl chloride is, for instance thionyl chloride or 1-Ethyl-3-(3-dimethylaminopropyl)carbodiimide (EDAC).

An appropriate amount of oxalyl chloride or equivalent reagent is at least one equivalent of oxalyl chloride per equivalent of starting material (1) or starting material (1'). In some embodiments, an appropriate amount is between about 1 and about 3 equivalents. In other embodiments, an appropriate amount is between about 1 and about 2 equivalents. In still other embodiments, an appropriate amount is between about 1 and about 1.5 equivalents. In yet other embodiments, an appropriate amount is between about 1.1 and about 1.3 equivalents. In yet other embodiments, an appropriate amount is about 1.1 equivalents or about 1.2 equivalents.

A suitable aprotic organic solvent is, for instance toluene. Other suitable solvents are, for example, methylene chloride or tetrahydrofuran.

A suitable catalyst is DMF.

An appropriate amount of DMF is a catalytic amount, i.e., less than one equivalent of DMF per each equivalent of starting material (1) or starting material (1'). In some embodiments, an appropriate amount is between about 0.01 and about 0.09 equivalents. In other embodiments, it is between about 0.01 and about 0.07 equivalents. In still other embodiments, it is between about 0.02 and about 0.07 equivalents. In still other embodiments it is between about 0.04 and about 0.06 equivalents.

A suitable temperature for the reaction of starting material (1) or starting material (1') with oxalyl chloride or thionyl chloride is a temperature between about 45° C. and about 60° C. In some embodiments, a suitable temperature is between about 45° C. and about 50° C. In other embodiments, it is a temperature of about 50° C.

A suitable temperature for the reaction of starting material (1) or starting material (1') with EDAC is a temperature between about −10° C. and about 25° C. In some embodiments, a suitable temperature is between about −10° C. and about 20° C. In some embodiments, a suitable temperature is between about −10° C. and about 0° C. In some embodiments, a suitable temperature is between about −10° C. and about −5° C.

An appropriate amount of N,O-dimethylhydroxylamine hydrochloride is at least one equivalent of N,O-dimethylhydroxylamine hydrochloride per each equivalent of starting material (1) or starting material (1'). In other embodiments, an appropriate amount of N,O-dimethylhydroxylamine hydrochloride is between about 1 equivalent and about 2 equivalents per each equivalent of starting material (1) or starting material (1'). In other embodiments, it is between about 1 equivalent and about 1.5 equivalents. In other embodiments, it is between about 1 equivalent and about 1.2 equivalents. In other embodiments, it is between about 1.1 equivalents and about 1.2 equivalents.

A suitable base is, for instance, $K_2CO_3$ or NaOH. Other suitable inorganic bases are, for example, $NaHCO_3$, $KHCO_3$, $Et_3N$, or Hunig's base.

An appropriate excess of said suitable base is at least 1.1 equivalents of base per equivalent of N,O-dimethylhydroxylamine hydrochloride used. In some embodiments, an appropriate amount is between about 1.1 and about 5 equivalents of base per equivalent of N,O-dimethylhydroxylamine hydrochloride. In some embodiments, an appropriate amount is between about 1.2 and about 5 equivalents of base per equivalent of N,O-dimethylhydroxylamine hydrochloride. In other embodiments, it is about 2 to about 3 equivalents. In still other embodiments, it is between about 2 and about 4 equivalents. In other embodiments, it is about 1.2 to about 3 equivalents. In other embodiments, it is about 1.2 to about 3 equivalents. In other embodiments, it is about 1.5 to about 3 equivalents. In other embodiments, it is about 1.2 to about 4 equivalents. In still other embodiments, it is between about 1.5 and about 4 equivalents. In other embodiments, it is about 1.2 to about 2 equivalents.

A suitable temperature for the reaction of N,O-dimethylhydroxylamine hydrochloride and the suitable base is a temperature between about −10° C. and about 25° C. In some embodiments, a suitable temperature is between about −10° C. and about 20° C. In some embodiments, a suitable temperature is between about −10° C. and about 0° C. In some embodiments, a suitable temperature is between about −10° C. and about −5° C.

A suitable solvent for the water/aprotic organic solvent mixture is, for instance, dichloromethane (DCM). Other suitable solvents are, for example, ethyl acetate, tetrahydrofuran and 2-methyltetrahydrofuran.

For step ii) towards the synthesis of compounds of Formula II or Formula IV:

An appropriate amount of ethyl propiolate is at least one equivalent of ethyl propiolate per equivalent of intermediate (2) or intermediate (2'). In some embodiments, an appropriate amount of ethyl propiolate is between about 1 and about 2 equivalents. In other embodiments, it is between about 1 and about 1.8 equivalents. In other embodiments, it is between about 1 and about 1.6 equivalents. In still other embodiments, it is between about 1.1 and about 1.5 equivalents. In yet other embodiments, it is about 1.1 equivalents. In still other embodiments, it is about 1.5 equivalents.

A suitable aprotic organic solvent is an anhydrous organic solvent. For instance, a suitable solvent is anhydrous tetrahydrofuran (THF). Other suitable solvents in this step are, for example, 2-methyltetrahydrofuran and toluene.

A suitable temperature is a temperature of about −75° C. to about −30° C. In some embodiments, a suitable temperature is one between about −70° C. to about −50° C. In some embodiments, a suitable temperature is between about −65° C. to about −50° C. In other embodiments, a suitable temperature is between about −65° C. to about −55° C. In still other embodiments, a suitable temperature is between about −70° C. to about −60° C.

A suitable base is, for instance, sodium bis(trimethylsilyl)amide (NaHMDS). Other suitable bases are, for instance, lithium bis(trimethylsilyl)amide, potassium bis(trimethylsilyl)amide and lithium diisopropylamide.

An appropriate amount of a suitable base is between about 1 equivalent and about 1.65 equivalents per each equivalent of intermediate (2) or intermediate (2'). In some embodiments, it is between about 1 equivalent and about 1.5 equivalents. In some embodiments, it is between about 1 equivalent and about 1.3 equivalents. In other embodiments, it is between about 1.1 equivalents and about 1.65 equivalents. In other embodiments, it is between about 1.1 equivalents and about 1.5 equivalents. In still other embodiments, it is between about 1.1 equivalents and about 1.4 equivalents. In yet other embodiments it is between 1.1 equivalents and about 1.3 equivalents.

For step iii) towards the synthesis of compounds of Formula II or Formula IV:

An appropriate amount of hydrazine is at least one equivalent of hydrazine per each equivalent of intermediate (3) or intermediate (3'). In some embodiments, an appropriate amount of hydrazine is between about 1 equivalent and about 2 equivalents. In other embodiments, it is between about 1 equivalent and about 1.5 equivalent. In still other embodiments, it is between about 1 equivalent and about 1.3 equivalents. In still other embodiments, it is between about 1.1 equivalents and about 1.4 equivalents. In still other embodiments it is between 1.1 equivalents and about 1.3 equivalents.

An optional suitable base is, for instance, potassium carbonate ($K_2CO_3$) Other optional suitable organic bases in this step are, for example, sodium acetate (NaOAc), sodium carbonate ($Na_2CO_3$), sodium hydrogen carbonate ($NaHCO_3$) and potassium bicarbonate ($KHCO_3$).

An appropriate amount of a suitable base is an amount that will neutralize the acid from the hydrazine hydrochloride, when the hydrochloride form of the hydrazine is used. For instance, about 0.5 to about 1.1 equivalents of base per each equivalent of hydrazine hydrochloride. In other embodiments, an appropriate amount is about 0.5 to about 0.9 equivalents. In still other embodiments, it is about 0.65 equivalents.

A suitable protic solvent is, for instance, absolute ethanol or isopropanol. Other solvents that may be used in this step are, for example dichloromethane, isopropanol and methanol.

A suitable temperature is between about 0° C. and about 40° C. In other embodiments, a suitable temperature is between about 0° C. and about 30° C. In some embodiments, it is between about 0° C. and about 25° C. In other embodiments, it is between about 0° C. and about 15° C. In other embodiments, it is between about 0° C.

and about 10° C. In still other embodiments, it is between about 10° C. and about 25° C.

For step iv) towards the synthesis of compounds of Formula II or Formula IV:

An appropriate amount of ammonium chloride is between about 2.5 and about 6 equivalents of ammonium chloride for each equivalent of intermediate (4) or intermediate (4'). In some embodiments, an appropriate amount is between about 2.5 and about 5.5 equivalents. In some embodiments, an appropriate amount is between about 3.5 and about 4 equivalents. In other embodiments, an appropriate amount is about 3.8 equivalents. In still other embodiments, an appropriate amount is about 3.5 equivalents. In some embodiments, an appropriate amount is between about 4.5 equivalents and 5.0 equivalents. In other embodiments, an appropriate amount is about 4.8 equivalents.

An appropriate amount of trimethylaluminum is between about 2.5 and about 5.5 equivalents of trimethylaluminum for each equivalent of intermediate (4) or intermediate (4'). In some embodiments, an appropriate amount is between about 3.5 and about 5.5 equivalents. In other embodiments, an appropriate amount is between about 3.5 and about 4.5 equivalents. In other embodiments, an appropriate amount is between about 3.5 and about 4 equivalents. In other embodiments, an appropriate amount is about 3.5 equivalents.

A suitable aprotic organic solvent is, for instance, toluene. Other suitable solvents are, for example, xylene.

A suitable temperature for toluene is between about 60° C. and about 115° C. In some embodiments, a suitable temperature is between about 70° C. and about 110° C. In other embodiments, it is between about 70° C. and about 110° C. In still other embodiments, it is between about between about 80° C. and about 110° C. In still other embodiments, it is between about 90° C. and about 110° C.

A suitable temperature for xylene is between about 70° C. and about 130° C.

A suitable aqueous mineral acid is concentrated HCl, for instance 3 N HCl or 37% by weight HCl. Other suitable mineral acids that can be used to induce the precipitation of the intermediate (4) or intermediate (4') are, for instance, $H_2SO_4$.

For step v) towards the synthesis of compounds of Formula II or Formula IV:

An appropriate amount of fluoromalonate is at least one equivalent of fluoromalonate per each equivalent of intermediate (5A) or (5B) or intermediate (5'A) or (5'B). In some embodiments, it is between about 1 equivalent and about 2 equivalents of fluoromalonate. In still other embodiments, it is between about 1.2 equivalents and about 2 equivalents. In still other embodiments, it is between about 1.3 and about 1.9 equivalents. In other embodiments, it is between 1.4 and 1.6 equivalents. In other embodiments, it is between about 1.7 and 1.9 equivalents.

A suitable base is, for instance, sodium methoxide (NaOMe). Typically, NaOMe is added as a solution in MeOH. For example, a 23% wt solution in MeOH can be used. In other embodiments, as 30% wt solution in MeOH can be used. Alternatively, a 5.4 M solution in MeOH could be used. Other bases that could be used in this step include EtONa.

An appropriate amount of a suitable base is an excess with respect to the amount of intermediate (5A) or (5B) or intermediate (5'A) or (5'B). In some embodiments, an appropriate amount is between about 3 and about 10 equivalents of NaOMe per each equivalent of intermediate (5A) or (5B) or intermediate (5'A) or (5'B). In other embodiments, an appropriate amount is between about 3 and about 6 equivalents. In still other embodiments, it is between about 3 and about 5 equivalents. In still other embodiments, it is between about 4 and about 5 equivalents. In yet other embodiments, an appropriate amount is about 4.5 equivalents.

A suitable protic solvent is, for example, MeOH. Other suitable solvents that could be used in this step include EtOH.

A suitable temperature is between about 10° C. and about 40° C. In some embodiments, a suitable temperature is between about 15° C. and about 35° C. In other embodiments, a suitable temperature is between about 15° C. and about 30° C. In other embodiments, a suitable temperature is between about 20° C. and about 35° C. In still other embodiments, a suitable temperature is between about 20° C. and about 30° C.

A suitable mineral acid is, for example, 1.5 N HCl. Other suitable mineral acids that could be used in this step include sulfuric acid.

An appropriate amount of a mineral acid is at least an excess with respect to the amount of the suitable base used. In some embodiments, an appropriate amount is at least one equivalent of mineral acid per each equivalent of base used (e.g., NaOMe). In some embodiments, an appropriate amount is about 1.1 equivalents of mineral acid per each equivalent of base. In some embodiments, an appropriate amount of mineral acid is between about 4.5 and about 5.5 equivalents of mineral acid per each equivalent of intermediate (5B) or intermediate (5'B). In other embodiments, an appropriate amount of mineral acid is between about 4.7 and about 5.0 equivalents. In still other embodiments, it is about 4.9 equivalents.

For step vi) towards the synthesis of compounds of Formula II or Formula IV:

An appropriate amount of $POCl_3$ is at least two equivalents of $POCl_3$ per each equivalent of intermediate (6) or intermediate (6') used. In some embodiments, an appropriate amount of $POCl_3$ is at least 4 equivalents. In some embodiments, an appropriate amount is at least 5 equivalents. In still other embodiments, an appropriate amount is about 6 equivalents of $POCl_3$ per each equivalent of intermediate (6) or intermediate (6').

A suitable temperature is between about 60° C. and about 90° C. In some embodiments, a suitable temperature is between about 65° C. and about 90° C. In other embodiments, a suitable temperature is between about 70° C. and about 90° C. In still other embodiments, a suitable temperature is between about 75° C. and about 90° C. In yet other embodiments, a suitable temperature is between about 70° C. and about 80° C.

A suitable aprotic organic solvent is, for instance, acetonitrile (CNMe). The reaction can also be carried out in neat $POCl_3$, in the absence of any solvents.

A suitable optional base is, for instance, N,N-dimethylaniline. The reaction also works in the absence of a base.

An appropriate amount of a suitable base is between about 0.2 and about 2 equivalents of base per each equivalent of intermediate (6) or intermediate (6') used. In some embodiments, an appropriate amount of base is between about 1.5 and about 1.8 equivalents. In other embodiments, it is between about 0.8 equivalents and about 1.2 equivalents. In still other embodiments, it is about 1 equivalent.

For step vii) towards the synthesis of compounds of Formula II or Formula IV:

An appropriate amount of sodium methoxide (NaOMe) is about 1 equivalent of NaOMe per each equivalent of intermediate (7) or intermediate (7'). In some embodiments, an appropriate amount of NaOMe is a slight excess of NaOMe per each equivalent of intermediate (7) or intermediate (7'). In some embodiments, an appropriate amount of NaOMe is between 1.1 and 1.3 equivalents per each equivalent of intermediate (7) or intermediate (7'). In other embodiments, an appropriate amount is about 1.2 equivalents.

A suitable temperature is between about 15° C. and about 30° C. In some embodiments, a suitable temperature is between about 20° C. and about 30° C. In other embodiments, it is between about 15° C. and about 28° C. In other embodiments, between about 20° C. and about 28° C. In still other embodiments, between about 23° C. and about 27° C.

A suitable protic solvent is, for instance, methanol (MeOH).

For step viii) towards the synthesis of compounds of Formula II or Formula IV:

A suitable transfer hydrogenation reagent is HCOOH. HCOOH was most commonly used in the presence of organic/inorganic bases such as Et$_3$N, NaOH, NaHCO$_3$, etc. HCOONH$_4$, HCOONa, HCOOK, iso-propanol, triethylsilane, and cyclohexadiene may also be used.

A suitable metal catalyst is palladium on activated carbon, for instance 10% Pd on activated carbon.

An appropriate amount of a suitable metal catalyst is a catalytic amount, i.e., less than one equivalent of Pd per equivalent of intermediate (8) or intermediate (8'). In some embodiments, an appropriate amount of the suitable metal catalyst is between 0.01 and 0.03 equivalents of Pd per equivalent of intermediate (8) or intermediate (8'). In other embodiments, an appropriate amount of the suitable metal catalyst is between 0.01 and 0.025 equivalents of Pd per equivalent of intermediate (8) or intermediate (8'). In still other embodiments, an appropriate amount of the suitable metal catalyst is between 0.015 and 0.025 equivalents of Pd per equivalent of intermediate (8) or intermediate (8'). In yet other embodiments, an appropriate amount of the suitable metal catalyst is between 0.01 and 0.02 equivalents of Pd per equivalent of intermediate (8) or intermediate (8').

A suitable base is triethylamine (Et$_3$N). Other suitable bases that can be used are, for example, Hunig's base, NaHCO$_3$, KHCO$_3$, and sodium acetate.

An appropriate amount of a suitable base is at least one equivalent of base per each equivalent of intermediate (8) or intermediate (8'). In some embodiments, a suitable amount of base is at least 1.5 equivalents. In other embodiments, it is about 1.6 equivalents.

A suitable temperature is between about 35° C. and about 60° C. A suitable temperature is between about 35° C. and about 55° C. In some embodiments, a suitable temperature is between about 40° C. and about 50° C.

A suitable organic solvent is, for example, THF. Other solvents that can be used are, for instance methanol, ethanol, isopropanol, 2-methyl-tetrahydrofuran or mixtures thereof.

For step ix) towards the synthesis of compounds of Formula II or Formula IV:

A suitable aqueous acid is HCl. Other acids that could be used include, for instance, methylsulfonic acid (MeSO$_3$H) or HBr.

An appropriate amount of acid is between about 3 and about 6 equivalents. In some embodiments, an appropriate amount is between about 4 and about 6 equivalents. In other embodiments, it is between about 4.5 equivalents and about 6 equivalents. In still other embodiments, it is about 4.90 to about 5 equivalents. HCl can be provided, for instance, in the form of concentrated HCl (e.g., 37 wt % HCl).

A suitable protic solvent is, for instance, MeOH. Other suitable protic solvents are EtOH and iPrOH.

A suitable temperature is between about 50° C. and about 70° C. In some embodiments, a suitable temperature is between about 55° C. and about 65° C. In still other embodiments, a suitable temperature is between about 60° C. and about 65° C. In still other embodiments, a suitable temperature is between about 62° C. and about 65° C.

For step x) towards the synthesis of compounds of Formula II or Formula IV:

An appropriate amount of POCl$_3$ is at least two equivalents of POCl$_3$ per each equivalent of intermediate (10) or intermediate (10') used. In some embodiments, an appropriate amount of POCl$_3$ is at least 4 equivalents. In some embodiments, an appropriate amount is at least 3 equivalents. In some embodiments, an appropriate amount is at least 2 equivalents. In some embodiments, an appropriate amount is at least 1 equivalent. In still other embodiments, an appropriate amount is between about 1 and about 4 equivalents of POCl$_3$ per each equivalent of intermediate (10) or intermediate (10').

A suitable temperature is between about 50° C. and about 90° C. In some embodiments, a suitable temperature is between about 60° C. and about 90° C. In some embodiments, a suitable temperature is between about 65° C. and about 90° C. In other embodiments, a suitable temperature is between about 70° C. and about 90° C. In still other embodiments, a suitable temperature is between about 75° C. and about 90° C. In yet other embodiments, a suitable temperature is between about 75° C. and about 85° C. In other embodiments, a suitable temperature is between about 75° C. and about 80° C.

A suitable aprotic organic solvent is, for instance, acetonitrile (CNMe). The reaction can also be carried out in neat POCl$_3$, in the absence of any solvents.

A suitable optional base is, for instance, N,N-dimethylaniline. The reaction also works in the absence of a base.

An appropriate amount of a suitable base is between about 0.2 and about 2 equivalents of base per each equivalent of intermediate (10) or intermediate (10') used. In some embodiments, an appropriate amount of base is between about 1.3 and about 1.6 equivalents. In some embodiments, an appropriate amount of base is between about 1.2 and about 1.8 equivalents. In other embodiments, it is about 1 equivalent.

For step 1) towards the synthesis of compounds of Formula II or Formula IV:

An appropriate amount of sodium hydroxide (NaOH) is between about 2 and about 2.5 equivalents of NaOH per each equivalent of intermediate (7) or intermediate (7'). In other embodiments, an appropriate amount is about 2.2 equivalents.

A suitable temperature is between about 45° C. and about 70° C. In some embodiments, a suitable temperature is between about 500° C. and about 65° C. In other embodiments, it is between about 55° C. and about 60° C.

A suitable phase transfer catalyst is tetrabutylammonium hydroxide. Other suitable phase transfer catalysts that could be used comprise benzyltrimethylammonium chloride, benzyltriethylammonium chloride, methyltricaprylammonium chloride, methyltributylammonium chloride, and methyltrioctylammonium chloride An appropriate amount of a suitable phase transfer catalyst is a catalytic amount, i.e. less than one equivalent of phase transfer catalyst per equivalent of intermediate (7) or intermediate (7'). In some embodiments, a catalytic amount is between about 0.1 and about 0.5 equivalents. In other embodiments, it is between about 0.1 and about 2.5 equivalents. In still other embodiments, it is between about 0.1 and about 0.15 equivalents.

A suitable protic solvent is, for instance, water. A suitable aprotic organic solvent is, for example tetrahydrofuran.

For step 2) towards the synthesis of compounds of Formula II or Formula IV:

A suitable transfer hydrogenation reagent is HCOOH. HCOOH was most commonly used in the presence of organic/inorganic bases such as $Et_3N$, NaOH, $NaHCO_3$, etc. $HCOONH_4$, HCOONa, HCOOK, Isopropanol, triethylsilane, and cyclohexadiene may also be used.

A suitable metal catalyst is palladium on activated carbon, for instance 10% Pd on activated carbon.

An appropriate amount of a suitable metal catalyst is a catalytic amount, i.e., less than one equivalent of Pd per equivalent of intermediate (8B) or intermediate (8'B). In some embodiments, an appropriate amount of the suitable metal catalyst is between 0.01 and 0.02 equivalents of Pd per equivalent of intermediate (8B) or intermediate (8'B).

A suitable base is triethylamine ($Et_3N$). Other suitable bases that can be used are, for example, Hunig's base, $NaHCO_3$, $KHCO_3$, and sodium acetate.

An appropriate amount of a suitable base is at least one equivalent of base per each equivalent of intermediate (8B) or intermediate (8'B). In some embodiments, a suitable amount of base is at least 1.5 equivalents. In other embodiments, it is about 1.6 equivalents.

A suitable temperature is between about 35° C. and about 60° C. A suitable temperature is between about 35° C. and about 55° C. In some embodiments, a suitable temperature is between about 40° C. and about 50° C.

A suitable organic solvent is, for example, THF. Other solvents that can be used are, for instance methanol, ethanol, isopropanol, 2-methyl-tetrahydrofuran or mixtures thereof.

For step 3) towards the synthesis of compounds of Formula II or Formula IV:

An appropriate amount of $POCl_3$ is at least two equivalents of $POCl_3$ per each equivalent of intermediate (10) or intermediate (10') used. In some embodiments, an appropriate amount of $POCl_3$ is at least 4 equivalents. In some embodiments, an appropriate amount is at least 3 equivalents. In some embodiments, an appropriate amount is at least 2 equivalents. In some embodiments, an appropriate amount is at least 1 equivalent. In still other embodiments, an appropriate amount is between about 1 and about 4 equivalents of $POCl_3$ per each equivalent of intermediate (10) or intermediate (10').

A suitable temperature is between about 50° C. and about 80° C. In some embodiments, a suitable temperature is between about 60° C. and about 80° C. In some embodiments, a suitable temperature is between about 65° C. and about 80° C. In other embodiments, a suitable temperature is between about 70° C. and about 80° C. In still other embodiments, a suitable temperature is between about 75° C. and about 80° C.

A suitable aprotic organic solvent is, for instance, acetonitrile (CNMe). The reaction can also be carried out in neat $POCl_3$, in the absence of any solvents.

A suitable optional base is, for instance, N,N-dimethylaniline. The reaction also works in the absence of a base.

An appropriate amount of a suitable base is between about 0.2 and about 2 equivalents of base per each equivalent of intermediate (10) or intermediate (10') used. In some embodiments, an appropriate amount of base is between about 1.3 and about 1.6 equivalents. In some embodiments, an appropriate amount of base is between about 1.2 and about 1.8 equivalents. In other embodiments, it is about 1 equivalent.

For the above one-step processes for the synthesis of compounds of Formula II or compounds of Formula IV:

A suitable transfer hydrogenation reagent is HCOOH. HCOOH was most commonly used in the presence of organic/inorganic bases such as $Et_3N$, NaOH, $NaHCO_3$, etc. $HCOONH_4$, HCOONa, HCOOK, Isopropanol, triethylsilane, and cyclohexadiene may also be used.

A suitable metal catalyst is palladium on activated carbon, for instance 10% Pd on activated carbon.

An appropriate amount of a suitable metal catalyst is a catalytic amount, i.e., less than one equivalent of Pd per equivalent of intermediate (7) or intermediate (7'). In some embodiments, an appropriate amount of the suitable metal catalyst is between 0.01 and 0.02 equivalents of Pd per equivalent of intermediate (7) or intermediate (7').

A suitable base is triethylamine ($Et_3N$). Other suitable bases that can be used are, for example, Hunig's base, $NaHCO_3$, $KHCO_3$, and sodium acetate.

An appropriate amount of a suitable base is at least one equivalent of base per each equivalent of intermediate (7) or intermediate (7'). In some embodiments, a suitable amount of base is at least 1.5 equivalents. In other embodiments, it is about 1.6 equivalents.

A suitable temperature is between about 35° C. and about 60° C. A suitable temperature is between about 35° C. and about 55° C. In some embodiments, a suitable temperature is between about 40° C. and about 50° C.

A suitable organic solvent is, for example, THF. Other solvents that can be used are, for instance methanol, ethanol, isopropanol, 2-methyl-tetrahydrofuran or mixtures thereof.

In another aspect, described herein is a one-step process for making a compound of Formula V comprising coupling an appropriate amount of an amine (13) with a chloropyrimidine of Formula IV, optionally in the presence of an appropriate amount of a suitable base, in a suitable aprotic organic solvent, at a suitable temperature, to yield a compound of Formula V.

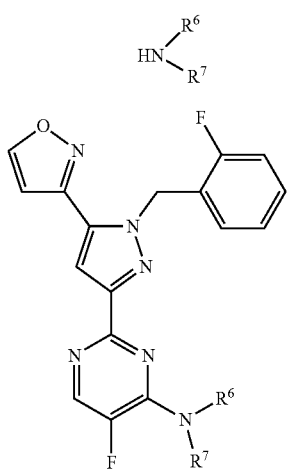

Formula V

In another aspect, described herein is an alternative process for making a compound of Formula V comprising the steps of:

A) coupling an appropriate amount of an amine (13) with a dichloropyrimidine (7'), in a suitable aprotic organic solvent, optionally in the presence of an appropriate amount of a suitable base, at a suitable temperature, to yield an intermediate of Formula VIII:

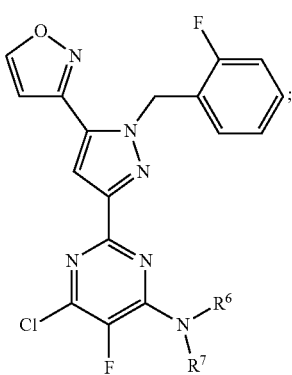

Formula VIII and

B) de-chlorinating intermediate of Formula VIII with hydrogen gas or a transfer hydrogenation reagent and, optionally, an appropriate amount of a suitable metal catalyst, in the presence of an appropriate amount of a suitable base, at a suitable temperature, in a suitable organic solvent, to provide a compound of Formula V.

In some embodiments of the above processes of making compounds of Formula V, $R^6$ is hydrogen, methyl or ethyl in intermediate (13), the compound of Formula V and the intermediate of Formula VIII. In some embodiments of the process of making compounds of Formula V, $R^6$ is hydrogen in intermediate (13), the compound of Formula V and the intermediate of Formula VIII.

In some embodiments of the above processes of making compounds of Formula V, $R^7$ is $C_{1-6}$ alkyl in intermediate 13, intermediate of Formula VIII and the compound of Formula V; wherein said $C_{1-6}$ alkyl is substituted with up to 3 instances of $R^8$. In other embodiments, $R^7$ is $C_{1-2}$ alkyl; wherein said $C_{1-2}$ alkyl is substituted with up to 3 instances of $R^8$. In other embodiments, $R^7$ is ethyl, substituted with 3 instances of $R^8$.

In some embodiments of the above processes of making compounds of Formula V, for the compounds of Formula V, intermediate of Formula VIII and the intermediate 13, one instance of $R^8$ is OH. In other embodiments, one instance of $R^8$ is OH and one instance is $C_{1-3}$ haloalkyl. In other embodiments, one instance of $R^8$ is OH and one instance is a trifluoromethyl.

In some embodiments of the above processes of making compounds of Formula V, $R^7$ is ethyl in said intermediate 13, intermediate of Formula VIII and the compound of Formula V; wherein said ethyl is substituted with 3 instances of $R^8$; wherein one of the three instances of $R^8$ is OH. In other embodiments, $R^7$ is ethyl; wherein said ethyl is substituted with 3 instances of $R^8$; wherein one of said instances of $R^8$ is OH and another instance of $R^8$ is $C_{1-3}$haloalkyl. In some embodiments, one instance of $R^8$ is OH and another instance of $R^8$ is trifluoromethyl. In other embodiments, $R^7$ is ethyl, substituted with three instances of $R^8$; wherein one instance of $R^8$ is OH, once instance of $R^8$ is trifluoromethyl and the third instance of $R^8$ is —C(O)NH$_2$.

In another aspect, described herein is a one-step process for making a compound of Formula VI.

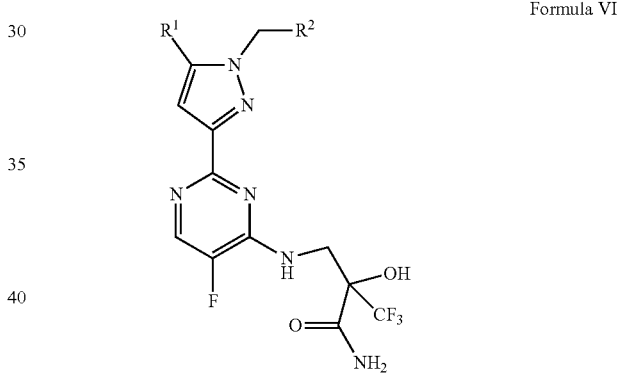

Formula VI

The one-step process for making a compound of Formula VI comprises coupling an appropriate amount of an amine (14) with a chloropyrimidine of Formula II, optionally in the presence of an appropriate amount of a suitable base, in a suitable aprotic organic solvent, at a suitable temperature, to yield a compound of Formula VI.

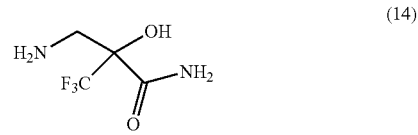

(14)

In another aspect, described herein is an alternative process for making a compound of Formula VI comprising the steps of:

A) coupling an appropriate amount of an amine (14) with a dichloropyrimidine (7), in a suitable aprotic organic solvent, optionally in the presence of an appropriate amount of a suitable base, at a suitable temperature, to yield an intermediate of Formula IX;

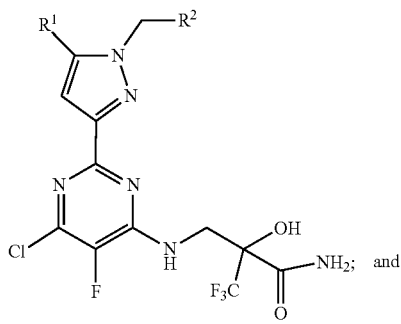

Formula IX

B) de-chlorinating the intermediate of Formula IX with hydrogen gas or a transfer hydrogenation reagent and, optionally, an appropriate amount of a suitable metal catalyst, in the presence of an appropriate amount of a suitable base, at a suitable temperature, in a suitable organic solvent, to provide a compound of Formula VI.

In another aspect, the process for making a compound of Formula VI involves the steps of:

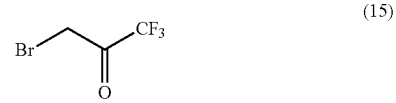
(15)

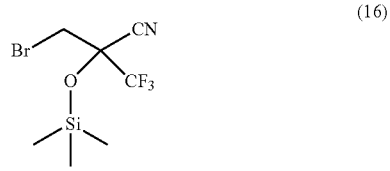
(16)

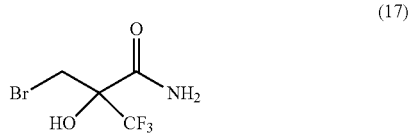
(17)

a) treating bromo intermediate 15 with an appropriate amount of trimethylsilanecarbonitrile, KCN or NaCN in the presence of an appropriate amount of a suitable organic amine, optionally in the presence of water as the solvent, at a suitable temperature to provide intermediate 16;
b) treating intermediate 16 with an appropriate amount of a strong aqueous mineral acid, at a suitable temperature, to provide intermediate 17; and
c) treating intermediate 17 with an appropriate amount of ammonia, in a suitable protic solvent, at a suitable temperature to provide amine 14.

In some embodiments of the above processes for making a compound of Formula VI, for intermediates of Formula II, and intermediates of Formula IX, $R^1$ is an unsubstituted 5-membered heteroaryl ring containing up to three ring heteroatoms independently selected from N, O or S. In further embodiments, $R^1$ is isoxazolyl. In other embodiments, $R^1$ is 3-isoxazolyl.

In other embodiments of the above processes for making a compound of Formula VI, for compounds of Formula VI and for intermediates of Formula II, and intermediates of Formula IX, $R^1$ is an unsubstituted phenyl or 6-membered heteroaryl ring containing up to three ring nitrogen atoms. In other embodiments, $R^1$ is phenyl.

In some embodiments of the above processes for making a compound of Formula VI, for compounds of Formula VI and intermediates of Formula II, and intermediates of Formula IX, $R^2$ is a 6-membered heteroaryl optionally substituted with up to three instances of $R^5$. In other embodiments, $R^2$ is phenyl optionally substituted with up to three instances of $R^5$. In other embodiments, $R^2$ is phenyl substituted with one instance of $R^5$. In further embodiments, $R^2$ is phenyl substituted with one instance of $R^5$ and $R^5$ is halogen. In other embodiments, $R^2$ is phenyl substituted with one instance of $R^5$ and $R^5$ is fluoro. In other embodiments, $R^2$ is 2-fluorophenyl. In yet other embodiments, $R^2$ is phenyl substituted with two instances of $R^5$. In yet other embodiments, $R^2$ is phenyl substituted with two instances of $R^5$ and each instance of $R^5$ is halogen. In still other embodiments, $R^2$ is phenyl substituted with two instances of $R^5$ and each instance of $R^5$ is fluoro.

In another aspect, described herein is a one-step process for making Compound I. Compound I is 3,3,3-trifluoro-2-(((5-fluoro-2-(1-(2-fluorobenzyl)-5-(isoxazol-3-yl)-1H-pyrazol-3-yl)pyrimidin-4-yl)amino) methyl)-2-hydroxypropanamide and has the structure depicted below. Compound I is an sGC stimulator that has demonstrated efficacy for the treatment of a number of NO related disorders in preclinical models.

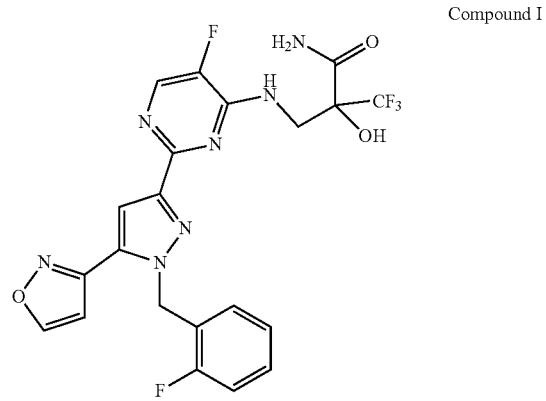 [SMILES: NC(=O)C(O)(CNc1nc(-c2cc(-c3ccon3)n(Cc3ccccc3F)n2)ncc1F)C(F)(F)F]

Compound I

The one-step process for making Compound I comprises coupling an appropriate amount of an amine (14) with a chloropyrimidine of Formula IV, optionally in the presence of an appropriate amount of a suitable base, in a suitable aprotic organic solvent, at a suitable temperature, to yield Compound I.

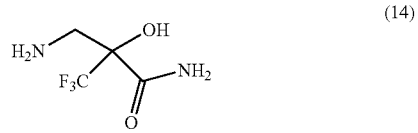 [SMILES: NCC(O)(C(N)=O)C(F)(F)F]
(14)

For the above one-step processes for making a compound of Formula III, a compound of Formula V, a compound of Formula VI, or Compound I, by reacting an intermediate of Formula II or an Intermediate of Formula IV with an amine (13) or, alternatively, an intermediate of Formula II or an intermediate of Formula IV with an amine (14):

An appropriate amount of amine (13) or amine (14) is at least one equivalent of amine (13) or amine (14) per each equivalent of compound of Formula II or compound of Formula IV. In some embodiments, an excess of amine (13) or amine (14) may be used. In some embodiments, an amount between about 1 and about 5 equivalents of the amine (13) or amine (14) can be used. In other embodiments, the appropriate amount is between about 1 and about 4 equivalents. In other embodiments, it is between about 1 and about 3 equivalents.

A suitable optional base is, for instance, Hunig's base. Other suitable optional bases are, for example, Et$_3$N, NaHCO$_3$, and KHCO$_3$. Amine (13) or amine (14) itself may also be used as the base.

An appropriate amount of a suitable base is at least one equivalent of optional base per each equivalent of intermediate of Formula II or intermediate of Formula IV. In some embodiments, an appropriate amount is about 2 equivalents.

A suitable aprotic organic solvent is dimethylsulfoxide (DMSO). Other suitable aprotic organic solvents are, for instance, N,N-dimethylformamide (DMF), N,N-dimethylacetamide (DMA), and tert-butanol (t-BuOH).

A suitable temperature is between about 100° C. and about 135° C. In some embodiments, a suitable temperature is between about 120° C. and about 130° C. In other embodiments, a suitable temperature is between about 125° C. and about 130° C.

In another aspect, described herein is an alternative process for making Compound I comprising the steps of:

A) coupling an appropriate amount of an amine (14) with a dichloropyrimidine (7'), in a suitable aprotic organic solvent, optionally in the presence of an appropriate amount of a suitable base, at a suitable temperature, to yield an intermediate of Formula X;

Formula X

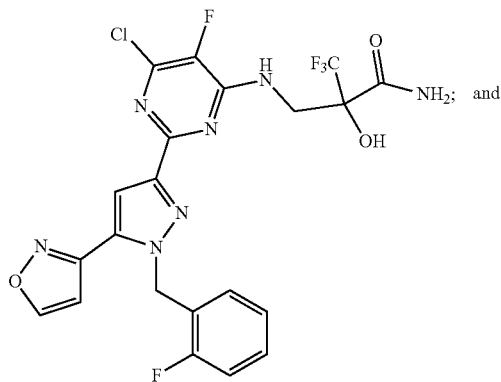

B) de-chlorinating the intermediate of Formula X with hydrogen gas or a transfer hydrogenation reagent and, optionally, an appropriate amount of a suitable metal catalyst, in the presence of an appropriate amount of a suitable base, at a suitable temperature, in a suitable organic solvent, to provide a Compound I.

In another aspect, described herein is another process for making Compound I.

This process for making Compound I comprises the steps of:
a) treating bromo intermediate (15) with an appropriate amount of trimethylsilanecarbonitrile, KCN or NaCN in the presence of an appropriate amount of a suitable organic amine, optionally in the presence of water as the solvent, at a suitable temperature to provide intermediate (16);
b) treating intermediate (16) with an appropriate amount of a suitable strong aqueous mineral acid, at a suitable temperature, to provide intermediate (17); and
c) treating intermediate (17) with an appropriate amount of ammonia, in a suitable protic solvent, at a suitable temperature to provide amine (14).

For step a) in the above processes for preparing a compound of Formula VI or a Compound I:
An appropriate amount of trimethylsilanecarbonitrile (TMSCN), KCN or NaCN is a slight defect with respect to the amount of bromo intermediate (15), i.e., slightly less than 1 equivalent of TMSCN, NaCN or KCN per each equivalent of bromo intermediate (15). In some embodiments, an appropriate amount of TMSCN, KCN or NaCN is between about 0.9 and about 1.1 equivalent of TMSCN, NaCN or KCN per each equivalent of bromo intermediate (15). In other embodiments, an appropriate amount is between about 0.95 and about 1 equivalent.

A suitable organic amine is, for instance, triethylamine (Et$_3$N). Another suitable amine is, for instance Hunig's base.

An appropriate amount of a suitable organic amine is a catalytic amount. In some embodiments, a catalytic amount is between about 0.01 equivalents and about 0.1 equivalents of amine per each equivalent of bromo intermediate (15). In other embodiments, it is between about 0.01 equivalents and about 0.05 equivalents. In other embodiments, it is between about 0.01 and about 0.03 equivalents.

A suitable temperature is between about 0° C. and about 25° C. In some embodiments, a suitable temperature is between about 5° C. and about 25° C. In other embodiments, it is between about 10° C. and about 20° C.

For step b) in the above processes for preparing a compound of Formula VI or a Compound I:
A suitable strong aqueous mineral acid is, for instance, concentrated sulfuric acid (H$_2$SO$_4$). Other aqueous mineral acids that can be used are, for example, concentrated HCl.
An appropriate amount of a strong aqueous mineral acid is an excess of acid, i.e., more than one equivalent of mineral acid per each equivalent of intermediate 16. In some embodiments, an appropriate amount is more than 2 equivalents. In other embodiments is more than 3 equivalents. In still other embodiments, it is about 4 equivalents. In other embodiments, an appropriate amount is between about 3 and about 8 equivalents.
A suitable temperature is between about 50° C. and about 90° C. In some embodiments, a suitable temperature is between about 50° C. and about 75° C. In other embodiments, a suitable temperature is between about 65° C. and about 75° C. In yet other embodiments, a suitable temperature is between about 60° C. and about 80° C. In some embodiments, a suitable temperature is between about 60° C. and about 75° C. In still other embodiments, it is a temperature below about 75° C.

For step c) in the above processes for preparing a compound of Formula VI or a Compound I:
An appropriate amount of ammonia is a large excess: i.e., a large excess with respect of number of equivalents of intermediate (17). In some embodiments, a large excess is more than 5 equivalents. In other embodiments, it is between about 5 and about 12 equivalents. In other embodiments, it is about 10 equivalents or more.

A suitable protic solvent is, for instance, MeOH. Other protic solvents that could be used are, for example EtOH, iPrOH and water.

A suitable temperature is between about 18° C. to about 30° C. In other embodiments, it is between about 18° C. to about 25° C. In still other embodiments, it is between about 20° C. to about 28° C. In yet other embodiments, it is between about 20° C. to about 25° C.

In another aspect, described herein is a one-step process for the synthesis of Compound IA. Compound IA is (R)-3,3,3-trifluoro-2-(((5-fluoro-2-(1-(2-fluorobenzyl)-5-(isoxazol-3-yl)-1H-pyrazol-3-yl)pyrimidin-4-yl) amino)methyl)-2-hydroxypropanamide and has the structure depicted below. Compound I is an sGC stimulator that has demonstrated efficacy for the treatment of a number of NO related disorders in preclinical models.

Compound IA

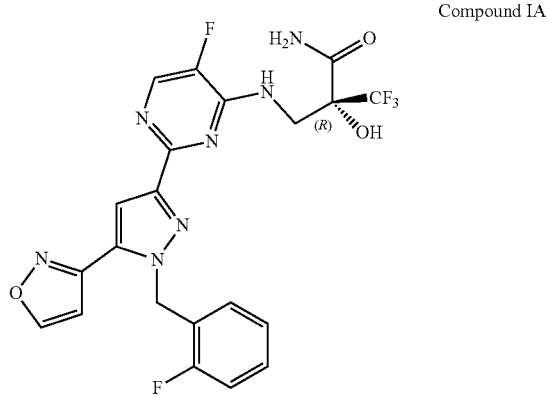

The one-step process for making Compound IA comprises coupling an appropriate amount of an amine (14A) with a chloropyrimidine of Formula IV in a suitable aprotic organic solvent, optionally in the presence of an appropriate amount of a suitable base, at a suitable temperature, to yield Compound IA.

(14A)

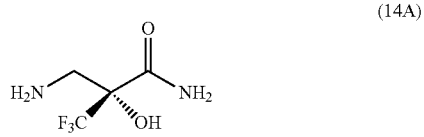 [SMILES: NC[C@@](O)(C(N)=O)C(F)(F)F]

In another aspect, described herein is an alternative process for making Compound IA comprising the steps of:

A) coupling an appropriate amount of an amine (14A) with a dichloropyrimidine (7'), in a suitable aprotic organic solvent, optionally in the presence of an appropriate amount of a suitable base, at a suitable temperature, to yield an intermediate of Formula XA.

Formula XA

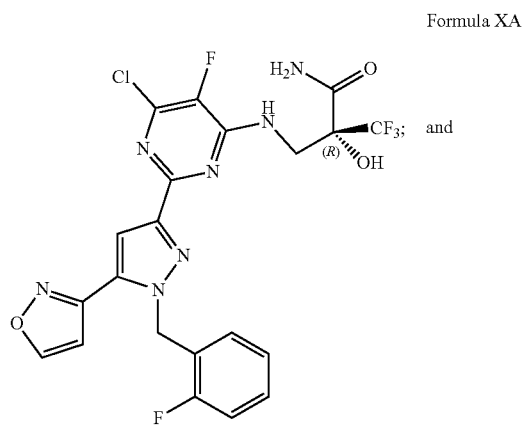

B) de-chlorinating the intermediate of Formula XA with hydrogen gas, or a transfer hydrogenation reagent, and, optionally, an appropriate amount of a suitable metal catalyst, in the presence of an appropriate amount of a suitable base, at a suitable temperature, in a suitable organic solvent, to provide a Compound IA.

In another aspect, described herein is another process for making Compound IA, comprising the steps of:

a) treating bromo intermediate (15) with an appropriate amount of trimethylsilanecarbonitrile, KCN or NaCN in the presence of an appropriate amount of a suitable organic amine, optionally in the presence of water as the solvent, at a suitable temperature to provide intermediate (16);

b) treating intermediate (16) with an appropriate amount of a suitable strong aqueous mineral acid, at a suitable temperature, to provide intermediate (17); and c) treating intermediate (17) with an appropriate amount of ammonia, in a suitable protic solvent, at a suitable temperature, to provide amine (14).

d) reacting intermediate amine (14) with an appropriate amount of (D)-malic acid in a suitable aprotic organic solvent, at a suitable temperature, to provide a 1 to 1 salt of chiral intermediate (18A) and (D)-malic acid; followed by crystallization to separate this salt from the unreacted enantiomeric amine (14B); and e) heating the (D) malic acid salt obtained in step d), at a suitable temperature, in a suitable solvent, in order to liberate intermediate (14A) into solution, with loss of acetone, and reacting the resulting solution with an intermediate fluorochloro pyrimidine of Formula IV, in a suitable solvent, at a suitable temperature, optionally in the presence of an appropriate amount of a suitable organic amine, to provide Compound IA.

(18A)

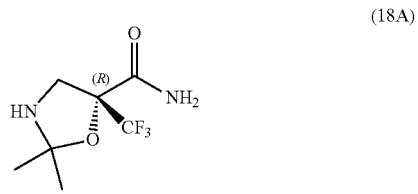

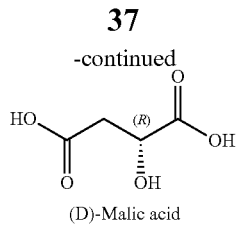

(D)-Malic acid

In another aspect, described herein is a one-step process for the synthesis of Compound IB. Compound IB is (S)-3,3,3-trifluoro-2-(((5-fluoro-2-(1-(2-fluorobenzyl)-5-(isoxazol-3-yl)-1H-pyrazol-3-yl)pyrimidin-4-yl)amino)methyl)-2-hydroxypropanamide and has the structure depicted below. Compound IB is an sGC stimulator that has demonstrated efficacy for the treatment of a number of NO related disorders in preclinical models.

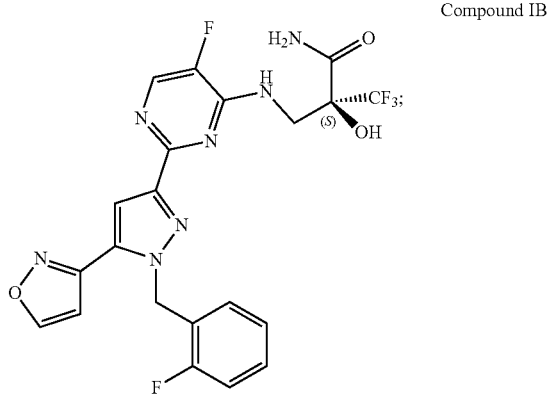

Compound IB

The one-step process for making Compound IB comprises coupling an appropriate amount of an amine (14B) with a chloropyrimidine of Formula IV in a suitable polar aprotic solvent, optionally in the presence of an appropriate amount of a suitable base, at a suitable temperature to yield Compound IB.

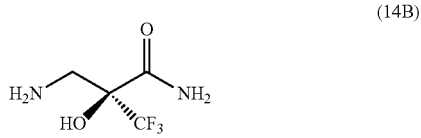 [SMILES: NC[C@](O)(C(N)=O)C(F)(F)F]
(14B)

In another aspect, described herein is an alternative process for making Compound IB comprising the steps of:

A) coupling an appropriate amount of an amine (14B) with a dichloropyrimidine (7'), in a suitable aprotic organic solvent, optionally in the presence of an appropriate amount of a suitable base, at a suitable temperature, to yield an intermediate of Formula XB.

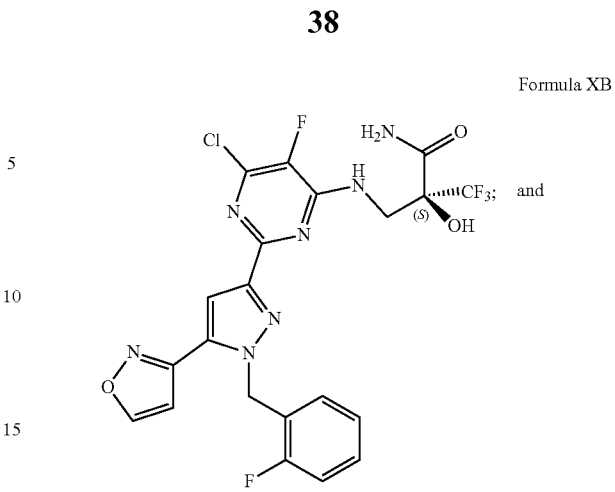
Formula XB

B) de-chlorinating the intermediate of Formula XB with hydrogen gas or a transfer hydrogenation reagent and, optionally, an appropriate amount of a suitable metal catalyst, in the presence of an appropriate amount of a suitable base, at a suitable temperature, in a suitable organic solvent, to provide a Compound IB.

In another aspect, described herein is another process for making Compound IB.

This process for making Compound IB comprises the steps of:

a) treating bromo intermediate (15) with an appropriate amount of trimethylsilanecarbonitrile, KCN or NaCN in the presence of an appropriate amount of a suitable organic amine, optionally in the presence of water as the solvent, at a suitable temperature to provide intermediate (16);

b) treating intermediate (16) with an appropriate amount of a suitable strong aqueous mineral acid, at a suitable temperature, to provide intermediate (17); and c) treating intermediate (17) with an appropriate amount of ammonia, in a suitable protic solvent, at a suitable temperature, to provide amine (14).

d) reacting intermediate amine (14) with an appropriate amount of (L)-malic acid, in a suitable aprotic polar solvent, at a suitable temperature, to provide a 1 to 1 salt of chiral intermediate (18B) and (L)-malic acid; followed by crystallization to separate this salt from the unreacted enantiomeric amine (14A); and e) heating the (L) malic acid salt obtained in step d), at a suitable temperature, in a suitable solvent, in order to liberate intermediate (14B) into solution, with loss of acetone, and reacting the resulting solution with an intermediate fluorochloro pyrimidine of Formula IV, in a suitable solvent, at a suitable temperature, optionally in the presence of an appropriate amount of a suitable organic amine, to provide Compound IB.

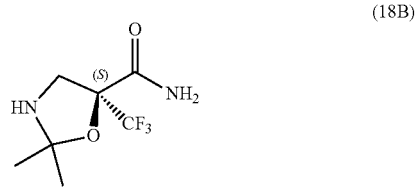
(18B)

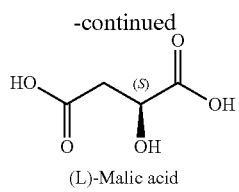

(L)-Malic acid

For step a) in the above processes for preparing a compound of Compound IA or Compound IB:
- An appropriate amount of trimethylsilanecarbonitrile (TMSCN), NaCN or KCN is a slight defect with respect to the amount of bromo intermediate (15), i.e., slightly less than 1 equivalent of TMSCN, NaCN or KCN per each equivalent of bromo intermediate (15). In some embodiments, an appropriate amount of TMSCN, KCN or NaCN is between about 0.9 and about 1.1 equivalent of TMSCN, NaCN or KCN per each equivalent of bromo intermediate (15). In other embodiments, an appropriate amount is between about 0.95 and about 1 equivalent.
- A suitable organic amine is, for instance, triethylamine (Et₃N). Another suitable amine is, for instance Hunig's base.
- An appropriate amount of a suitable organic amine is a catalytic amount. In some embodiments, a catalytic amount is between about 0.01 equivalents and about 0.1 equivalents of amine per each equivalent of bromo intermediate (15). In other embodiments, it is between about 0.01 equivalents and about 0.05 equivalents. In other embodiments, it is between about 0.01 and about 0.03 equivalents.
- A suitable temperature is between about 0° C. and about 25° C. In some embodiments, a suitable temperature is between about 5° C. and about 25° C. In other embodiments, it is between about 10° C. and about 20° C.

For step b) in the above processes for preparing a Compound IA or Compound IB:
- A suitable strong aqueous mineral acid is, for instance, concentrated sulfuric acid (H₂SO₄). Other aqueous mineral acids that can be used are, for example, concentrated HCl.
- An appropriate amount of a strong aqueous mineral acid is an excess of acid, i.e., more than one equivalent of mineral acid per each equivalent of intermediate (16). In some embodiments, an appropriate amount is more than 2 equivalents. In other embodiments is more than 3 equivalents. In still other embodiments, it is about 4 equivalents. In other embodiments, an appropriate amount is between about 3 and about 8 equivalents.
- A suitable temperature is between about 50° C. and about 90° C. In some embodiments, a suitable temperature is between about 50° C. and about 75° C. In other embodiments, a suitable temperature is between about 50° C. and about 75° C. In still other embodiments, it is a temperature below about 75° C.

For step c) in the above processes for preparing Compound IA or Compound IB:
- An appropriate amount of ammonia is a large excess: i.e. a large excess with respect of number of equivalents of intermediate (17). In some embodiments, a large excess is more than 5 equivalents. In other embodiments, it is between about 5 and about 12 equivalents. In other embodiments, it is about 10 equivalents or more.
- A suitable protic solvent is, for instance, MeOH. Other protic solvents that could be used are, for example EtOH, iPrOH and water.
- A suitable temperature is between about 10° C. and about 40° C. In some embodiments, a suitable temperature is between about 15° C. and about 35° C. In other embodiments, a suitable temperature is between about 20° C. and about 30° C. In still other embodiments, a suitable temperature is between about 20° C. and about 25° C.

For step d) in the above processes for preparing Compound IA or Compound IB:
- An appropriate amount of (L)-malic acid or (D) malic acid is 1 equivalent of (L) or (D), malic acid per equivalent of amine (14).
- A suitable aprotic polar solvent is acetone.
- A suitable temperature is between about 15° C. and about 55° C. In some embodiments, a suitable temperature is between about 20° C. and about 55° C. In other embodiments, a suitable temperature is between about 20° C. and about 40° C. In still other embodiments, a suitable temperature is between about 20° C. and about 32° C. In still other embodiments, a suitable temperature is between about 28° C. and about 32° C. In other embodiments, a suitable temperature is between about 20° C. and about 25° C.

For step e) in the above processes for preparing Compound IA or Compound IB
- A suitable solvent for heating the 1.1 malic acid salts of intermediates (18A) or (18B) obtained in step d) in order to liberate amine (14A) or amine (14B) into solution is water. Another suitable solvent is a mixture of water and DMSO.
- A suitable temperature for heating the 1:1 malic acid salts of intermediates (18A) or (18B) obtained in step d) in order to liberate amine (14A) or amine (14B) into solution is between 10° C. and 40° C. In some embodiments, it is between 10° C. and 50° C. In other embodiments, it is about 40° C.
- A suitable amount of intermediate amine (14A) or amine (14B), liberated into solution, to react with intermediate of Formula IV is at least one equivalent of amine (14A) or amine (14B) per each equivalent of intermediate of Formula IV. In other embodiments, the amount of amine is at least two equivalents. In other embodiments, it is about 2.5 equivalents. In other embodiments, it is between about 1 equivalent and about 1.5 equivalents.
- A suitable solvent for the reaction of intermediate amine (14A) or amine (14B) with intermediate of Formula IV is dimethylsulfoxide (DMSO). In other embodiments, it is a mixture of DMSO and water. Still in other embodiments, a suitable solvent that may be used is DMF or acetonitrile.
- A suitable temperature is between about 80° C. and about 100° C. In other embodiments, a suitable temperature is between about 85° C. and about 95° C. In other embodiments, it is about 90° C.
- A suitable optional organic amine is Hunig's base. Another suitable organic amine is, for example, Et₃N.
- An appropriate amount of a suitable organic amine is at least one equivalent of amine each equivalent of intermediate amine 14A or amine 14B liberated in the previous step. In some embodiments, an appropriate amount of amine is between about 1 and about 5 equivalents of intermediate of Formula IV. In other embodiments, is between about 2 and about 4 equivalents. In still other embodiments it is between about 2.5 and about 3 equivalents.

For the above one-step processes for making a Compound IA or Compound IB, by reacting an intermediate of Formula IV with an amine (14A) or an amine (14B):

An appropriate amount of an amine (14A) or amine (14B) is at least one equivalent of amine (14A) or amine (14B) per each equivalent of compound of Formula IV. In some embodiments, an excess of amine (14A) or amine (14B) may be used. In some embodiments, an amount between about 1 and about 5 equivalents of the amine (14A) or amine (14B) can be used. In other embodiments, the appropriate amount is between about 1 and about 4 equivalents. In other embodiments, is between about 1 and about 3 equivalents.

A suitable optional base is, for instance, Hunig's base. Other suitable optional bases are, for example $Et_3N$, $NaHCO_3$ and $KHCO_3$. Intermediate amines (14A) and amine (14B), when used in excess, can also be used as the base.

An appropriate amount of a suitable optional base is at least one equivalent of optional base per each equivalent of intermediate of Formula IV. In some embodiments, an appropriate amount is about 2 equivalents. In other embodiments, an appropriate amount is between about 0 and about 2 equivalents.

A suitable aprotic organic solvent is dimethylsulfoxide (DMSO). Other suitable aprotic organic solvents are for instance DMF, DMA or tert-BuOH.

A suitable temperature is between about 100° C. and about 135° C. In some embodiments, a suitable temperature is between about 125° C. and about 130° C.

For step A) in the above processes for making a compound of Formula III, a compound of Formula V, a compound of Formula VI, Compound I, Compound IA or Compound IB:

An appropriate amount of amine (13), amine (14), amine (14A) or amine (14B) is at least one equivalent of amine (13), amine (14), amine (14A) or amine (14B) per each equivalent of intermediate (7) or intermediate (7'). In some embodiments, an excess of amine (13) or amine (14) may be used. In some embodiments, an amount between about 1 and about 3 equivalents of the amine (13) or amine (14) can be used. In other embodiments, the appropriate amount is between about 1 and about 2.9 equivalents. In other embodiments, it is between about 1 and about 2.7 equivalents. In other embodiments, it is about 2.6 equivalents.

A suitable optional base is, for instance, Hunig's base. Other suitable optional bases are, for example $Et_3N$, $NaHCO_3$, and $KHCO_3$. Amine (13), amine (14), amine (14A) or amine (14B) itself may also be used as the base, if used in excess.

An appropriate amount of a suitable base is at least one equivalent of optional base per each equivalent of intermediate (7) or intermediate (7'). In some embodiments, an appropriate amount is about 2 equivalents.

A suitable aprotic organic solvent is dimethylsulfoxide (DMSO). Other suitable aprotic organic solvents are, for instance, N,N-dimethylformamide (DMF), N,N-dimethylacetamide (DMA), and tert-butanol (t-BuOH).

A suitable temperature is between about 50° C. and about 65° C. In some embodiments, a suitable temperature is between about 55° C. and about 65° C. In other embodiments, a suitable temperature is between about 57° C. and about 63° C.

For step B) in the above processes for making a compound of Formula III, a compound of Formula V, a compound of Formula VI, Compound I, Compound IA or Compound IB:

A suitable metal catalyst is palladium on activated carbon, for instance 10% Pd on activated carbon.

An appropriate amount of a suitable metal catalyst is a catalytic amount, i.e., less than one equivalent of Pd per equivalent of intermediate of Formula VII, Formula VIII, Formula IX, Formula X, Formula XA or Formula XB. In some embodiments, an appropriate amount of the suitable metal catalyst is between 0.01 and 0.02 equivalents of Pd per equivalent of intermediate of Formula VII, Formula VIII, Formula IX, Formula X, Formula XA or Formula XB.

A suitable base is triethylamine ($Et_3N$). Other suitable bases that can be used are, for example, Hunig's base, $NaHCO_3$, $KHCO_3$, and sodium acetate.

An appropriate amount of a suitable base is at least one equivalent of base per each equivalent of intermediate of Formula VII, Formula VIII, Formula IX, Formula X, Formula XA or Formula XB. In some embodiments, a suitable amount of base is at least 1.5 equivalents. In other embodiments, it is about 1.6 equivalents.

A suitable temperature is between about 35° C. and about 60° C. A suitable temperature is between about 35° C. and about 55° C. In some embodiments, a suitable temperature is between about 40° C. and about 50° C.

A suitable organic solvent is, for example, THF. Other solvents that can be used are, for instance methanol, ethanol, isopropanol, 2-methyl-tetrahydrofuran or mixtures thereof.

The processes described herein have the advantage of allowing preparation of sGC stimulators and intermediates of Formula I in high yield and purity. The present invention has the additional advantage of facile reaction conditions that are readily scaled up for large scale preparation.

In one embodiment of the above processes, the compound of Formula I is a compound of Formula II. In other embodiments, the compound of Formula I is a compound of Formula III. In another embodiment, the compound of Formula I is a compound of Formula IV. In another embodiment, it is compound of Formula V. In still other embodiments, it is a compound of Formula VI. In still other embodiments, the compound of Formula I is a Compound I (1,1,1,3,3,3-hexafluoro-2-(((5-fluoro-2-(1-(2-fluorobenzyl)-5-(isoxazol-3-yl)-1H-pyrazol-3-yl)pyrimidin-4-yl)amino) methyl)propan-2-ol). In yet other embodiments, the compound of Formula I is a compound of Formula IA or Formula IB. In yet other embodiments, it is a compound of Formula IA. In still other embodiments, it is a compound of Formula IB.

Alternative processes for the preparation of compounds of Formula II and Formula IV have previously been described in U.S. Pat. No. 8,748,442B2, WO2013101830 and WO2014144100.

In those publications, the synthesis of intermediates (4) and (4') was carried out according to Scheme 1, depicted below, using intermediate (4') as an example.

Scheme 1

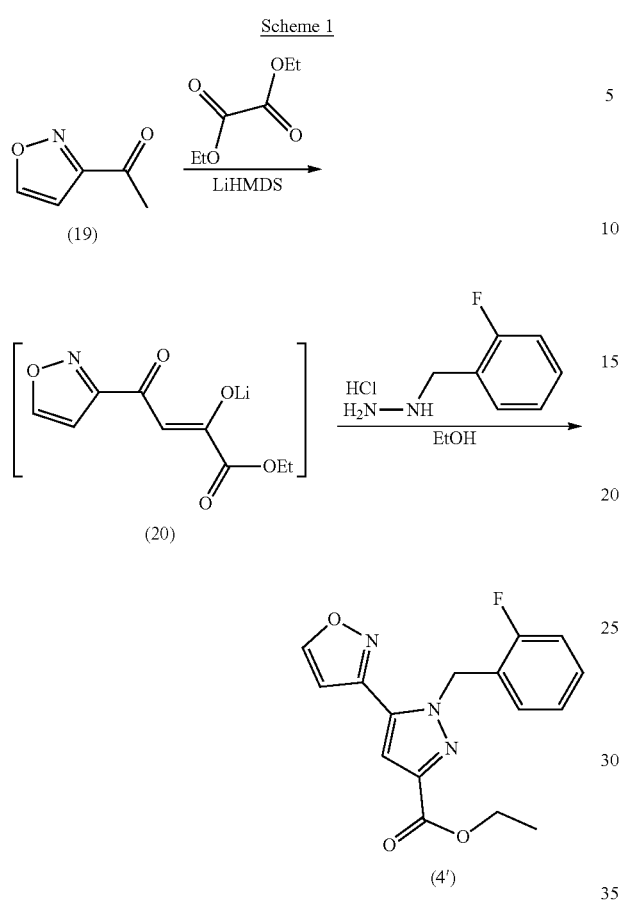

According to Scheme 1, the synthesis of intermediates (4) and (4') may be carried out in two steps. For example, for compound (4'), the first step involves reaction of a ketone (19) with diethyloxalate to provide an intermediate (20). In the second step, intermediate (20) is reacted with a suitably substituted hydrazine or its corresponding hydrochloride salt. In the particular case of compound (4'), the hydrazine would be one of Formula NH$_2$NH—CH$_2$-(2-fluorophenyl).

Herein described is the preparation of compounds (4) and (4') as carried out according to Scheme 2, exemplified for compound (4'), depicted below.

Scheme 2

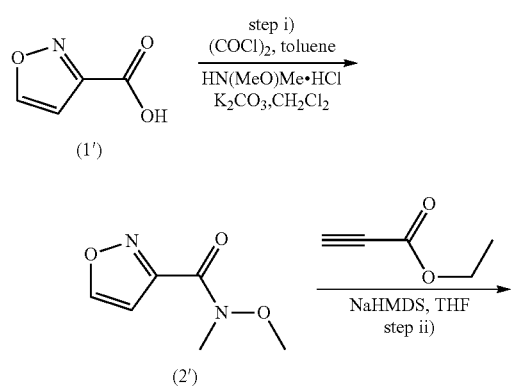

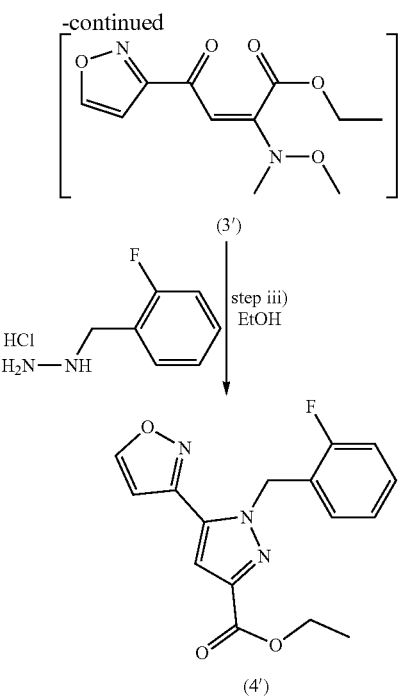

The preparation of intermediate (4) or (4') according to Scheme 2 has been found to present several advantages when compared to their preparation according to Scheme 1. Although the synthesis according to Scheme 2 introduces one additional step as compared to the synthesis according to Scheme 1, the synthesis according to Scheme 2 is more amenable to scale-up for large scale manufacturing, leading to overall higher yields and higher purities. Scheme 2 uses a compound (1') as the starting material in step i). This starting material is solid at room temperature, and is inexpensively available from commercial sources. Compound (19), used as starting material in Scheme 1, is a liquid at room temperature, which makes it harder to handle in large scale operations. Compound (19) is also substantially more expensive than compound (1') from commercial sources.

Another advantage of the synthesis according to Scheme 2 is that intermediate (3'), generated in step ii), can be re-crystallized and obtained in high purity. Intermediate (20) of Scheme 1 is used without additional purification in the second step of the reaction, resulting in a less pure final product and a more complicated purification process. Further, the second step in the preparation of compound (4) or compound (4') in the synthesis according to Scheme 1 occurs with a very low degree of regioselectivity for the desired regioisomer of (4) or (4'), which is depicted in the above schemes. The less desirable regioisomers of structures (4B) and (4'B) are depicted below. The low regioselectivity observed during the syntheses according to Scheme 1 poses a loss of overall yield of the desired isomer, as well as necessitating a lengthy and less efficient purification processes to isolate the pure desired isomer.

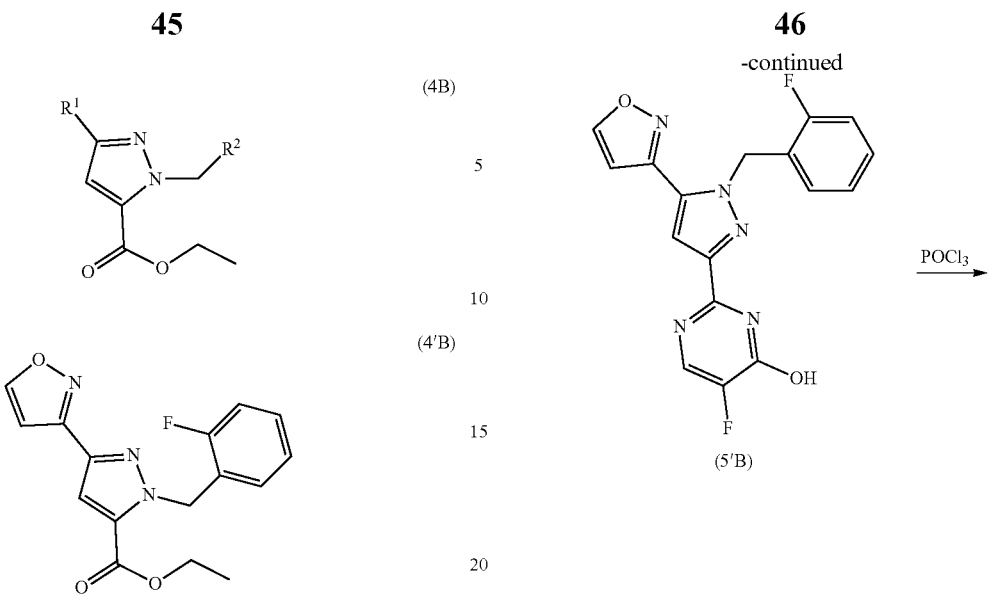

In publications U.S. Pat. No. 8,748,442B2, WO2013101830 and WO2014144100, the preparation of compounds of Formula II or compounds of Formula IV from either intermediate amidines (5A) or (5A'), or intermediate amidine salts (5B) or (5'B), was carried out according to Scheme 3, via the formation of intermediate (10'), as exemplified for a final compound of Formula IV below.

Scheme 3

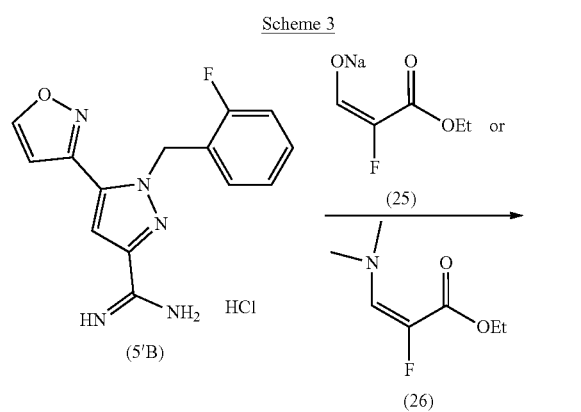

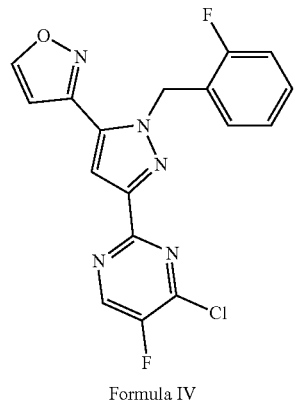

Formula IV

Herein disclosed is the preparation of compounds of Formula II or compounds of Formula IV from the corresponding amidines (5A) or (5A') or amidine salts (5B) or (5B') by one of several alternative processes. These are exemplified for a final compound of Formula IV in Scheme 4 below.

Scheme 4

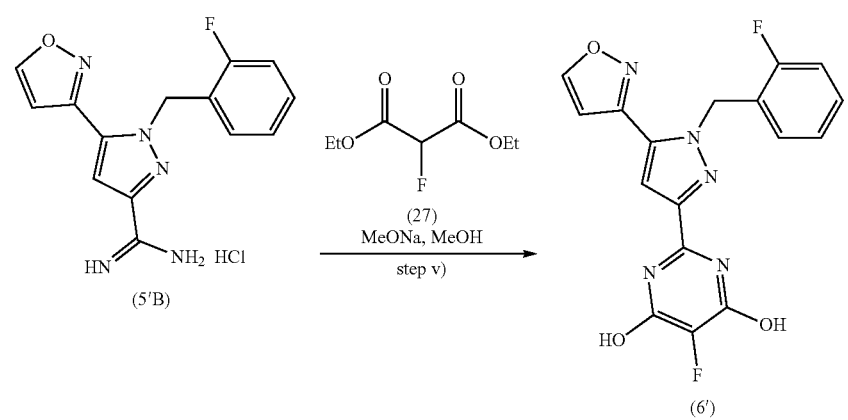

-continued step vi) | POCl₃

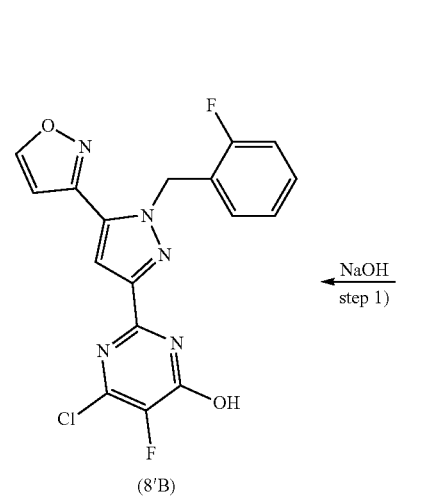

(8'B)      (7')      (8')

NaOH step 1) ←    → MeONa, MeOH step vii)

H₂, Pd/C step 2)      H₂, Pd/C one-step process      H₂, Pd/C step viii)

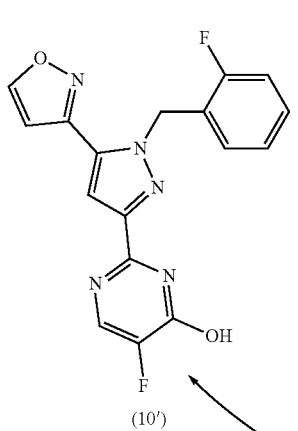

(10')

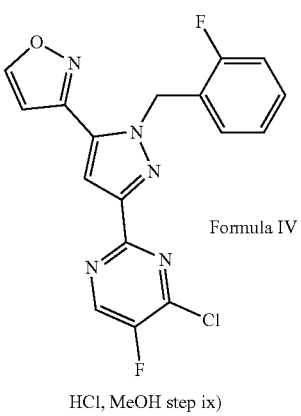

Formula IV step 3) POCl₃ step x)

HCl, MeOH step ix)

(9')

HCl, MeOH step ix)

It has been found that the preparation of compounds of Formula II or Formula IV according to Scheme 4 presents several advantages when compared to their preparation according the Scheme 3. Although the process summarized in Scheme 3 is very short, it is not as amenable to scale up for large scale manufacturing as is Scheme 4. The use of the non-symmetrical reagents (25) and (26), or similar reagents, for the preparation of intermediates (10) or (10'), leads to the formation of a large number of impurities. These impurities need to be separated before the next step is carried out to avoid carrying over into the final product. This involves lengthy and complex purifications and low yields.

The processes summarized in Scheme 4, which utilize as a first step the reaction of a symmetrical reagent (27), have the advantage of providing symmetrical intermediate (6) or (6') in high purity and yields. This intermediate can then be converted to a compound of Formula II or of Formula IV by several alternative processes: through a 5-step process with steps vi) to x); through a one-step process directly to the final product or through a four-step process with steps vi) and 1) to 3). In all cases, each of the resulting steps is high yielding and the intermediates are all isolated in high purity and yield after simple precipitations or crystallizations, avoiding the use of chromatography. The overall process is thus highly efficient and amenable to scale up for large scale manufacturing.

Herein described is also a novel process for the preparation of compounds of Formula III, Formula V, Formula VI or Compound I, using intermediate (7) or intermediate (7'), which are themselves generated from intermediates (6) and (6'). The process is summarized in Scheme 5 below. The process is exemplified for the preparation of a compound of Formula V below. Analogous processes would be used for the preparation of compounds of Formula III and VI, as well as Compound I.

Scheme 5

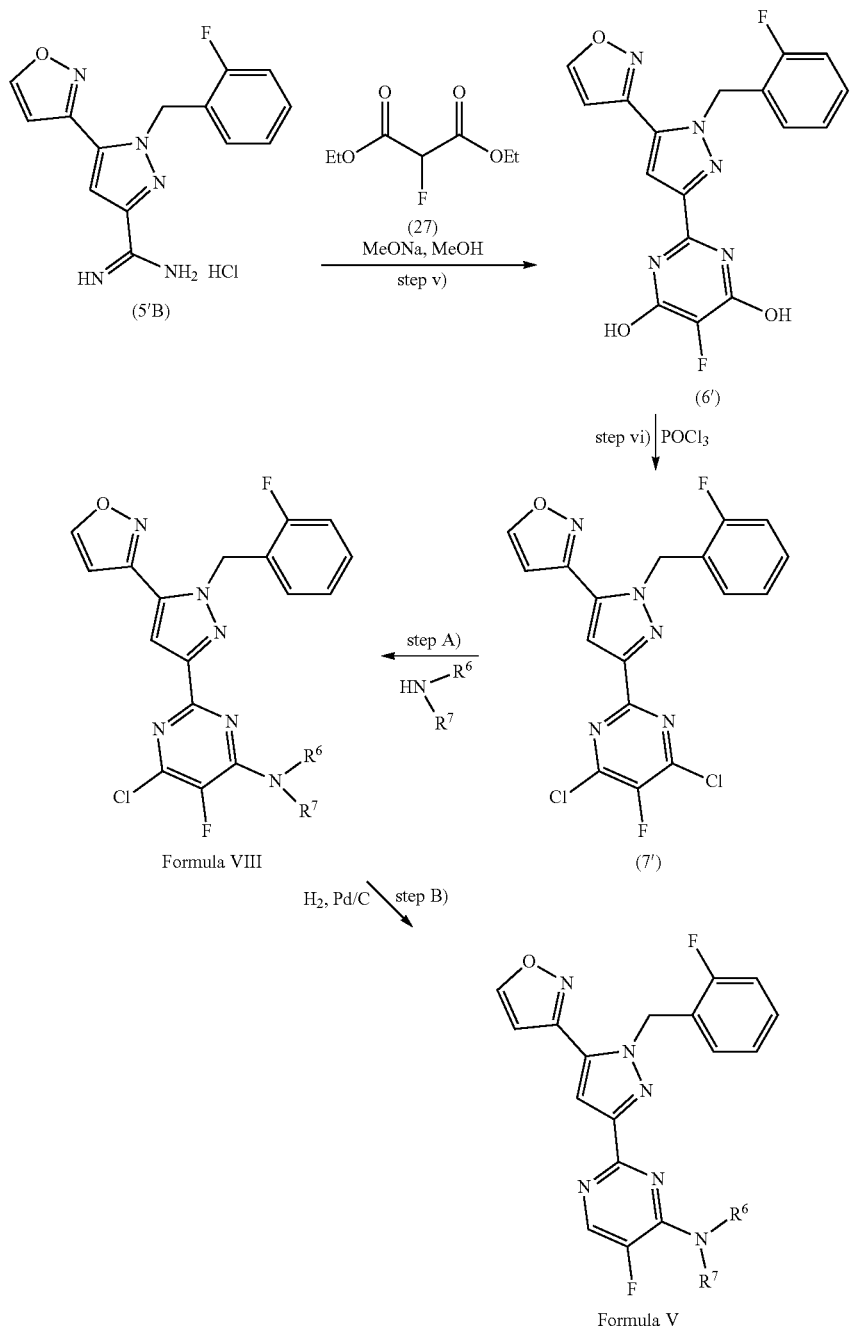

This process is advantageous over alternative processes to generate compounds of Formula III, Formula V, Formula VI and Compound I in that it uses the symmetrical intermediate (7) or (7') as the starting material. Starting from this symmetrical intermediate, generated from symmetrical intermediates (6) and (6'), as discussed above, results in overall high yields and purities of the subsequent steps. Two high yielding steps yield the final Formula V amine. The overall process is amenable to scale-up for large scale manufacturing.

Several processes for the preparation of compounds of Formula VI, Compound I, Compound IA and Compound IB were previously described in WO2014144100. In that publication, enantiomerically pure Compound IA and Compound IB were obtained after chiral resolution of the corresponding racemic mixture Compound I, by using chiral liquid chromatography. Compounds of Formula VI and Compound I could be prepared by reaction of an intermediate of Formula II or an intermediate of Formula IV with the corresponding racemic amine (14). Racemic amine (14) was prepared according to Scheme 6 below, from a compound (17), which is commercially available, via the formation of an intermediate epoxide that was isolated but not purified before the next amination step.

Scheme 6

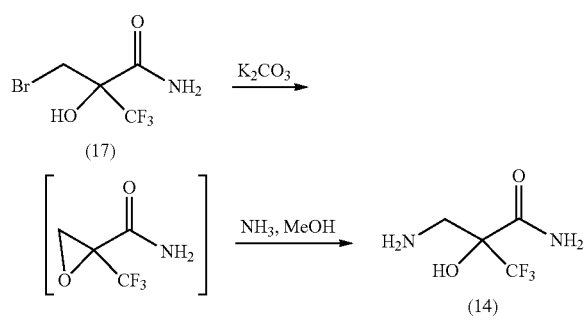

Herein described are several novel alternative pathways for the preparation of compounds of Formula VI, Compound I, Compound IA and Compound IB from intermediates Formula IV or (7'). These are summarized in Scheme 7 below, as exemplified for Compound IA. These pathways offer several advantages over the previously described ones.

The epoxide intermediate of scheme 5 is a known genotoxic impurity that therefore requires special treatment by the Food and Drug Administration (FDA) and potentially other regulatory authorities. A process that avoids the use of this intermediate is therefore desirable if the final product (e.g. Compound I or Compound IA) is going to be used in human clinical trials.

The processes summarized in Scheme 6 avoid the formation of such intermediate by preparing amine (14) directly from intermediate (17) in one single step. Intermediate (17) is prepared in large scale from readily available starting material (15) using known procedures.

Scheme 7

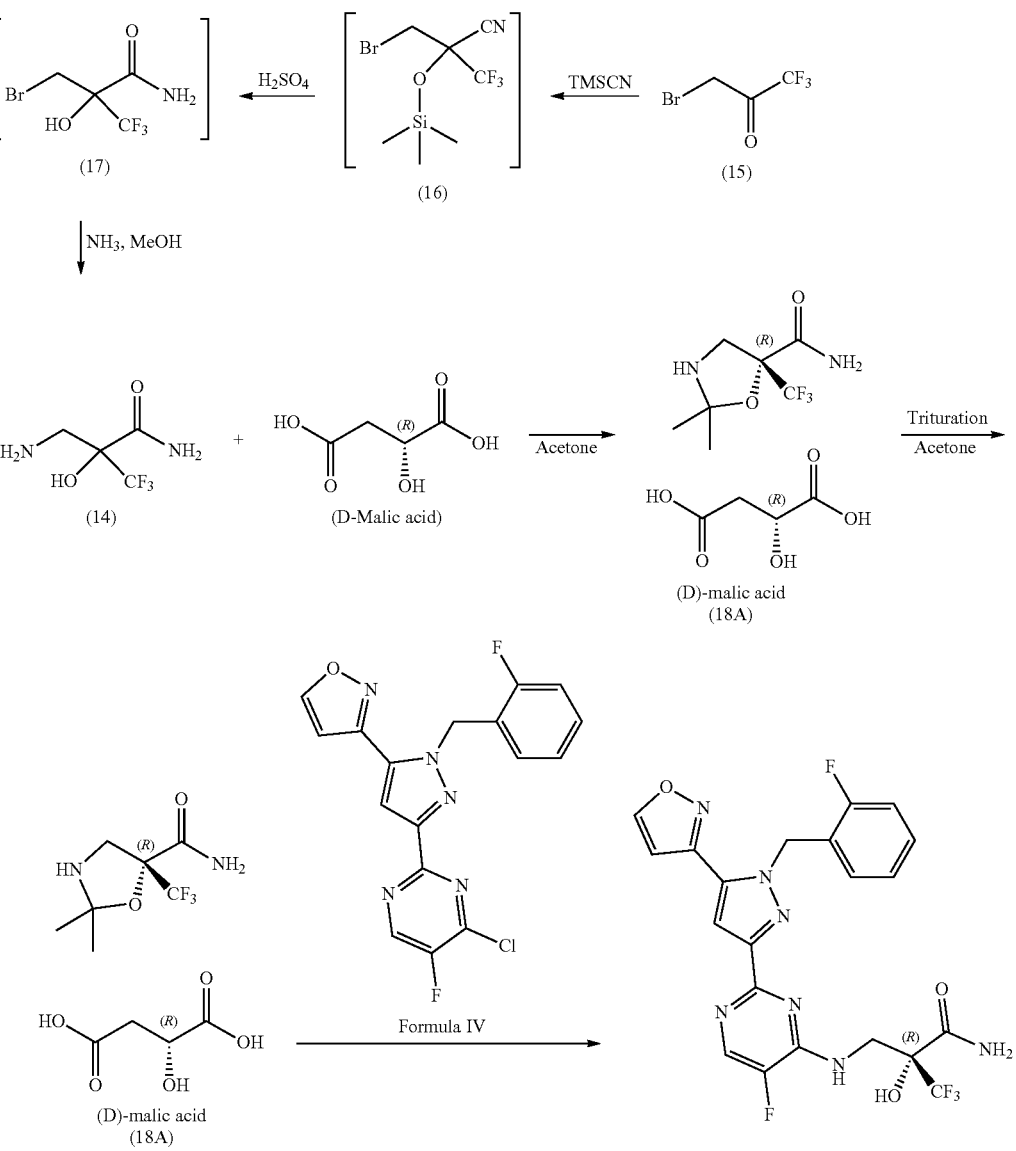

-continued

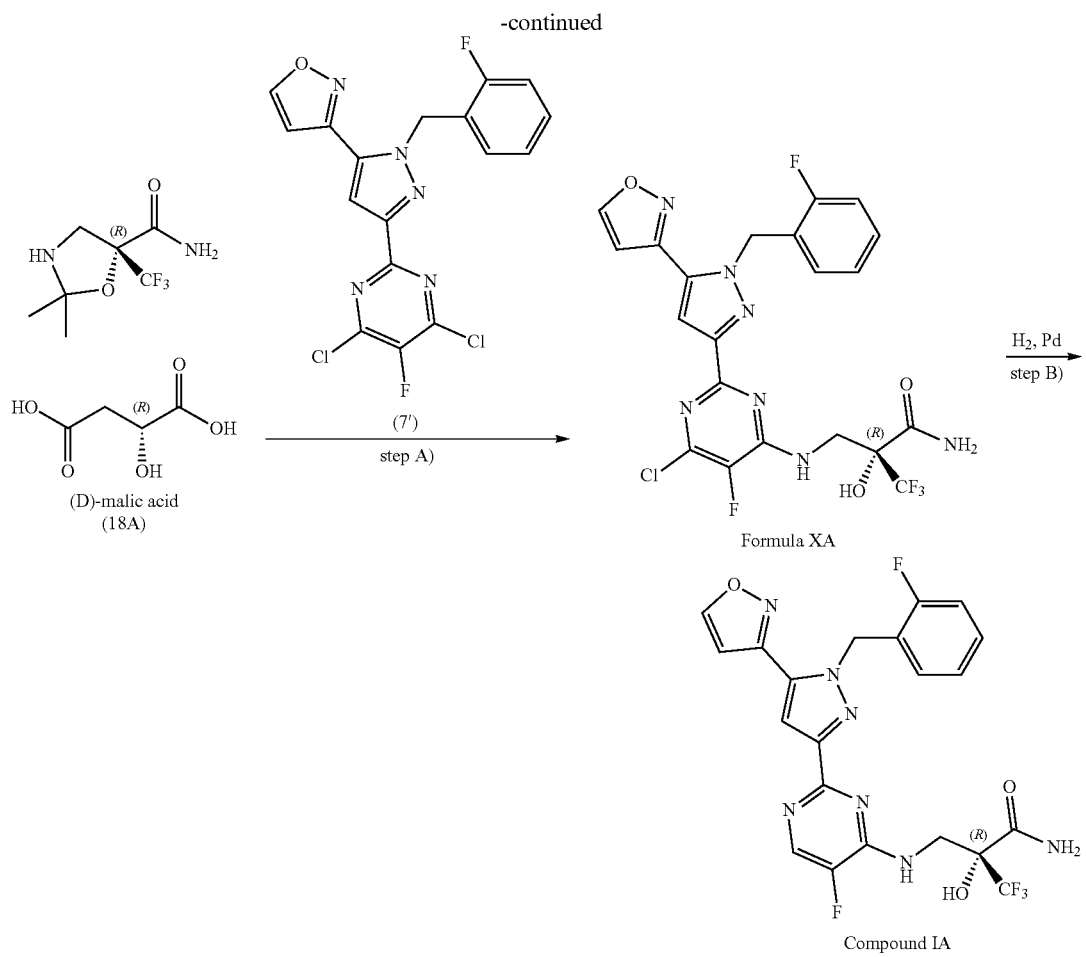

The processes summarized in Scheme 7 use a chiral amine for the coupling with the intermediates of Formula IV or (7') rather than the racemic mixture (14). This avoids the need for a chiral separation of the two enantiomers of Compound I or Formula VI that would be formed if the racemic amine (14) was used. This also makes the process much more efficient, in particular when only one of the two enantiomers is desired, as it minimizes the waste of intermediates of Formula IV or (7'), which are expensive and lengthy to make in large scale.

It has been found, unexpectedly, that reacting racemic amine (14) with (D)-malic acid in acetone leads to the formation of a previously unknown diastereomeric 1:1 salt of (18A) and (D)-malic acid. This salt precipitated out of solution, leaving the unwanted amine enantiomer (14B) dissolved, providing an easy means to separate the two enantiomers of the amine before their reaction with the expensive intermediate of Formula IV or (7'). Similarly, when the racemic amine (14) was reacted with (L)-malic acid in ketone, only previously unknown diastereomeric 1:1 salt of novel intermediate (18B) and (L)-malic acid precipitated out of solution, leaving the undesired amine enantiomer (14A) in solution. The chiral salts of (18A) or (18B) thus obtained can then be heated in solution, liberating the chiral desired amines with loss of acetone before being used in the subsequent coupling step.

Herein described is the chiral preparation of Compound IA and Compound IB by using the corresponding enantiomerically pure amines (14A) and (14B), which are chirally resolved before their reaction with intermediates Novel intermediates that are useful in the processes here described are also disclosed.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

As used herein, the terms "comprising", "has", "including", "containing", and other grammatical variants thereof encompass the terms "consisting of" and "consisting essentially of."

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

All publications cited in this specification are herein incorporated by reference as if each individual publication were specifically and individually indicated to be incorporated by reference herein as though fully set forth.

Subject matter incorporated by reference is not considered to be an alternative to any claim limitations, unless otherwise explicitly indicated.

Where one or more ranges are referred to throughout this specification, each range is intended to be a shorthand format for presenting information, where the range is understood to encompass each discrete point within the range as if the same were fully set forth herein.

While several aspects and embodiments of the present invention have been described and depicted herein, alternative aspects and embodiments may be affected by those skilled in the art to accomplish the same objectives. Accordingly, this disclosure and the appended claims are intended to cover all such further and alternative aspects and embodiments as fall within the true spirit and scope of the invention.

EXAMPLES

The following preparative examples are set forth in order that this invention is more fully understood. These examples are for the purpose of illustration only and are not to be construed as limiting the scope of the invention in any way.

Methods
HPLC Analysis
Equipment:
- A. HPLC analyses were conducted using an Agilent 1100/1200 series HPLC system consisting of pump, ChemStation UV VWD or DAD detector, auto injector, and column heater, or equivalent. ChemStation Software installed on GX270 or equivalent. Column was HALO C18 150×4.6 mm
- B. Column: HALO C18 150×4.6 mm 2.7 micron or equivalent
- C. Auto-sampler vials, silicon/Teflon septa, 12×32 mm
- D. 100-mL class A volumetric flasks
- E. Weighing funnels
- F. Spatulas
- G. Disposable glass Pasteur pipettes
- H. Balance capable of accurately weighing 0.01 mg
- I. 2×2-L solvent reservoir Reagents:
- A. Water, HPLC grade or equivalent
- B. Acetonitrile (ACN), HPLC grade, or equivalent
- C. Trifluoroacetic acid (TFA) HPLC grade or equivalent
- D. Intermediate test sample.
- E. Intermediate authentic materials or reference standard if available.

Solvent and Diluent:
- A. Solvent A: 0.1% TFA in water (i.e. 1 mL in 1 L of water)
- B. Solvent B: 0.1% TFA in acetonitrile (i.e. 1 mL in 1 L of ACN)
- C. Diluent: acetonitrile/water Column Temperature: 40° C.
Time Table:

| Time (minute) | % Solvent A | % Solvent B |
|---|---|---|
| 0 | 85 | 15 |
| 10 | 5 | 95 |
| 15 | 5 | 95 |

Retention Times of Selected Compounds:
Retention Times of Selected Compounds:

| Compound | Approximate Retention Time (Min) |
|---|---|
| Isooxazole-3-carboxylic acid (1') | 1.8 |
| Compound (2') | 3.1 |
| Compound (3') | 6.2 |
| Compound (4') | 8.6 |
| Compound (5') | 5.1 |
| Compound (6') | 6.2 |
| Compound (7') | 10.3 |
| Compound (8') | 10.0 |
| Compound (9') | 8.8 |
| Compound (10') | 7.0 |
| Formula IV | 9.3 |
| Compound I | 8.9 |

Nuclear Magnetic Resonance Spectroscopy $^1$H NMR spectra of all compounds were recorded on a BRUKER NMR spectrometer operating at 500 MHz at room temperature. Samples dissolved in CDCl$_3$ were referenced relative to residual solvent peak at 7.27 ppm. Samples dissolved in DMSO-d$_6$ were referenced relative to the residual solvent peak at 2.50 ppm. The resulting FIDs were transferred to a PC and processed using ACD/Labs NMR processing software.

Example 1 i): Coupling of Compound (1') and N,O-Dimethylhydroxylamine to Provide N-methoxy-N-methyl-isoxazole-3-carboxamide (2')

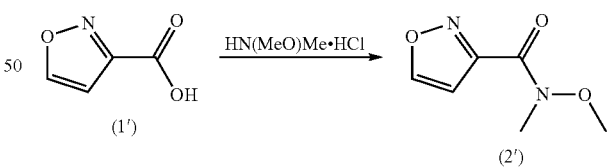

Isooxazole-3-carboxylic acid ((1'), 241.6 g, 2137 mmoles, 1.0 equiv.), toluene (1450 mL) and DMF (7.8 g, 107 mmoles, 0.05 equiv.) were charged to a suitable reaction vessel equipped with a mechanical stirrer and a digital thermometer. The resulting slurry was heated to 45-50° C. Oxalyl chloride (325 g, 2559 mmoles, 1.2 equiv.) was then charged via an addition funnel over the course of 2 h while maintaining the reaction temperature between 45 to 50° C. and a vigorous gas evolution was observed. A brown mixture was obtained after addition. The brown mixture was heated to 87 to 92° C. over 1 h and stirred at 87 to 92° C. for 1 h. The reaction was completed by HPLC. During heating, the brown mixture turned into a dark solution. The reaction was monitored by quenching a portion of the reaction mixture into piperidine and monitoring the piperidine amide by HPLC. The dark mixture was cooled to 20-25° C. and then filtered through a sintered glass funnel to remove any insolubles. The dark filtrate was concentrated under reduced pressure to a volume of 400 mL dark oil.

Potassium carbonate (413 g, 2988 mmoles, 1.4 equiv.) and water (1000 mL) were charged to a suitable reaction vessel equipped with a mechanical stirrer and a digital thermometer. The reaction solution was cooled to −10 to −5° C. N,O-dimethylhydroxyamine hydrochloride (229 g, 2348 mmoles, 1.1 equiv.) was charged to a suitable reaction vessel and dissolved in water (1000 mL). The N,O-dimethylhydroxyamine solution and dichloromethane (2500 mL) were then charged to the potassium carbonate solution.

The above dark oil (400 mL) was then charged slowly via an addition funnel while maintaining the reaction temperature −10 to 0° C. The addition was slightly exothermic and a brown mixture was obtained after addition. The mixture was stirred at 0 to 5° C. over 20 min. and then warmed to 20 to 25° C. The bottom organic layer was collected and the top aq. layer was extracted with dichloromethane (400 mL). The combined organic layers were washed with 15% sodium chloride solution (1200 mL). The organic layer was dried over magnesium sulfate and then filtered. The filtrate was concentrated under reduced pressure to give intermediate (2') as a dark oil (261.9 g, 97 wt %, 76% yield, 3 wt % toluene by $^1$H-NMR, 0.04 wt % water content by KF). $^1$H-NMR (500 MHz, CDCl$_3$) δ ppm 8.48 (s, 1H); 6.71 (s, 1H); 3.78 (s, 3H); 3.38 (s, 3H).

ii): Alkylation of Compound (2') and ethyl propiolate to Provide (E)-ethyl 4-(isoxazol-3-yl)-2-(methoxy(methyl)amino)-4-oxobut-2-enoate (3')

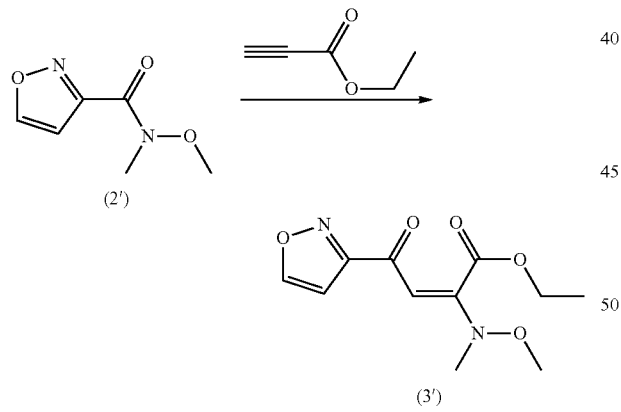

Intermediate (2') (72.2 g, 96 wt %, 444 mmoles, 1.0 equiv.), ethyl propiolate (65.7 g, 670 mmoles, 1.5 equiv.) and anhydrous THF (650 mL) were charged to a suitable reaction vessel equipped with a mechanical stirrer and a digital thermometer. The solution was cooled to −65 to −55° C. Sodium bis(trimethylsilyl)amide in THF (1 M, 650 mL, 650 mmoles, 1.46 equiv.) was then charged slowly via an addition funnel while maintaining the reaction temperature −65 to −55° C. The mixture was stirred below −55° C. over 10 min. after addition was complete. Then 1 N HCl (650 mL, 650 mmoles, 1.46 equiv.) was charged to quench the reaction while maintaining the reaction temperature below −20° C. followed immediately with the addition of ethyl acetate (1500 mL) and water (650 mL). The top ethyl acetate layer was collected and the bottom aqueous layer was extracted with ethyl acetate (800 mL). The combined organic layers were washed with 10% citric acid (1000 mL) and saturated sodium chloride solution (650 mL). The organic layer was concentrated under reduced pressure to give a dark oil.

The dark oil was dissolved in a solution of dichloromethane/ethyl acetate/heptane (150 mL/100 mL/100 mL). The solution was loaded on a silica pad (410 g) and the silica pad was eluted with ethyl acetate/heptane (1/1 v/v). The filtrate (~3000 mL) was collected and then concentrated under reduced pressure to a volume of 150 mL to give a slurry upon standing. Heptane (200 mL) was then added to the slurry and the slurry was concentrated under reduced pressure to a volume of 150 mL. The resulting slurry was filtered, and the filter cake was washed with heptane (150 mL). The filter cake was then air dried overnight to furnish intermediate (3') as a brown solid (63.4 g, 56% yield, >99% pure by HPLC). $^1$H-NMR (500 MHz, CDCl$_3$) δ ppm 8.42 (d, J=1.53 Hz, 1H); 6.76 (d, J=1.53 Hz, 1H); 6.18 (s, 1H); 4.47 (q, J=7.07 Hz, 2H); 3.75 (s, 3H); 3.21 (s, 3H); 1.41 (t, J=7.17 Hz, 3H).

iii): Cyclization of Compound 3' and 2-fluorobenzylhydrazine to Provide ethyl 1-(2-fluorobenzyl)-5-(isoxazol-3-yl)-1H-pyrazole-3-carboxylate (4')

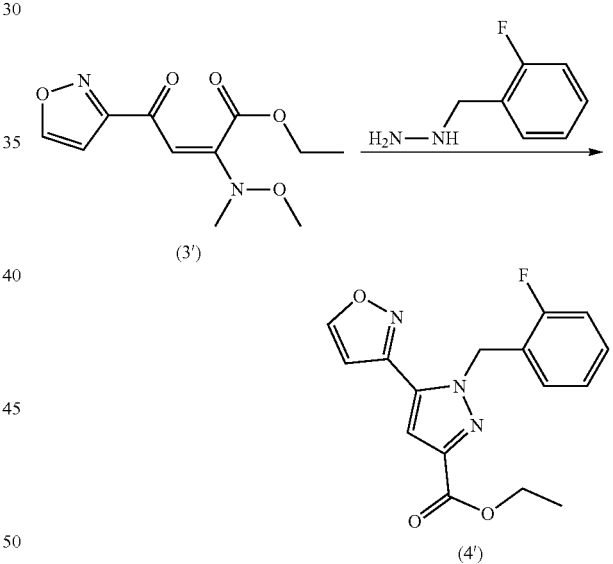

Intermediate (3') (72.9 g, 287 mmoles, 1.0 equiv.) and absolute ethanol (730 mL) were charged to a suitable reaction vessel equipped with a mechanical stirrer and a digital thermometer. The mixture was cooled to 0 to 5° C. 2-Fluorobenzylhydrazine (48.2 g, 344 mmoles, 1.2 equiv.) was then charged to the mixture. The mixture was stirred at 0 to 10° C. over 1 h and then warmed to 20 to 25° C. and stirred at 20 to 25° C. over 16 h. The reaction was completed by HPLC. Concentrated HCl (33.9 g, 37 wt %, 344 mmoles, 1.2 equiv.) was charged to the reaction mixture over 1 min and the batch temperature exothermed from 20° C. to 38° C. A slurry was obtained. The mixture was cooled to 0 to 10° C. over 1 h and stirred at 0-10° C. for 1 h. The resulting slurry was filtered, and the filter cake was washed with ethanol (200 mL). The filter cake was dried under vacuum at 30 to 40° C. over 16 h to furnish intermediate (4') as an off-white solid (81.3 g, 90% yield, >99% pure by HPLC). $^1$H-NMR (500 MHz, CDCl$_3$) δ ppm 8.47 (d, J=1.68 Hz, 1H); 7.15-7.26 (m, 2H); 6.94-7.08 (m, 2H); 6.77-6.87 (m, 1H); 6.55 (d, J=1.68 Hz, 1H); 5.95 (s, 2H); 4.43 (q, J=7.02 Hz, 2H); 1.41 (t, J=7.17 Hz, 3H).

iv): Amination of Compound (4') to Provide 1-(2-fluorobenzyl)-5-(isoxazol-3-yl)-1H-pyrazole-3-carboximidamide hydrochloride (5')

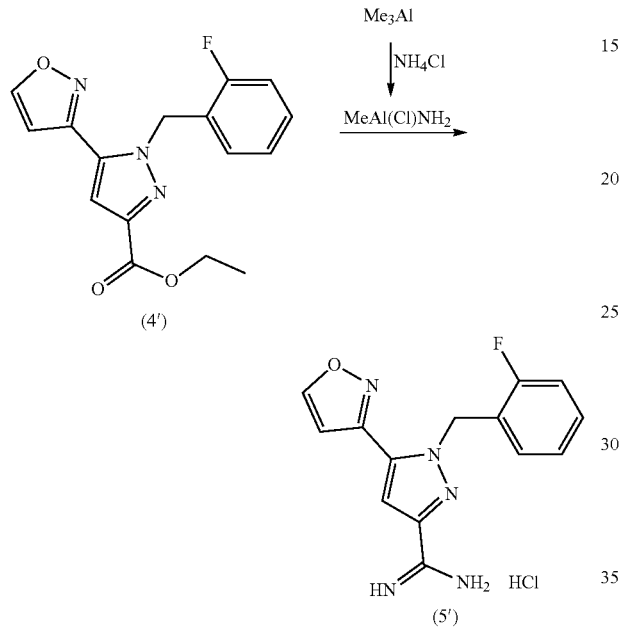

Anhydrous ammonium chloride (267 g, 4991 mmoles, 5.0 equiv.) and toluene (5400 mL) were charged to a suitable reaction vessel equipped with a mechanical stirrer and a digital thermometer. Trimethylaluminum in toluene (2 M, 2400 mL, 4800 mmoles, 4.8 equiv.) was charged slowly via an addition funnel while maintaining the reaction temperature at 20 to 40° C. (Note: Methane gas evolution was observed during addition). Then the mixture was heated to 75 to 80° C. over 30 min. and a clear white solution was obtained. Intermediate (4') (315 g, 999 mmoles, 1.0 equiv.) was charged to reaction mixture in four equal portions over 1 h at 75 to 90° C. The reaction was stirred at 80 to 90° C. over 30 min. and then heated to 100 to 110° C. and stirred at 100 to 110° C. over 3 h. The reaction was completed by HPLC. The reaction mixture was cooled to 10 to 20° C. and methanol (461 g, 14.4 moles, 14.4 equiv.) was charged slowly via an addition funnel while maintaining the reaction temperature 10-40° C. (Note: the quenching was very exothermic and a lot gas evolution was observed). A thick slurry was obtained. A 3N HCl (6400 mL, 3 N, 19.2 moles, 19.2 equiv.) was then charged slowly via an addition funnel while maintaining the reaction temperature at 20 to 45° C. The mixture was heated to 80 to 85° C. and stirred at 80 to 85° C. over 10 min. to obtain a clear biphasic mixture. The mixture was cooled to 0 to 5° C. over 3 h and stirred at 0 to 5° C. over 1 h. The resulting slurry was filtered, and the filter cake was washed with water (3000 mL). The filter cake was dried under vacuum at 40 to 50° C. over 24 h to furnish intermediate (5') as an off-white solid (292 g, 91% yield, >99% pure by HPLC). $^1$H-NMR (500 MHz, DMSO-d$_6$) δ ppm 9.52 (s, 2H); 9.33 (s, 2H); 9.18 (d, J=1.53 Hz, 1H); 7.88 (s, 1H); 7.29-7.38 (m, 1H); 7.19-7.25 (m, 1H); 7.10-7.16 (m, 1H); 7.03 (d, J=1.53 Hz, 1H); 6.92-6.98 (m, 1H); 5.91 (s, 2H). M.P. 180-185° C.

v): Cyclization of Compound (5') and diethyl fluoromalonate to Provide 5-fluoro-2-(1-(2-fluorobenzyl)-5-(isoxazol-3-yl)-1H-pyrazol-3-yl)pyrimidine-4,6-diol (6')

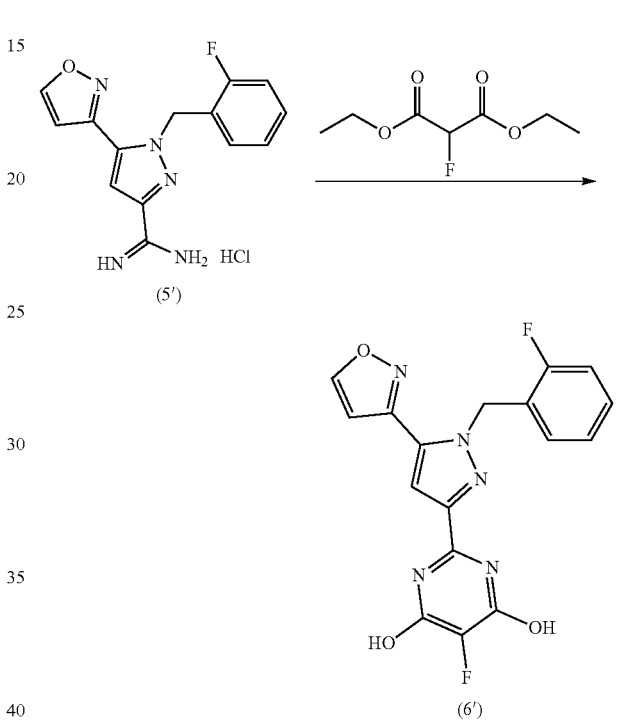

Intermediate (5') (224.6 g, 698 mmoles, 1.0 equiv.), methanol (2250 mL) and diethyl fluoromalonate (187 g, 1050 mmoles, 1.5 equiv.) were charged to a suitable reaction vessel equipped with a mechanical stirrer and a digital thermometer. Then sodium methoxide in methanol solution (567 g, 30 wt %, 3149 mmoles, 4.5 equiv.) was charged via an addition funnel while maintaining the reaction temperature 20 to 35° C. The mixture was stirred at 20 to 35° C. over 30 min. and a light suspension was obtained. The reaction was completed by HPLC. A solution of 1.5 N HCl (2300 mL, 3450 mmoles, 4.9 equiv.) was charged via an addition funnel over 1 h while maintaining the reaction temperature 20 to 30° C. A white suspension was obtained. The pH of the reaction mixture was to be −1 by pH paper. The slurry was stirred at 20 to 30° C. over 30 min. The resulting slurry was filtered, and the filter cake was washed with a pre-mixed solution of methanol and water (500 mL/500 mL), and then with water (1000 mL). The filter cake was dried under vacuum at 50 to 60° C. over 16 h to furnish intermediate (6') as an off-white solid (264 g, 97% yield, >99% pure by HPLC). $^1$H-NMR (500 MHz, DMSO-d$_6$) δ ppm 12.82 (br. s., 1H); 12.31 (br. s., 1H); 9.14 (d, J=1.53 Hz, 1H); 7.55 (s, 1H); 7.31-7.37 (m, 1H); 7.18-7.25 (m, 1H); 7.10-7.15 (m, 2H); 6.97-7.02 (t, J=7.55 Hz, 1H); 5.88 (s, 2H).

vi): Chlorination of Compound (6') to Provide 3-(3-(4,6-dichloro-5-fluoropyrimidin-2-yl)-1-(2-fluorobenzyl)-1H-pyrazol-5-yl)isoxazole (7')

vii): Substitution of Compound (7') with Methoxide to Provide 3-(3-(4-chloro-5-fluoro-6-methoxypyrimidin-2-yl)-1-(2-fluorobenzyl)-1H-pyrazol-5-yl)isoxazole (8')

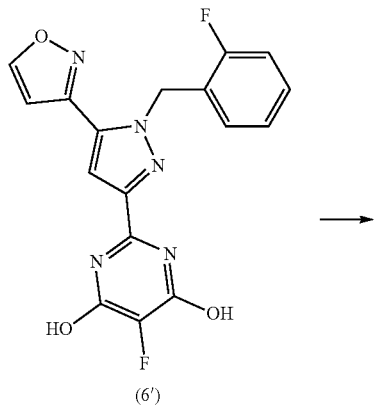

(6')

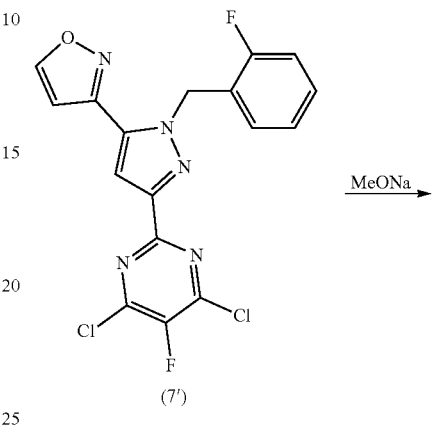

(7')

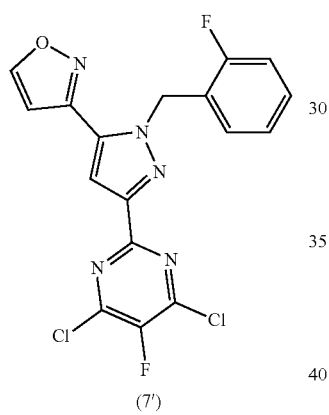

(7')

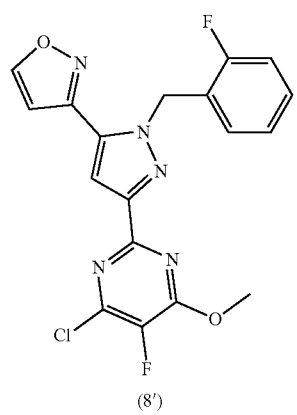

(8')

Intermediate (6') (264 g, 711 mmoles, 1.0 equiv.), acetonitrile (4000 mL) and N,N-dimethylaniline (138 g, 1137 mmoles, 1.6 equiv.) were charged to a suitable reaction vessel equipped with a mechanical stirrer and a digital thermometer. The slurry mixture was heated to 70-80° C. Then phosphorous oxychloride (655 g, 4270 mmoles, 6.0 equiv.) was charged via an addition funnel over 1 h while maintaining the reaction temperature 70 to 80° C. The mixture was stirred at 75 to 80° C. over 22 h and a brown solution was obtained. The reaction was completed by HPLC. Then the mixture was cooled to between 0 and 5° C. and cotton like solids precipitated out at 25° C. Water (3000 mL) was charged slowly via an addition funnel while maintaining the reaction temperature at 0 to 10° C. The slurry was stirred at 0 to 10° C. over 30 min. The resulting slurry was filtered, and the filter cake was washed with a pre-mixed solution of acetonitrile and water (500 mL/500 mL). The filter cake was dried under vacuum at 35 to 45° C. over 16 h to furnish intermediate (7') as an off-white solid (283 g, 98% yield, >99% pure by HPLC). $^1$H-NMR (500 MHz, CDCl$_3$) δ ppm 8.48 (d, J=1.68 Hz, 1H); 7.44 (s, 1H); 7.19-7.25 (m, 1H); 6.96-7.08 (m, 2H); 6.81-6.88 (m, 1H); 6.60 (d, J=1.68 Hz, 1H); 6.03 (s, 2H).

Methanol (3400 mL) and sodium methoxide in methanol (154 mL, 5.4 M, 832 mmoles, 1.2 equiv.) were charged to a suitable reaction vessel equipped with a mechanical stirrer and a digital thermometer. The reaction mixture was heated to 23 to 27° C. Intermediate (7') (283 g, 693 mmoles, 1.0 equiv.) was charged to the mixture in small portions (5-10 g each portion) over 40 min while maintaining the reaction temperature 23 to 27° C. The slurry was stirred at 23 to 27° C. over 30 min. The reaction was completed by HPLC. The resulting slurry was filtered, and the filter cake was washed with methanol (850 mL) and then water (850 mL). The filter cake was dried under vacuum at 35 to 45° C. over 16 h to furnish intermediate (8') as an off-white solid (277 g, 99% yield, 97% pure by HPLC). $^1$H-NMR (500 MHz, CDCl$_3$) δ ppm 8.47 (d, J=1.83 Hz, 1H); 7.38 (s, 1H); 7.18-7.25 (m, 1H); 7.01-7.08 (m, 1H); 6.94-7.00 (m, 1H); 6.81-6.88 (m, 1H); 6.60 (d, J=1.68 Hz, 1H); 6.00 (s, 2H); 4.21 (s, 3H).

viii): Hydrogenation of Compound (8') to Provide 3-(3-(5-fluoro-4-methoxypyrimidin-2-yl)-1-(2-fluorobenzyl)-1H-pyrazol-5-yl)isoxazole (9')

ix): Demethylation of Compound (9') to Provide 5-fluoro-2-(1-(2-fluorobenzyl)-5-(isoxazol-3-yl)-1H-pyrazol-3-yl)pyrimidin-4-ol (10')

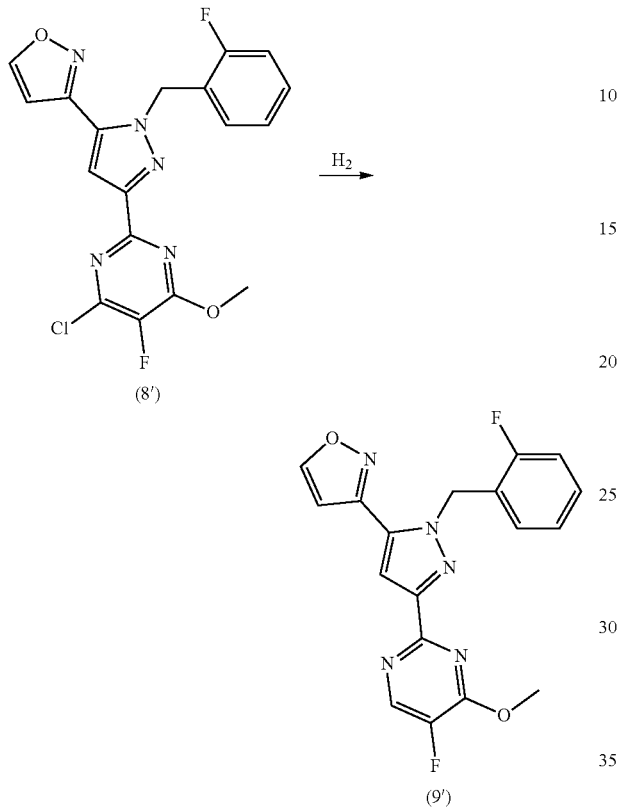

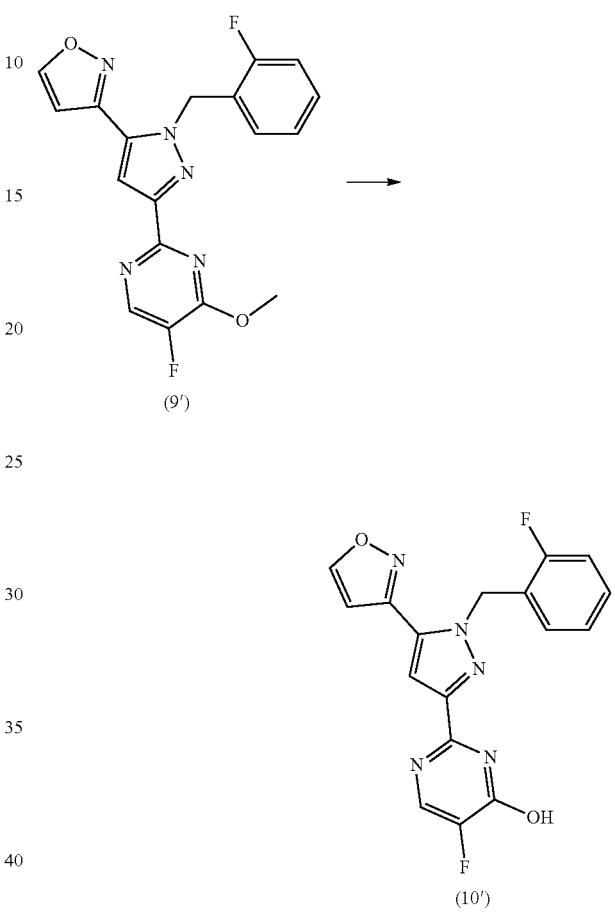

Intermediate (8') (226 g, 560 mmoles, 1.0 equiv.), palladium (10% on activated carbon, nominally 50% water wet, 22.6 g, 0.01 moles, 0.018 equiv), tetrahydrofuran (3400 mL) and triethylamine (91 g, 897 mmoles, 1.6 equiv.) were charged to a suitable reaction vessel equipped with a mechanical stirrer and a digital thermometer. Nitrogen was bubbled into the reaction mixture via teflon tubing over 10 min. at 20 to 30° C. Then the mixture was heated to 40 to 50° C. and hydrogen gas was bubbled into the reaction mixture via teflon tubing over 6 h while maintaining the reaction temperature 40 to 50° C. The reaction was completed by HPLC. Nitrogen was then bubbled into the reaction mixture via teflon tubing over 10 min. at 40 to 50° C. The reaction mixture was hot filtered through Hypo Supercel™ and the filter cake was washed with tetrahydrofuran (2000 mL). The filtrate was concentrated under reduced pressure to a volume of ~1300 mL to give a slurry. Tetrahydrofuran was then solvent exchanged to methanol under reduced pressure via continuously feeding methanol (3000 mL). The final volume after solvent exchange was 1300 mL. The resulting slurry was filtered, and the filter cake was washed with methanol (500 mL). The filter cake was dried under vacuum at 20 to 25° C. over 16 h to furnish intermediate (9') as a white solid (192 g, 93% yield, 98% pure by HPLC). $^1$H-NMR (500 MHz, CDCl$_3$) δ ppm 8.47 (d, J=1.68 Hz, 1H); 8.41 (d, J=2.59 Hz, 1H); 7.36 (s, 1H); 7.17-7.24 (m, 1H); 6.95-7.07 (m, 2H); 6.83-6.90 (m, 1H); 6.60 (d, J=1.68 Hz, 1H); 5.99 (s, 2H); 4.19 (s, 3H).

Intermediate (9') (230 g, 623 mmoles, 1.0 equiv.), MeOH (3450 mL) and conc. HCl (307 g, 37 wt %, 3117 mmoles, 5.0 equiv.) were charged to a suitable reaction vessel equipped with a mechanical stirrer and a digital thermometer. The mixture was heated to 60 to 65° C. and a solution was obtained. The mixture was then stirred at 60 to 65° C. over 17 h and a slurry was obtained. The reaction was completed by HPLC. The slurry was cooled to 20 to 25° C. over 2 h and stirred at 20 to 25° C. over 30 min. The resulting slurry was filtered, and the filter cake was washed with methanol (1000 mL). The filter cake was dried under vacuum at 35 to 45° C. over 16 h to furnish intermediate (10') as a white solid (214 g, 97% yield, >99% pure by HPLC). $^1$H-NMR (500 MHz, DMSO-d$_6$) δ ppm 12.90-13.61 (br. s., 1H); 9.11 (d, J=1.68 Hz, 1H); 8.16 (s, 1H); 7.64 (s, 1H); 7.29-7.42 (m, 1H); 7.17-7.28 (m, 2H); 7.08-7.15 (m, 1H); 6.97 (s, 1H); 5.91 (s, 3H).

x): Chlorination of Compound (10') to Provide 3-(3-(4-chloro-5-fluoropyrimidin-2-yl)-1-(2-fluorobenzyl)-1H-pyrazol-5-yl)isoxazole (Formula IV)

a): Cyanation of Intermediate (15) to Provide 2-(bromomethyl)-3,3,3-trifluoro-2-((trimethylsilyl)oxy)propanenitrile (16)

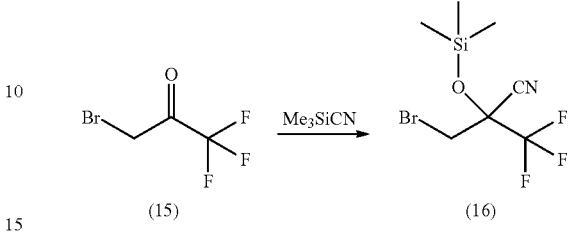

Trimethylsilanecarbonitrile (153 g, 1.54 moles, 0.97 equiv) and triethylamine (4.44 mL, 3.22 g, 0.032 mole, 0.02 equiv) were charged to a suitable reaction vessel equipped with a mechanical stirrer and a digital thermometer. The mixture was cooled to 5° C. 3-Bromo-1,1,1-trifluoropropan-2-one ((15), 304 g, 1.59 moles, 1.0 equiv) was charged via an addition funnel over 35 min, while maintaining the reaction temperature between 10 to 20° C. The mixture was stirred at 20 to 30° C. over 3 h after the addition to furnish intermediate (16) as a dense oil which was used directly in the next step. $^1$H-NMR (500 MHz, CDCl$_3$) δ ppm 3.68 (d, J=11.14 Hz, 1H); 3.57 (d, J=11.14 Hz, 1H), 0.34-0.37 (m, 9H).

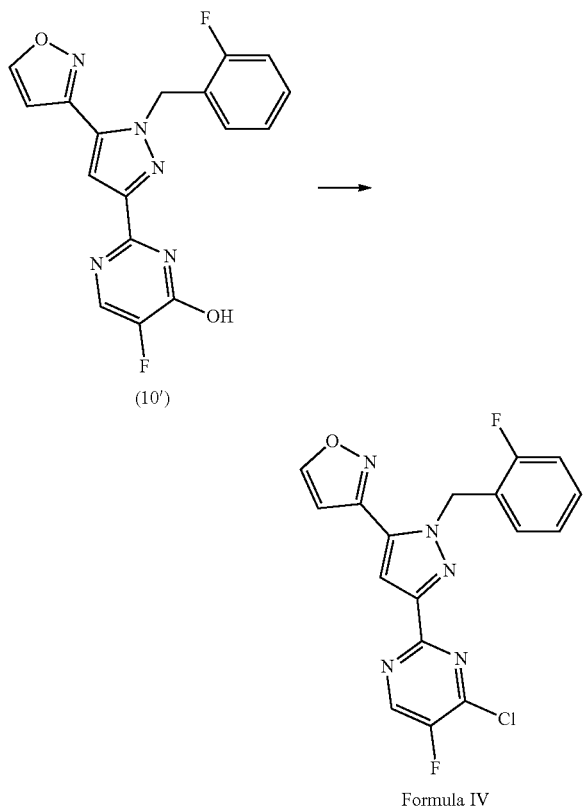

Formula IV

Intermediate (10') (214 g, 602 mmoles, 1.0 equiv.), acetonitrile (3000 mL) and N,N-dimethylaniline (109 g, 899 mmoles, 1.5 equiv.) were charged to a suitable reaction vessel equipped with a mechanical stirrer and a digital thermometer. The slurry mixture was heated to 70 to 80° C. Then phosphorous oxychloride (276 g, 1802 mmoles, 3.0 equiv.) was charged via an addition funnel over 30 min. while maintaining the reaction temperature 70-80° C. The mixture was stirred at 75 to 80° C. over 2 h and a green solution was obtained. The reaction was completed by HPLC. Then the mixture was cooled to 0 to 5° C. Water (1500 mL) was charged slowly via an addition funnel while maintaining the reaction temperature at 0 to 10° C. The slurry was stirred at 0 to 10° C. over 30 min. The resulting slurry was filtered, and the filter cake was washed with a pre-mixed solution of acetonitrile and water (500 mL/500 mL) and water (500 mL). The filter cake was dried under vacuum at 30 to 40° C. over 16 h to furnish intermediate of Formula IV as an off-white to pink solid (214 g, 95% yield, >99% pure by HPLC). $^1$H NMR (500 MHz, CDCl$_3$) δ ppm 8.65 (s, 1H); 8.48 (d, J=1.68 Hz, 1H); 7.44 (s, 1H); 7.21-7.25 (m, 1H); 6.97-7.06 (m, 2H); 6.83-6.87 (m, 1H); 6.61 (d, J=1.68 Hz, 1H); 6.03 (s, 2H).

b): Conversion of Nitrile Compound (16) to Amide to Provide 2-(bromomethyl)-3,3,3-trifluoro-2-hydroxypropanamide (17)

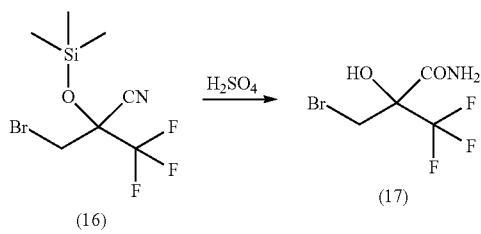

Concentrated sulfuric acid (339 mL, 6.37 moles, 4.0 equiv) was stirred in a suitable reaction vessel equipped with a mechanical stirrer, digital thermometer and an addition funnel. The sulfuric acid was heated to 45° C. The above intermediate (16) was added via an addition funnel over 50 min, while keeping the temperature below 75° C. The reaction mixture was stirred at 75° C. for 2 h and then allowed to cool to room temperature. $^1$H-NMR indicated reaction complete. The reaction mixture was cooled to −15° C. and diluted with ethyl acetate (1824 mL) via an addition funnel over 45 min (very exothermic), while keeping the temperature between −15 to 5° C. Water (1520 mL) was added slowly via an addition funnel for 1 h 20 min. (very exothermic) between −10 to 0° C. The layers were separated and the organic layer was washed with 15% aqueous sodium chloride solution (1520 mL), 25% aqueous sodium carbonate solution (911 mL) followed by 15% aqueous sodium chloride solution (911 mL). The organic layer was filtered and concentrated under reduced pressure to get 348 g of intermediate (17) as light yellow oil. This oil was dissolved in methanol (1200 mL) and concentrated to furnish 380 g of c): N-Alkylation of Compound (17) to Provide of 2-(aminomethyl)-3,3,3-trifluoro-2-hydroxypropanamide (14)

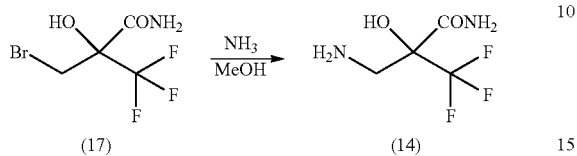

A 7 N solution of ammonia in methanol (600 mL, 4.28 moles, 10 equiv) was charged to a suitable reaction vessel equipped with a mechanical stirrer and a digital thermometer. The solution was cooled to 0 to 5° C. Then the intermediate (17) (102 g, 0.432 moles, 1 equiv) was added via an addition funnel over 30 min at 0 to 5° C. The reaction mixture was warmed to 20 to 25° C. over 1 h and held for 72 h. The reaction was completed by HPLC. The reaction mixture was cooled to 0 to 5° C. and sodium methoxide (78 mL, 5.4 M, 0.421 moles, 0.97 equiv) was added over 2 min. The reaction mixture was then concentrated under reduced pressure to a volume of 300 mL. 2 L of ethyl acetate was added and concentration was continued under reduced pressure to a volume to 700 mL to get a slurry. 700 mL of ethyl acetate was added to the slurry to make the final volume to 1400 mL. 102 mL of water was added and stirred for 2 min to get a biphasic solution. The layers were separated. The ethyl acetate layer was concentrated under reduced pressure to a volume of 600 mL. Then the ethyl acetate layer was heated to >60° C. and heptane (600 mL) was added slowly between 55 to 60° C. The mixture was cooled to 15 to 20° C. to give a slurry. The slurry was stirred at 15 to 20° C. for 2 h and filtered. The solids were dried under vacuum at 25° C. for 16 h to furnish amine (14) as white solid (48 g, 64% yield). $^1$H-NMR (500 MHz, MeOH-$d_4$) δ ppm 2.94 (d, J=13.73 Hz, 1H); 3.24 (d, J=13.58 Hz, 1H).

d): Chiral Resolution of Amine (14) as the 1:1 Salt of (R)-2,2-dimethyl-5-(trifluoromethyl)oxazolidine-5-carboxamide (18A) and (D)-malic acid

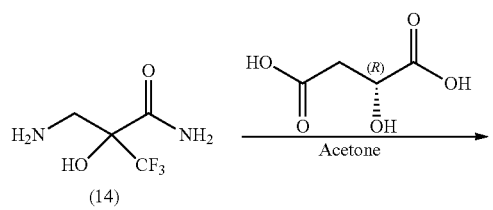

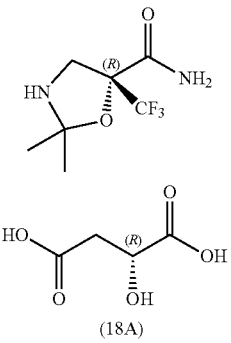

Amine (14) (105 g, 0.608 moles, 1.0 equiv.), (D)-Malic acid (82 g, 0.608 moles, 1.0 equiv.) and acetone (1571 mL) were charged to a suitable reaction vessel equipped with a mechanical stirrer and a digital thermometer. The reaction mixture was stirred at 20 to 25° C. for 16 h. The resulting slurry was filtered, and the wet cake was washed with acetone (300 mL). The wet cake was charged back to the reaction vessel, and acetone (625 mL) was charged. The slurry was heated to 53° C. and held for 6 h. The slurry was cooled to 20 to 25° C. and held at this temperature for 16 h. The slurry was filtered, and the wet cake was washed with acetone (200 mL). The wet cake was dried under vacuum at 40° C. for 4 h to furnish 82.4 g of the 1:1 salt of (18A) and (D)-malic acid as a white solid (82.4 g, 39% yield, 97% ee). $^1$H-NMR (500 MHz, $D_2O$) δ ppm 4.33 (br, s, 1H); 3.61 (br, d, J=13.58 Hz, 1H); 3.40-3.47 (m, 1H); 2.76 (br, d, J=15.87 Hz, 1H); 2.53-2.63 (m, 1H); 2.16 (br, s, 4H).

e): Coupling of the 1:1 (D)-malic Acid Salt of Intermediate (18A) and Formula IV to Provide (R)-3,3,3-trifluoro-2-(4(5-fluoro-2-(1-(2-fluorobenzyl)-5-(isoxazol-3-yl)-1H-pyrazol-3-yl)pyrimidin-4-yl)amino)methyl)-2-hydroxypropanamide (Compound IA)

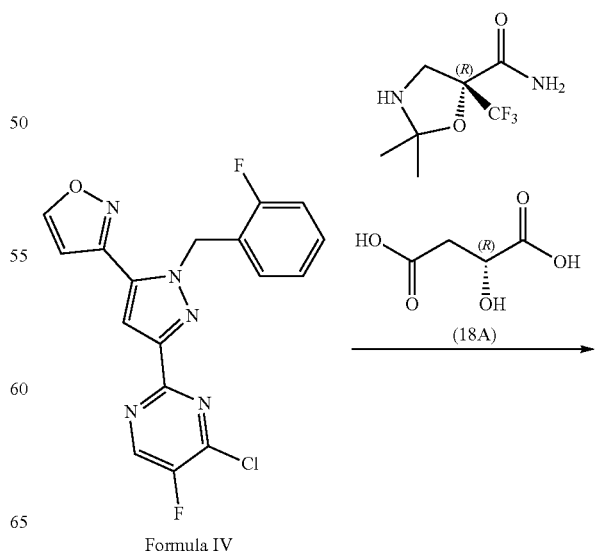

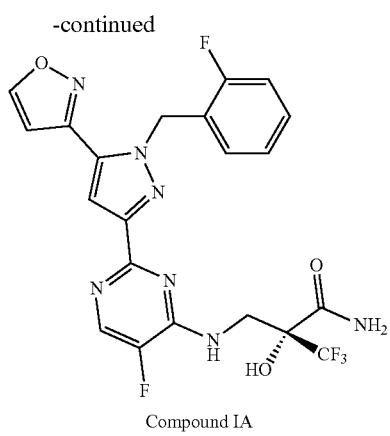

Compound IA

The 1:1 salt of intermediate (18A) and (D)-malic acid (74.1 g, 0.214 moles, 2.5 equiv) and water (44.8 mL) were charged to a suitable reaction vessel equipped with a mechanical stirrer and a digital thermometer. The reaction mixture was heated to 70° C. and stirred for 20 min. Acetone generated during the reaction was removed by blowing with nitrogen. The reaction mixture was cooled to 30 to 40° C. and Formula IV (32 g, 0.086 moles, 1.0 equiv), DMSO (448 mL) and Hunig's base (44.7 mL, 0.257 moles, 3.0 equiv) were charged. The reaction mixture was heated to 90° C. and stirred at 90° C. over 17 h. The reaction was complete by HPLC. Then the mixture was cooled to 60° C. Another portion of Hunig's base (104 mL, 0.599 moles, 7.0 equiv) was charged followed by water (224 mL) at 55 to 62° C. The reaction mixture was stirred for 15 min at 55 to 60° C. to form the seed bed. Water (320 mL) was added via addition funnel at 55 to 62° C. over the course of 30 min, and the resultant slurry was stirred for 1 h at 55 to 60° C. The resulting slurry was filtered, and the filter cake was washed with a pre-mixed solution of methanol and water (320 mL/320 mL) followed by water (640 mL). The filter cake was then dried under vacuum at 40° C. over 16 h to furnish Compound IA as an off-white solid (40 g, 92% yield, 99% pure by HPLC, 98% ee). $^1$H-NMR (500 MHz, DMSO-$d_6$) δ ppm 9.10 (s, 1H); 8.33 (d, J=2.90 Hz, 1H); 7.93 (s, br, 1H); 7.90 (s, 1H); 7.78 (s, br, 1H); 7.69 (s, br, 1H); 7.52 (s, 1H); 7.33 (q, J=7.02 Hz, 1H); 7.17-7.25 (m, 1H); 7.17-7.25 (m, 1H); 7.10 (t, J=7.48 Hz, 1H); 6.98 (t, J=7.55 Hz, 1H); 5.90 (s, 2H); 3.92-4.05 (m, 2H).

Example 2: Kilo-Scale Procedures i): Coupling of Compound (1') and N,O-Dimethylhydroxylamine to Provide N-methoxy-N-methyl-isoxazole-3-carboxamide (2')

Isooxazole-3-carboxylic acid ((1'), 3.857 kg, 34.1 moles, 1.0 equiv.), toluene (19.3 L) and DMF (0.131 L, 1.692 moles, 0.05 equiv.) were mixed in a 30 L jacketed reaction vessel equipped with nitrogen inlet-outlet, overhead stirrer, a thermocouple and an addition funnel. The resulting slurry was heated to 45 to 55° C. Oxalyl chloride (4.8 kg, 37.8 moles, 1.11 equiv.) was then charged via an addition funnel over the course of 4 h 30 min. while maintaining the reaction temperature between 45 to 55° C. and a vigorous gas evolution was observed. A brown mixture was obtained after the addition. The brown mixture was held at 45 to 55° C. for 30 min. and then heated to 85 to 95° C. and stirred at 85 to 95° C. for 1 h. During heating, the brown mixture turned into a dark mixture. The dark mixture was slowly cooled to 20 to 25° C. over the course of 4 h and the reaction was monitored by quenching a portion of the reaction mixture into piperidine and monitoring the disappearance of the piperidine amide by HPLC until the area/area % of (1'): piperidine amide was <1.9. After the reaction was complete by HPLC the dark mixture was in-line filtered to 20 L rotavapor flask. Toluene (3.9 L) was used to rinse the reactor and in-line filtered to 20 L rotavapor flask. The filtered reaction mixture was concentrated under reduced pressure until most toluene has been distilled to furnish 4.4 kg acyl chloride as dark oil.

Separately, potassium carbonate (7.06 kg, 51.1 moles, 1.5 equiv.) and water (31 L) were stirred in a 100 L jacketed reactor. The reaction solution was cooled to -10 to 10° C. N,O-dimethylhydroxylamine hydrochloride (3.93 kg, 40.3 moles, 1.18 equiv.) was charged to the reactor followed by dichloromethane (39 L). The reaction mixture was cooled to -10 to 0° C. The above acyl chloride intermediate as dark oil (4.4 kg) was then charged slowly to 100 L jacketed reactor containing N,O-dimethylhydroxylamine in dichloromethane with vigorous stirring while maintaining the reaction temperature between -10 and 0° C. over a period of 30 min. The addition was a little exothermic and a brown mixture was obtained after the addition. The reaction mixture was stirred at -10 to 0° C. for 20 min. and then warmed to 15 to 25° C. and stirred for 10 min. The layers were separated and the bottom organic layer was collected and the top aqueous layer was extracted with dichloromethane (7.7 L). The aqueous layer was discarded and the combined organic layers were transferred to 100 L jacketed reactor and washed with 15 wt % sodium chloride solution (11.6 L). The layers were separated and the bottom organic layer was collected and the top aqueous layer was extracted with dichloromethane (3.9 L). The aqueous layer was discarded and the combined organic layers were concentrated under reduced pressure until most dichloromethane was removed. Tetrahydrofuran (7.7 L) was charged to this dark oil and concentrated under reduced pressure until most tetrahydrofuran was removed to furnish intermediate (2') as dark oil (4.6 kg, 86% yield, 0.01 wt % water content by KF, 98.9% pure by HPLC).

ii): Alkylation of Compound (2') and Ethyl Propiolate to Provide (E)-ethyl 4-(isoxazol-3-yl)-2-(methoxy(methyl)amino)-4-oxobut-2-enoate (3')

Intermediate (2') (2.99 kg, 19.15 moles, 1.0 equiv.), ethyl propiolate (2.08 kg, 21.2 moles, 1.1 equiv.) and anhydrous THF (15 L) were mixed in a 50 L round bottom flask equipped with a mechanical stirrer and a digital thermometer. The reaction solution was cooled to -70° C. to -60° C. Sodium bis(trimethylsilyl)amide in THF (40 wt %, 9.52 kg, 21 moles, 1.1 equiv.) was then charged slowly via an addition funnel while maintaining the reaction temperature at -65 to -50° C. over 1 h and 30 min. After the addition, the reaction mixture was stirred at below -55° C. for 10 min. Then 2 N HCl (10.7 L, 21.6 moles, 1.14 equiv.) was charged over 2 min. to quench the reaction while maintaining the reaction temperature below 20° C. (exotherms from -65° C. to 18° C.). Separately, ethyl acetate (39 L) was charged in advance to 100 L jacketed reaction vessel and the above reaction mixture from 50 L round bottom flask was quickly transferred to 100 L jacketed reaction vessel containing ethyl acetate. 20% citric acid (10.5 L, 10.93 moles, 0.57 equiv.) was charged to adjust the batch pH ~4-5 and stirred for 5 min. The bottom aqueous layer was discarded and the top ethyl acetate layer was collected and washed twice with 15 wt % sodium chloride solution (9.0 L per wash). The organic layer was in-line filtered and concentrated under reduced pressure to a volume of 9.0 L. Ethanol (9.0 L) was charged and concentrated to remove water azeotropically under reduced pressure to a volume of 9.0 L to furnish 8.1 kg of the crude product (3') in ethanol as dark brown oil. (3.59 kg by $^1$H-NMR assay, 74% yield).

iii): Cyclization of Compound (3') and 2-fluorobenzylhydrazine to Provide ethyl 1-(2-fluorobenzyl)-5-(isoxazol-3-yl)-1H-pyrazole-3-carboxylate (4')

2-Fluorobenzylhydrazine (3.234 kg, 18.3 moles, 1.3 equiv.), water (0.9 L) and absolute ethanol (7.2 L) were mixed in 100 L jacketed reaction vessel. The reaction solution was cooled to 10-25° C. Separately, potassium carbonate (1.27 kg, 9.19 moles, 0.65 equiv.) was charged to a suitable reaction vessel and dissolved in water (1.8 L). The potassium carbonate solution was then charged to the 100 L jacketed reaction vessel containing 2-Fluorobenzylhydrazine solution between 15-25° C. followed by absolute ethanol (25.2 L). The reaction solution was cooled to 10 to 20° C. and intermediate (3') (3.59 kg, 14.12 moles, 1.0 equiv.) in anhydrous ethanol was charged via an addition funnel over the course of 5 min. while maintaining the temperature below 30° C. This addition was slightly exothermic. After stirring for a minimum of 12 h at 15 to 25° C., the reaction was completed by HPLC (area/area % (3') (4')=0.7). Conc. HCl (1.53 L, 37 wt %, 18.4 moles, 1.3 equiv.) was charged to the reaction mixture over 1 min. and the batch temperature exothermed from 20° C. to 38° C. The mixture was cooled to 0 to 5° C. over 2 h and stirred at 0 to 5° C. for 1 h. The resulting slurry was filtered, and the filter cake was washed with a mixture of ethanol (11.5 L) and water (2.9 L) followed by water (28.7 L). The filter cake was dried under high vacuum at 40° C. over 16 h to furnish intermediate (4') as an off-white solid (2.538 kg, 57% yield, 98.8% pure by HPLC).

iv): Amination of Compound (4') to Provide 1-(2-fluorobenzyl)-5-(isoxazol-3-yl)-1H-pyrazole-3-carboximidamide hydrochloride (5'B)

Anhydrous ammonium chloride (1.39 kg, 26.0 moles, 3.8 equiv) and toluene (34.1 L) were mixed in a 100 L jacketed reaction vessel. Trimethylaluminum in toluene (2 M, 12 L, 24 moles, 3.5 equiv.) was charged over 2 h via an addition funnel, while maintaining the reaction temperature at 20 to 40° C. (Note: Methane gas evolution was observed during addition). The reaction mixture was stirred for minimum of 30 min at 20 to 40° C. Intermediate 1-4 (2.16 kg, 6.85 moles, 1.0 equiv.) in toluene (6.5 L) as a slurry was charged to reaction mixture in one portion at 20 to 40° C. The reaction mixture was heated to 70 to 80° C. and held for 30 min. The mixture was then heated to 100 to 110° C. over 30 min and held for 3 h at 100 to 110° C. The reaction was completed by HPLC (1-4: ND vs 1-5). The reaction mixture was cooled to 20 to 40° C. and methanol (2.94 L, 72.6 moles, 10.6 equiv) was charged over 1 h via an addition funnel, while maintaining the reaction temperature at 20 to 40° C. (Note: very exothermic quench and a lot of gas evolution were observed). A thick slurry was obtained. 3N HCl (26.3 L, 78.9 moles, 11.5 equiv) was charged via an addition funnel, while maintaining the reaction temperature at 20 to 45° C. The mixture was heated to 82 to 85° C. and stirred for 10 min to obtain a clear biphasic mixture. The mixture was cooled to 20 to 25° C. over 2 h and stirred for 30 min. The resulting slurry was filtered, and the filter cake was washed with water (10.8 L). The filter cake was dried under vacuum at 60° C. over 16 h until constant weight to furnish intermediate (5'B) as an off-white solid (2.015 kg, 91% yield, 96% pure by HPLC). $^1$H-NMR (500 MHz, DMSO-d$_6$) δ ppm 9.52 (s, 2H); 9.33 (s, 2H); 9.18 (d, J=1.53 Hz, 1H); 7.88 (s, 1H); 7.29-7.38 (m, 1H); 7.19-7.25 (m, 1H); 7.10-7.16 (m, 1H); 7.03 (d, J=1.53 Hz, 1H); 6.92-6.98 (m, 1H); 5.91 (s, 2H). M.P. 180-185° C.

v): Cyclization of Compound (5') and Diethyl Fluoromalonate to Provide 5-fluoro-2-(1-(2-fluorobenzyl)-5-(isoxazol-3-yl)-1H-pyrazol-3-yl)pyrimidine-4,6-diol (6')

Intermediate (5') (3.34 kg, 10.38 moles, 1.0 equiv.), methanol (33.4 L) and diethyl fluoromalonate (2.95 L, 3.33 kg, 18.69 moles, 1.8 equiv.) were mixed in 100 L jacketed reaction vessel. Sodium methoxide in methanol solution (5.4 M solution, 8.75 L, 47.2 moles, 4.5 equiv.) was charged over the course of 1 h 30 min. via an addition funnel while maintaining the reaction temperature at 20 to 30° C. The reaction mixture was stirred at 20-30° C. over 30 min. and a light suspension was obtained. The reaction was completed by HPLC (1-5: ND vs 1-6). 1.5 N HCl (34 L, 51 moles, 4.9 equiv.) was charged via an addition funnel over 1 h 20 min. while maintaining the reaction temperature at 20 to 30° C. A white suspension was obtained. The pH of the reaction mixture was to be ~1 by pH paper. The slurry was stirred at 20 to 30° C. over 30 min. The resulting slurry was filtered, and the filter cake was washed with a pre-mixed solution of methanol and water (8.35 L/8.35 L), and water (16.7 L) followed by acetonitrile (10 L). The filter cake was dried under vacuum at 60° C. over 16 h to furnish intermediate (6') as an off-white solid (3.76 kg, 98% yield, >99% pure by HPLC).

vi): Chlorination of Compound (6') to Produce 3-(3-(4,6-dichloro-5-fluoropyrimidin-2-yl)-1-(2-fluorobenzyl)-1H-pyrazol-5-yl)isoxazole (7')

Intermediate (6') (3.6 kg, 9.695 moles, 1.00 equiv.), acetonitrile (50.4 L) and N,N-dimethylaniline (1.98 L, 15.6 moles, 1.6 equiv.) were mixed in a 100 L jacketed reaction vessel equipped with a nitrogen inlet-outlet, thermocouple, condenser, an addition funnel and overhead stirrer. The mixture was then heated to 70 to 80° C. Phosphoryl chloride (5.44 L, 8.95 kg, 58.37 moles, 6.0 equiv.) was charged via an addition funnel over 1 h 40 min. while maintaining the reaction temperature at 70 to 80° C. The reaction mixture was stirred at 75 to 80° C. over 21 h and a brown solution was obtained. The reaction was completed by HPLC (area/area % (6): (7')=0.4). The reaction mixture was cooled to 0 to 5° C. over 40 min. while vigorously stirring and solids precipitated out at 28 to 30° C. Water (39.6 L) was charged slowly via an addition funnel over 2 h 20 min. while maintaining the reaction temperature between 0 and 10° C. The slurry was stirred at 0 to 5° C. over 30 min. The resulting slurry was filtered onto 18 inch Buchner funnel. A solution of acetonitrile (9 L) and water (9 L) was mixed in the reactor to cool to 10 to 15° C. and transferred to the filter to wash the cake. Water (18 L) was cooled in the reactor to 16° C. and transferred to the filter to wash the cake. The wet cake was dried on the filter for 21 h and then the wet cake was dried under vacuum at 50° C. over 50 h until constant weight to furnish intermediate (7') as an off-white solid (3.755 kg, 95% yield, 99% pure by HPLC)

vii): Substitution of Compound (7') with Methoxide to Provide 3-(3-(4-chloro-5-fluoro-6-methoxypyrimidin-2-yl)-1-(2-fluorobenzyl)-1H-pyrazol-5-yl)isoxazole (8')

Methanol (45 L) and sodium methoxide in methanol (2.02 L, 5.4 M, 10.91 moles, 1.19 equiv.) were mixed in a 100 L jacketed reaction vessel with a nitrogen inlet, thermocouple, condenser, and overhead stirrer. The reaction mixture was heated to 23 to 27° C. Intermediate (7') (3.755 kg, 9.2 moles, 1.0 equiv.) was charged to the reaction mixture in small portions (40 to 60 g each portion) over 1 h 30 min. while maintaining the reaction temperature at 23 to 27° C. The slurry was stirred at 15 to 27° C. over 1 h. The reaction was completed by HPLC (area/area % (7'): (8')=1.8). The slurry was filtered through an 18 inch Buchner funnel. Methanol (7.5 L) was charged to the reactor and then transferred to the filter to wash the cake. The filter cake was washed with water (11.3 L) and then methanol (7.5 L). The wet cake was dried on the filter for 1 h and then dried under vacuum at 40° C. over 18 h until constant weight to furnish intermediate (8') as an off-white solid (3.59 kg, 97% yield, 96.4% pure by HPLC).

viii): Hydrogenation of Compound (8') to Provide 3-(3-(5-fluoro-4-methoxypyrimidin-2-yl)-1-(2-fluorobenzyl)-1H-pyrazol-5-yl)isoxazole (9')

Intermediate (8') (1.87 kg, 4.63 moles, 1.0 equiv.), palladium (10% on activated carbon, nominally 50% water wet, 0.188 kg, 87 mmoles, 0.02 equiv), tetrahydrofuran (26.2 L) and triethylamine (1.03 L, 7.39 moles, 1.6 equiv.) were mixed in a 30 L jacketed reaction vessel with a nitrogen inlet, thermocouple, condenser, and overhead stirrer. Nitrogen was bubbled into the reaction mixture via teflon tubing over 24 min. at 15 to 30° C. Then the mixture was heated to 40 to 50° C. and hydrogen gas was bubbled into the reaction mixture via teflon tubing over 3 h while maintaining the reaction temperature at 40 to 50° C. The reaction was completed by HPLC (area/area % (8'): (9')=1.7). Nitrogen was then bubbled into the reaction mixture via teflon tubing over 25 min. at 40 to 50° C. and the mixture was heated to 45 to 50° C. prior to filtering. The reaction mixture was hot filtered through Hyflo Supercel. Tetrahydrofuran (11.2 L) was charged to the reactor, heated to 45° C. and transferred to the filter to wash the cake. The filtrate was concentrated under reduced pressure to a volume of 9.4 L to give a slurry and tetrahydrofuran was then solvent exchanged to methanol under reduced pressure via continuously feeding methanol (22.5 L). The final volume after solvent exchange was 11.2 L and the tetrahydrofuran content was confirmed to be <1 wt % by $^1$H-NMR. The resulting slurry was filtered onto 18 inch Buchner funnel and the filter cake was washed with methanol (3.7 L). The wet cake was dried on the filter for 25 min. and then dried under vacuum at 40° C. over 4 h until constant weight to furnish intermediate (9') as a white solid (1.54 kg, 90% yield, 98.4% pure by HPLC).

ix): Demethylation of Compound (9') to Provide 5-fluoro-2-(1-(2-fluorobenzyl)-5-(isoxazol-3-yl)-1H-pyrazol-3-yl)pyrimidin-4-ol (10')

Intermediate (9') (4.44 kg, 12.0 moles, 1.0 equiv.), methanol (64.4 L) and concentrated hydrochloric acid (4.88 L, 37 wt. %, 59.4 moles, 4.95 equiv.) were charged a 75 L jacketed reaction vessel equipped with a nitrogen inlet-outlet, thermocouple, condenser, and overhead stirrer. The mixture was heated to 62 to 65° C. and became a solution at 63° C. The reaction mixture was then stirred at 62 to 65° C. over 20 h and a slurry was obtained. The reaction was completed by HPLC (area/area % (9'): (10')=0.4). The slurry was cooled to 20 to 25° C. over 50 min. and held for 45 min. The resulting slurry was filtered through an 18 inch Buchner funnel. Methanol (13.3 L) was charged to the reactor and then transferred to the filter to wash the cake. The wet cake was dried on the filter for 1 h 30 min. and then the solid was dried under vacuum at 40° C. over 8 h until constant weight to furnish intermediate (10') as a white solid (4.11 kg, 96% yield, 99.7% pure by HPLC).

x): Chlorination of Compound (10') to Provide 3-(3-(4-chloro-5-fluoropyrimidin-2-yl)-1-(2-fluorobenzyl)-1H-pyrazol-5-yl)isoxazole (Formula IV)

Intermediate (10') (2.66 kg, 7.48 moles, 1.0 equiv.), acetonitrile (37.2 L) and N,N-dimethylaniline (1.41 L, 1.348 kg, 11.12 moles, 1.49 equiv.) were mixed in a 100 L jacketed reaction vessel with a nitrogen inlet, thermocouple, addition funnel, condenser, and overhead stirrer. The slurry was heated to 70 to 80° C. Phosphorous oxychloride (2.1 L, 3.46 kg, 22.5 moles, 3.0 equiv.) was charged via an addition funnel over 1 h 20 min. while maintaining the reaction temperature between 70 and 80° C. The mixture was stirred at 75 to 80° C. over 2 h and a green solution was obtained. The reaction was complete by HPLC (area/area % (10'): Formula IV=0.2). Then the mixture was cooled to −5 to 5° C. over 1 h. Water (18.6 L) was charged slowly over 40 min. via an addition funnel while maintaining the reaction temperature at −5 to 5° C. The slurry was stirred at 0 to 5° C. over 30 min., then was filtered onto 18 inch Buchner funnel. Acetonitrile (6.6 L) and water (6.6 L) were charged to the reactor and stirred for 3 min. then transferred to the filter to wash the cake. Water (6.6 L) was cooled in the reactor to 13° C. and transferred to the filter to wash the cake. The wet cake was dried on the filter for 2 h and then dried under vacuum at 40° C. over 16 h to furnish the intermediate Formula IV as an off-white to pink solid (2.67 kg, 96% yield, 99.3% pure by HPLC).

a): Cyanation of Intermediate (15) to Provide 2-(bromomethyl)-3,3,3-trifluoro-2-((trimethylsilyl)oxy)propanenitrile (16)

Trimethylsilanecarbonitrile (2.52 kg, 25.4 mmoles, 0.97 equiv) and triethylamine (0.073 L, 0.053 kg, 0.52 moles, 0.02 equiv) were mixed in a 12 L round bottom flask equipped with a mechanical stirrer, an addition funnel and a digital thermometer. The mixture was cooled to 10-15° C. 3-Bromo-1,1,1-trifluoropropan-2-one ((15), 5.0 kg, 26.2 moles, 1.0 equiv) was charged via an addition funnel over 40 min, while maintaining the reaction temperature between 0 and 15° C. The reaction mixture was then stirred at 20 to 25° C. over 1 h. $^1$H-NMR of a reaction sample indicated the reaction was completed (area: area % (15):(16)<1%)) and furnished intermediate (16) as a dense oil. This intermediate (16) was used directly in the next step without further purification. $^1$H-NMR (500 MHz, CDCl$_3$) δ ppm 3.68 (d, J=11.14 Hz, 1H); 3.57 (d, J=11.14 Hz, 1H), 0.34-0.37 (m, 9H).

b): Conversion of Nitrile Intermediate (16) to 2-(bromomethyl)-3,3,3-trifluoro-2-hydroxypropanamide (17)

Concentrated sulfuric acid (7.5 L, 136 moles, 5.2 equiv) was stirred in a 75 L jacketed reactor. The sulfuric acid was heated at 40 to 45° C., then intermediate (16) obtained above was added via an addition funnel over 1 h while keeping the temperature below 75° C. The reaction mixture was stirred at 65 to 75° C. for 2 h and then allowed to cool to 20 to 25° C. and held at this temperature for 17 h. The reaction mixture was cooled to −15 to −5° C. and diluted with ethyl acetate (35 L) via an addition funnel over 2 h (very exothermic) while keeping the temperature between −15 to −5° C. Water (25 L) was added via an addition funnel for 1 h 30 min (very exothermic) while keeping the temperature between −15 to −5° C. The reaction mixture was warmed to and held at 0 to 5° C. The layers were separated and 15% aqueous sodium chloride (13.5 L) was added to the organic layer, followed by 20% aqueous sodium bicarbonate (13 L), over 5 min, while maintaining the temperature between 5 to 20° C. The mixture was stirred for 10 min. and the layers were separated. The organic layer was washed with 15% aqueous sodium chloride (13.5 L). The organic layer was transferred via an in-line filter via gas dispersion tube (coarse frit) to a 20 L rotavapor and concentrated under reduced pressure until no more distillate was observed, furnishing 8.38 kg of crude intermediate (17) as light yellow oil, which contained 72 wt % of intermediate (17) based on $^1$H-NMR assay. This oil was dissolved in methanol (10 L) and concentrated again to furnish 8.47 kg of crude intermediate (17). (6.04 kg adjusted weight, 98% yield). $^1$H-NMR (500 MHz, CDCl$_3$) δ 6.61-6.94 (m, 1H); 5.92-6.26 (m, 1H); 3.93-4.00 (m, 1H); 3.68 (d, J=11.14 Hz, 1H).

c): N-Alkylation of Compound (17) to Provide of 2-(Aminomethyl)-3,3,3-trifluoro-2-hydroxypropanamide (14)

7 N ammonia in methanol (41.5 L, 291 moles, 11.4 equiv) was stirred in a 75 L reactor. The solution was cooled to −10 to 10° C. Then the above crude intermediate (17) (6.04 kg, 25.6 moles, 1.0 equiv) was added via an addition funnel over 3 min. The reaction mixture was warmed to 20 to 30° C. over 1 h and held at this temperature for 16 h. The reaction mixture was cooled to 0 to 10° C. and sodium methoxide (4.53 L, 5.4 M, 24.5 moles, 0.96 equiv) was added over 2 min. The reaction mixture was then split into 4 equal portions and processed. Each portion was concentrated under reduced pressure to a volume of 6.0 L and ethyl acetate (15.1 L) was continuously charged while distilling to azeotropic removal of methanol to a volume of 6.0 L as a slurry. This process was repeated for the rest of the three portions. All the ethyl acetate slurries from 4 portions were transferred to a 75 L jacketed reactor and more ethyl acetate was added to make up the volume to 65 L. Water (6.0 L) was added and the reaction mixture was stirred vigorously for 20 to 30 min and then allowed to separate for a minimum of 12 h.

The ethyl acetate layer was then split into 4 equal portions and processed. Each portion was concentrated under reduced pressure to a volume of 6.0 L. This process was repeated for the rest of the three portions. All 4 portions were transferred to the 75 L jacketed reactor and ethyl acetate was added to make up the volume to 36.2 L. The reaction mixture was heated to 55 to 60° C. and heptane (36.2 L) was added over 30 min, while maintaining the temperature above 50° C. The resulting slurry was cooled to 20 to 25° C. over 30 min, held at 20 to 25° C. for 1 h, and filtered through an 18 inch Buchner funnel. Ethyl acetate (6.0 L) and heptane (12.1 L) were charged to the reactor, the mixture stirred for 2 min, and transferred to the filter to wash the cake. The wet cake was dried on the filter for 2 h and then dried under vacuum at 25 to 30° C. over 36 h until constant weight furnishing amine (14) as an off-white solid (2.52 kg, 57% yield). $^1$H-NMR (500 MHz, MeOH-d$_4$) δ ppm 2.94 (d, J=13.73 Hz, 1H); 3.24 (d, J=13.58 Hz, 1H).

d): Chiral Resolution of Amine (14) as a 1:1 (R)-2,2-dimethyl-5-(trifluoromethyl)oxazolidine-5-carboxamide (18A):(D)-malic acid salt Amine (14) (2.0 kg, 11.6 moles, 1.0 equiv) and acetone (10.0 L) were mixed in a 22 L round bottom flask equipped with a mechanical stirrer, an addition funnel and a digital thermometer. The reaction mixture was stirred at low speed at 20 to 25° C. to obtain a solution.

Separately, D-(+)-Malic acid (1.56 kg, 11.6 moles, 1.0 equiv) and acetone (30 L) were stirred in a 100 L jacketed reactor. The reaction solution was heated to 33 to 38° C. Then 20% of above amine (14) in acetone was charged to a 100 L jacketed reactor in one portion followed by addition of a slurry of the 1:1 salt of intermediate (18A) and (D)-malic acid (0.52 g) in acetone (20 mL) as seeds. The remaining 80% of amine (14) in acetone was then charged to 100 L jacketed reactor over a minimum of 1 h, while maintaining the reaction temperature between 33 to 38° C. The reaction mixture was cooled to 28 to 32° C. evenly over a minimum of 2 h and stirred at 28 to 32° C. over a minimum of 12 h. The resulting slurry was filtered at 28 to 32° C., and the filter cake was washed with acetone (16.0 L) (Note: Care was taken to ensure that the filter cake did not dry at the beginning of filtration). The filter cake was then dried under vacuum at 30° C. over 8 h until constant weight to furnish the 1:1 salt of intermediate (18A) and (D)-malic acid as an off-white solid (1.53 kg, 38% yield, RR:SR=97:3 by chiral GC). $^1$H-NMR (500 MHz, D$_2$O) δ ppm 4.33 (br, s, 1H); 3.61 (br, d, J=13.58 Hz, 1H); 3.40-3.47 (m, 1H); 2.76 (br, d, J=15.87 Hz, 1H); 2.53-2.63 (m, 1H); 2.16 (br, s, 4H).

e): Coupling of Formula IV and the 1:1 Salt of Intermediate (18A) and (D)-malic Acid to Provide (R)-3,3,3-trifluoro-2-(((5-fluoro-2-(1-(2-fluorobenzyl)-5-(isoxazol-3-yl)-1H-pyrazol-3-yl)pyrimidin-4-yl)amino)methyl)-2-hydroxypropanamide (Compound IA)

The 1:1 salt of intermediate (18A) and (D)-malic acid (0.81 kg, 2.34 moles, 1.25 equiv) and water (0.98 L) were charged to a 30 L jacketed reaction vessel. The reaction mixture was stirred at low speed and the jacket was heated to 65 to 70° C. and held at this temperature for 30 min. Acetone generated during the reaction was removed by applying a gentle vacuum. Reaction mixture was cooled to 20 to 40° C. and Formula IV (0.70 kg, 1.87 moles, 1.0 equiv), DMSO (9.8 L) and Hunig's base (0.82 L, 4.71 moles, 2.5 equiv) were charged. The reaction mixture was heated to 88 to 93° C. over 2 h and held at 88 to 93° C. for 20 h. The reaction was completed by HPLC (area/area % Formula IV: Compound IA=0.5). Then the mixture was cooled to 50 to 60° C. Another portion of Hunig's base (1.96 L, 11.3 moles, 6.0 equiv) was charged followed by water (4.9 L) over 15 min at 50 to 60° C. The reaction mixture was stirred for 15 min at 50 to 60° C. to form the seed bed. Water (7.0 L) was added via addition funnel at 50 to 60° C. over 30 min, and the mixture was held at 50 to 60° C. for 30 min. The resulting slurry was filtered at 50 to 60° C., and the filter cake was washed with a pre-mixed solution of methanol and water (3.5 L/3.5 L). The filter cake was then dried under vacuum at 50° C. over 16 h until constant weight to furnish crude Compound IA as an off-white solid (0.83 kg, 87% yield). $^1$H-NMR (500 MHz, DMSO-d$_6$) δ ppm 9.10 (s, 1H); 8.33 (d, J=2.90 Hz, 1H); 7.93 (s, br, 1H); 7.90 (s, 1H); 7.78 (s, br, 1H); 7.69 (s, br, 1H); 7.52 (s, 1H); 7.33 (q, J=7.02 Hz, 1H); 7.17-7.25 (m, 1H); 7.17-7.25 (m, 1H); 7.10 (t, J=7.48 Hz, 1H); 6.98 (t, J=7.55 Hz, 1H); 5.90 (s, 2H); 3.92-4.05 (m, 2H).

The invention claimed is:

1. A process for preparing a compound of Formula III:

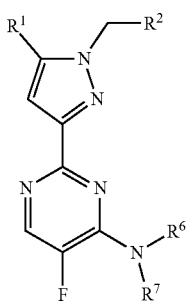

Formula III wherein:
  $R^1$ is unsubstituted phenyl or 5 to 6-membered heteroaryl ring containing up to three ring heteroatoms independently selected from N, O or S;
  $R^2$ is phenyl or a 6-membered heteroaryl, both optionally substituted with up to three instances of $R^5$;
  wherein said 6-membered heteroaryl ring contains up to 2 nitrogen ring atoms;
    each $R^5$ is independently selected from $C_{1-6}$ alkyl, $C_{1-6}$ alkoxy or halogen;
  $R^6$ is hydrogen;
  $R^7$ is $C_{1-6}$ alkyl substituted with 3 instances of $R^8$; and the three instances of $R^8$ are —OH, $C_{1-3}$ haloalkyl, and —C(O)NH$_2$;
said process comprising the steps of:
  A) coupling an appropriate amount of an amine (13):

(13)

with a dichloropyrimidine (7):

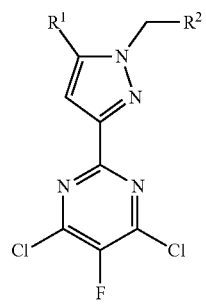

(7)

in a suitable aprotic organic solvent, optionally in the presence of an appropriate amount of a suitable base, at a suitable temperature, to yield an intermediate of Formula VII:

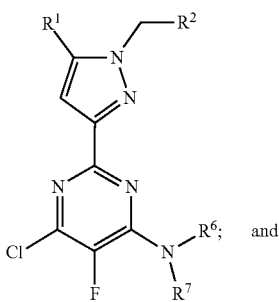

Formula VII and

B) de-chlorinating the intermediate of Formula VII with hydrogen gas or a transfer hydrogenation reagent and, optionally, an appropriate amount of a suitable metal catalyst, in the presence of an appropriate amount of a suitable base, at a suitable temperature, in a suitable organic solvent.

2. The process according to claim 1, wherein the compound of Formula III is a compound of Formula V:

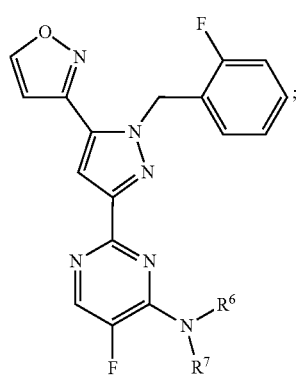

Formula V said process comprising
  A) coupling an appropriate amount of an amine (13)

(13)

with a dichloropyrimidine (7')

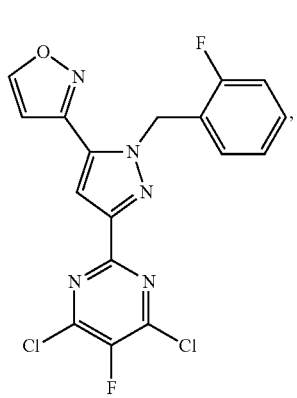

(7')

in a suitable aprotic organic solvent, optionally in the presence of an appropriate amount of a suitable base, at a suitable temperature, to yield an intermediate of Formula VIII:

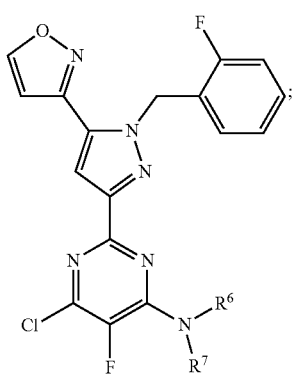

Formula VIII and

B) de-chlorinating the intermediate of Formula VIII with hydrogen gas or a transfer hydrogenation reagent and, optionally, an appropriate amount of a suitable metal catalyst, in the presence of an appropriate amount of a suitable base, at a suitable temperature, in a suitable organic solvent.

3. The process according to claim 1, wherein the compound of Formula III is a compound of Formula VI:

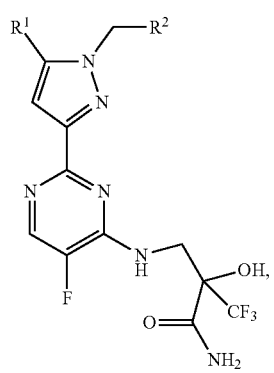

Formula VI wherein:

$R^1$ is unsubstituted phenyl, or 5 to 6-membered heteroaryl ring containing up to three ring heteroatoms independently selected from N, O or S;

$R^2$ is phenyl or a 6-membered heteroaryl, both optionally substituted with up to three instances of $R^5$;

wherein said 6-membered heteroaryl ring contains up to 2 nitrogen ring atoms;

each $R^5$ is independently selected from $C_{1-6}$ alkyl, $C_{1-6}$ alkoxy or halogen;

said process comprising:

A) coupling an appropriate amount of an amine (14):

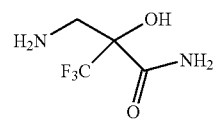

(14)

with a dichloropyrimidine (7)

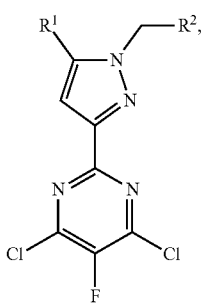

(7)

in a suitable aprotic organic solvent, optionally in the presence of an appropriate amount of a suitable base, at a suitable temperature, to yield an intermediate of Formula IX:

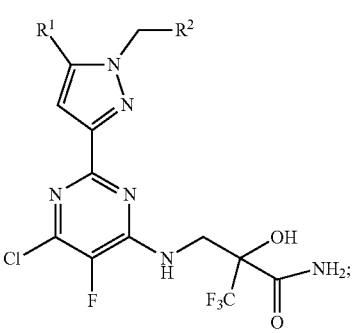

Formula IX and

B) de-chlorinating the intermediate of Formula IX with hydrogen gas or a transfer hydrogenation reagent and, optionally, an appropriate amount of a suitable metal catalyst, in the presence of an appropriate amount of a suitable base, at a suitable temperature, in a suitable organic solvent.

4. The process according to claim 3, said process further comprising:

a) treating bromo intermediate 15:

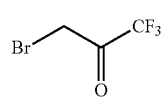

(15)

with an appropriate amount of trimethylsilanecarbonitrile, KCN or NaCN in the presence of an appropriate amount of a suitable organic amine, optionally in the presence of water as the solvent, at a suitable temperature to provide intermediate 16:

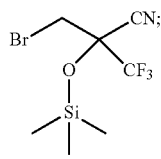

(16)

b) treating intermediate 16 with an appropriate amount of a strong aqueous mineral acid, at a suitable temperature, to provide intermediate 17

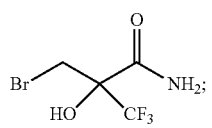

(17)

and c) treating intermediate 17 with an appropriate amount of ammonia, in a suitable protic solvent, at a suitable temperature to provide amine 14.

5. The process according to claim 1, wherein the compound of Formula III is Compound I:

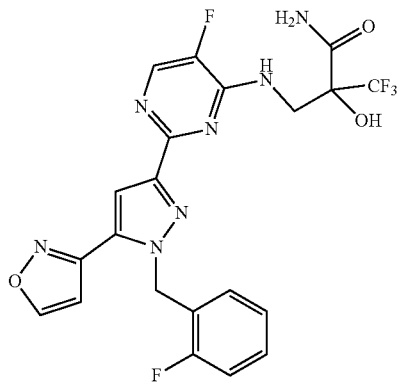

Compound I said process comprising:

A) coupling an appropriate amount of an amine (14):

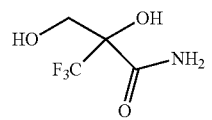

(14)

with a dichloropyrimidine (7'):

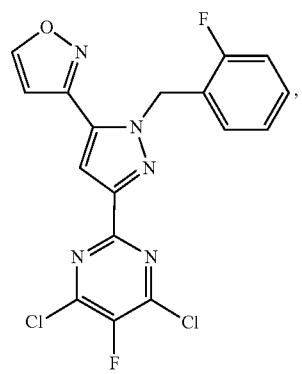

(7')

in a suitable aprotic organic solvent, optionally in the presence of an appropriate amount of a suitable base, at a suitable temperature, to yield an intermediate of Formula X:

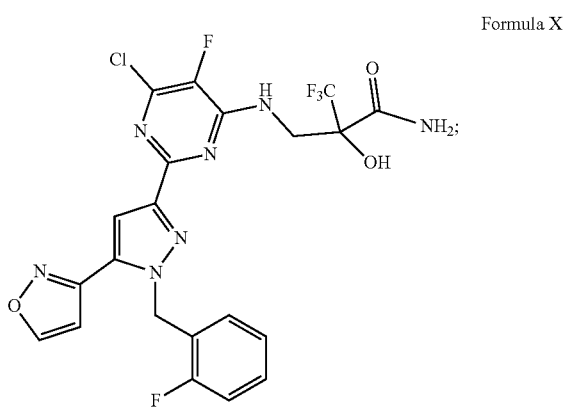 [SMILES: NC(=O)C(O)(CNc1nc(-c2cc(-c3ccon3)n(Cc3ccccc3F)n2)nc(Cl)c1F)C(F)(F)F]

Formula X and

B) de-chlorinating the intermediate of Formula X with hydrogen gas or a transfer hydrogenation reagent and, optionally, an appropriate amount of a suitable metal catalyst, in the presence of an appropriate amount of a suitable base, at a suitable temperature, in a suitable organic solvent.

6. The process according to claim 5, said process further comprising:

a) treating bromo intermediate (15):

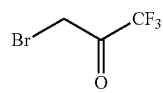

(15)

with an appropriate amount of trimethylsilanecarbonitrile, KCN or NaCN in the presence of an appropriate amount of a suitable organic amine, optionally in the presence of water as the solvent, at a suitable temperature to provide intermediate (16);

b) treating intermediate (16):

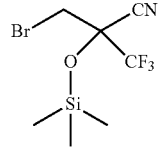
(16)

with an appropriate amount of a suitable strong aqueous mineral acid, at a suitable temperature, to provide intermediate (17):

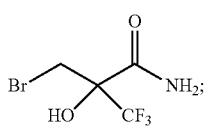
(17)

and c) treating intermediate (17) with an appropriate amount of ammonia, in a suitable protic solvent, at a suitable temperature to provide amine (14).

7. A process for preparing Compound IA:

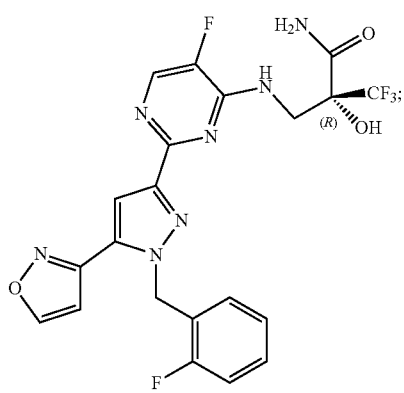
Compound IA said process comprising coupling an appropriate amount of amine (14A):

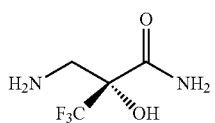
(14A)

with a chloropyrimidine of Formula IV:

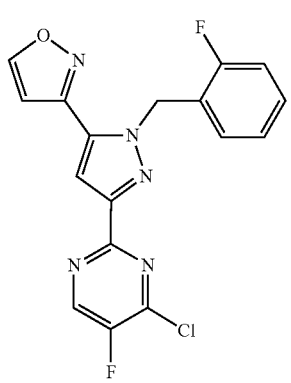
Formula IV in a suitable aprotic organic solvent, optionally in the presence of an appropriate amount of a suitable base, at a suitable temperature, wherein amine (14A) is prepared by:

i) reacting intermediate amine (14) with an appropriate amount of (D)-malic acid in a suitable aprotic organic solvent, at a suitable temperature, to provide a 1 to 1 salt of chiral intermediate (18A) and (D)-malic acid:

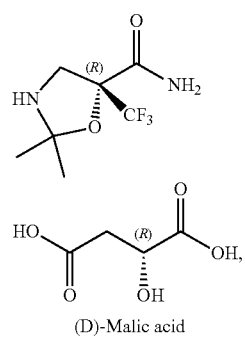
(18A)

(D)-Malic acid followed by crystallization to separate said salt from the unreacted enantiomeric amine (14B):

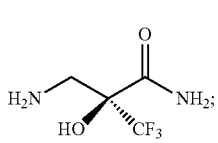
(14B)

and ii) heating the (D) malic acid salt obtained in step i), at a suitable temperature, in a suitable solvent, in order to liberate intermediate (14A):

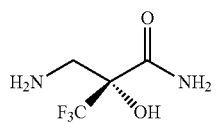
(14A)

into solution, with loss of acetone.

8. The process according to claim 1, wherein the compound of Formula III is Compound IA:

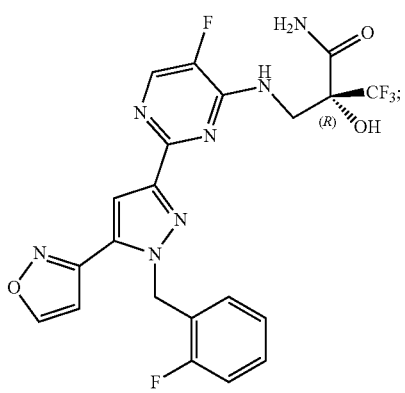

Compound IA said process comprising:
A) coupling an appropriate amount of an amine (14A):

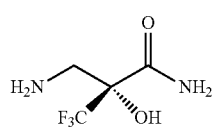

(14A)

with a dichloropyrimidine (7'):

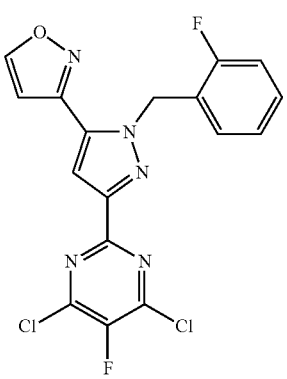

(7')

in a suitable aprotic organic solvent, optionally in the presence of an appropriate amount of a suitable base, at a suitable temperature, to yield an intermediate of Formula XA:

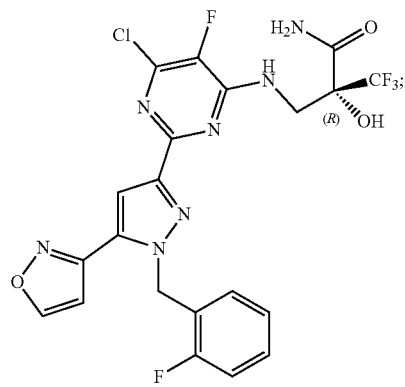

Formula XA and

B) de-chlorinating the intermediate of Formula XA with hydrogen gas or a transfer hydrogenation reagent and, optionally, an appropriate amount of a suitable metal catalyst, in the presence of an appropriate amount of a suitable base, at a suitable temperature, in a suitable organic solvent.

9. The process according to claim 7 for preparing Compound IA:

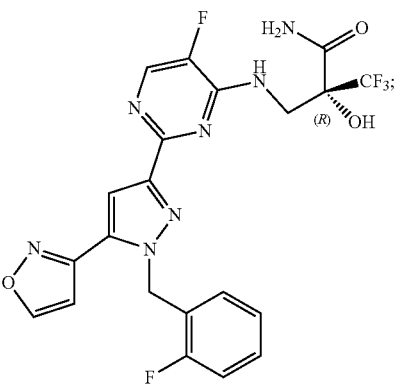

Compound IA said process comprising:
a) treating bromo intermediate (15):

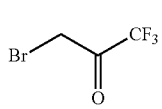

(15)

with an appropriate amount of trimethylsilanecarbonitrile, KCN or NaCN in the presence of an appropriate amount of a suitable organic amine, optionally in the presence of water as the solvent, at a suitable temperature to provide intermediate (16):

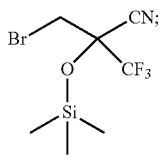

(16)

b) treating intermediate (16) with an appropriate amount of a suitable strong aqueous mineral acid, at a suitable temperature, to provide intermediate (17):

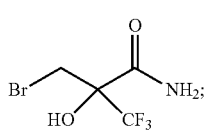

(17)

and c) treating intermediate (17) with an appropriate amount of ammonia, in a suitable protic solvent, at a suitable temperature, to provide amine (14):

(14)

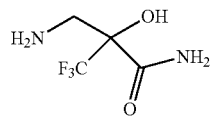

d) reacting intermediate amine (14) with an appropriate amount of (D)-malic acid in a suitable aprotic organic solvent, at a suitable temperature, to provide a 1 to 1 salt of chiral intermediate (18A) and (D)-malic acid:

(18A)

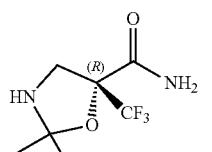

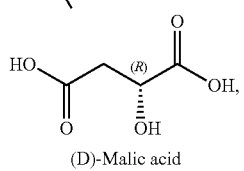

(D)-Malic acid followed by crystallization to separate said salt from the unreacted enantiomeric amine (14B); and e) heating the (D) malic acid salt obtained in step d), at a suitable temperature, in a suitable solvent, in order to liberate intermediate (14A):

(14A)

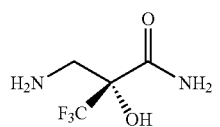

into solution, with loss of acetone, and reacting the resulting solution with an intermediate fluorochloro pyrimidine of Formula IV:

Formula IV

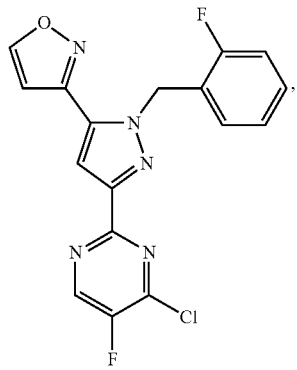

in a suitable solvent, at a suitable temperature, optionally in the presence of an appropriate amount of a suitable amine.

10. A process for preparing Compound IB:

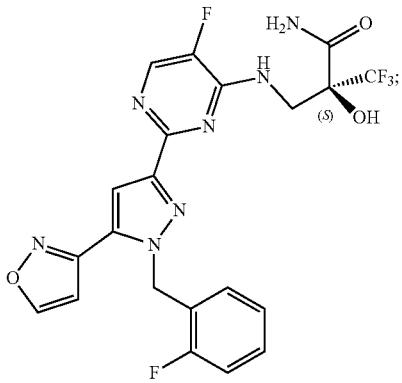

said process comprising coupling an appropriate amount of amine (14B):

(14B)

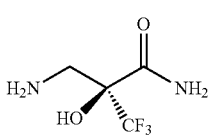

with a chloropyrimidine of Formula IV:

Formula IV

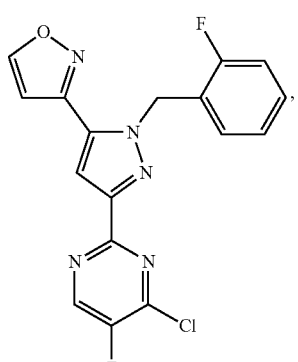

in a suitable polar aprotic solvent, optionally in the presence of an appropriate amount of a suitable base, at a suitable temperature, wherein amine (14B) is prepared by:

i) reacting an intermediate amine (14):

(14)

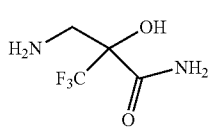

with (L)-malic acid, in an aprotic organic solvent, to provide a 1 to 1 salt of chiral intermediate (18B) and (L)-malic acid:

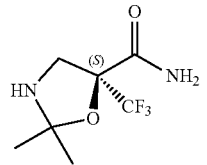
(18B)

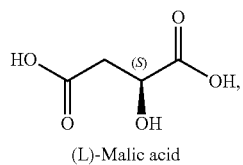
(L)-Malic acid followed by crystallization to separate said salt from the unreacted enantiomeric amine (14A):

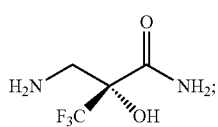
(14A)

and ii) heating the (L) malic acid salt obtained in step i), in a solvent, in order to liberate intermediate (14B):

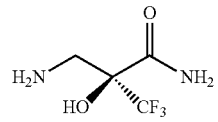
(14B)

into solution, with loss of acetone.

11. The process according to claim 1, wherein the compound is Compound IB:

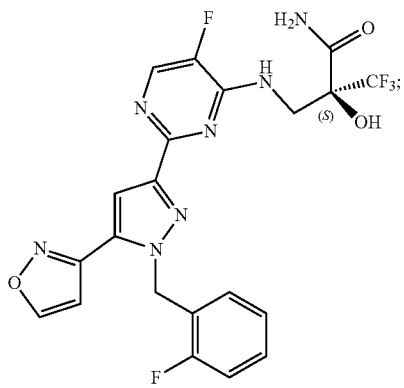

said process comprising:

A) coupling an appropriate amount of an amine (14B):

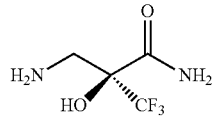
(14B)

with a dichloropyrimidine (7'):

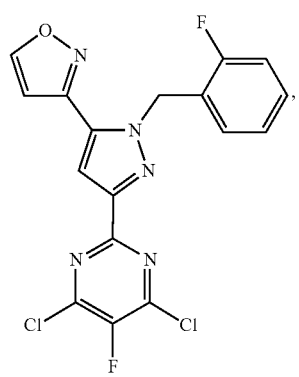
(7')

in a suitable aprotic organic solvent, optionally in the presence of an appropriate amount of a suitable base, at a suitable temperature, to yield an intermediate of Formula XB:

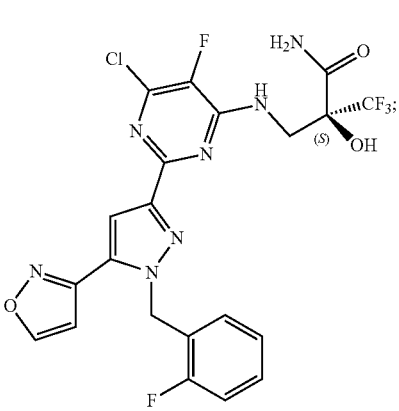
Formula XB and

B) de-chlorinating the intermediate of Formula XB with hydrogen gas or a transfer hydrogenation reagent and, optionally, an appropriate amount of a suitable metal catalyst, in the presence of an appropriate amount of a suitable base, at a suitable temperature, in a suitable organic solvent.

12. The process according to claim 10 for preparing Compound IB:

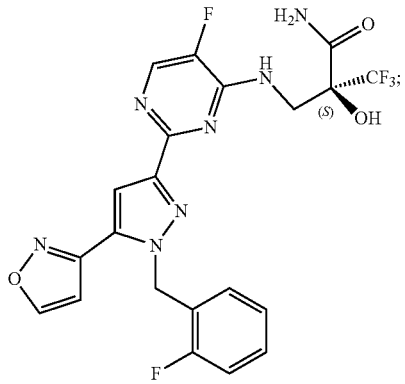

said process comprising:

a) treating bromo intermediate (15):

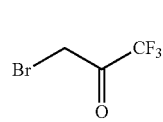

with an appropriate amount of trimethylsilanecarbonitrile, KCN or NaCN in the presence of an appropriate amount of a suitable organic amine, optionally in the presence of water as the solvent, at a suitable temperature to provide intermediate (16);

b) treating intermediate (16):

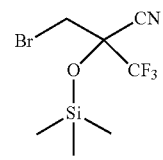

with an appropriate amount of a suitable strong aqueous mineral acid, at a suitable temperature, to provide intermediate (17):

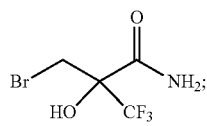

and c) treating intermediate (17) with an appropriate amount of ammonia, in a suitable protic solvent, at a suitable temperature, to provide amine (14):

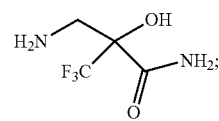

d) reacting intermediate amine (14) with an appropriate amount of (L)-malic acid, in a suitable aprotic polar solvent, at a suitable temperature, to provide a 1 to 1 salt of chiral intermediate (18B) and (L)-malic acid:

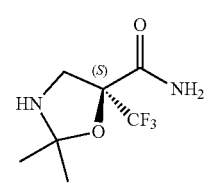

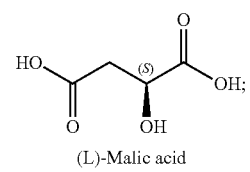

(L)-Malic acid followed by crystallization to separate this salt from the unreacted enantiomeric amine (14A):

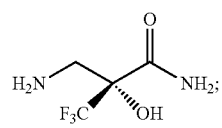

and e) heating the (L) malic acid salt obtained in step d), at a suitable temperature, in a suitable solvent, in order to liberate intermediate (14B)

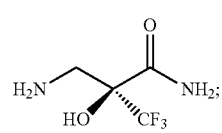

into solution, with loss of acetone, and reacting the resulting solution with an intermediate fluorochloro pyrimidine of Formula IV

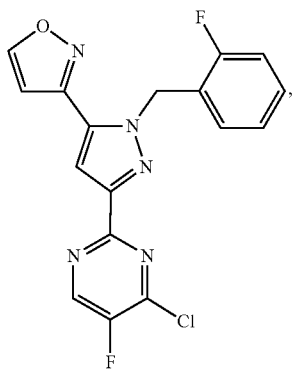

Formula IV in a suitable solvent, at a suitable temperature, optionally in the presence of an appropriate amount of a suitable organic amine.

13. The process according to claim 1, wherein (i) $R^1$ is a 5-membered heteroaryl ring containing up to three heteroatoms independently selected from N, O or S; (ii) $R_1$ is isoxazolyl; or (iii) $R^1$ is 3-isoxazolyl.

14. The process according to claim 1, wherein (i) $R^1$ is a 6-membered heteroaryl ring containing up to three ring nitrogen atoms; (ii) $R^1$ is pyridine or pyrimidine; or (iii) $R^1$ is phenyl.

15. The process according to claim 1, wherein $R^2$ is phenyl optionally substituted with up to three instances of $R^5$.

16. The process according to claim 15, wherein, $R^2$ is phenyl substituted with one instance of $R^5$, wherein $R^5$ is halogen or $R^5$ is fluoro.

17. The process according to claim 16, wherein $R^2$ is 2-fluorophenyl.

18. The process according to claim 15, wherein $R^2$ is phenyl substituted with two instances of $R^5$, wherein each instance of $R^5$ is independently selected from halogen or each instance of $R^5$ is fluoro.

* * * * *

UNITED STATES PATENT AND TRADEMARK OFFICE
CERTIFICATE OF CORRECTION

PATENT NO. : 11,834,444 B2
APPLICATION NO. : 16/315221
DATED : December 5, 2023
INVENTOR(S) : Song Xue et al.

Page 1 of 1

It is certified that error appears in the above-identified patent and that said Letters Patent is hereby corrected as shown below:

In the Claims

In Claim 5, Column 81, Line 65, please replace the structure " 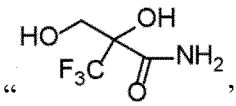 " with the structure -- 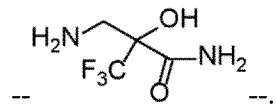 --.

Signed and Sealed this
Twenty-eighth Day of May, 2024

Katherine Kelly Vidal
*Director of the United States Patent and Trademark Office*